US006713606B1

(12) United States Patent
Smith et al.

(10) Patent No.: US 6,713,606 B1
(45) Date of Patent: Mar. 30, 2004

(54) CONJUGATES OF SOLUBLE PEPTIDIC COMPOUNDS WITH MEMBRANE-BINDING AGENTS

(75) Inventors: Richard Anthony Godwin Smith, Royston (GB); Ian Dodd, Royston (GB); Danuta Ewa Irena Mossakowska, Harlow (GB)

(73) Assignee: Adprotech Limited, Hertfordshire (GB)

( * ) Notice: Subject to any disclaimer, the term of this patent is extended or adjusted under 35 U.S.C. 154(b) by 0 days.

(21) Appl. No.: 09/612,314

(22) Filed: Jul. 7, 2000

Related U.S. Application Data

(63) Continuation-in-part of application No. 09/214,913, filed as application No. PCT/EP97/03715 on Jul. 8, 1997.

(30) Foreign Application Priority Data

Jul. 15, 1996 (GB) ............................................. 9614871

(51) Int. Cl.$^7$ .......................... A61K 38/00; C07K 14/00
(52) U.S. Cl. ........................... 530/350; 514/2; 530/402
(58) Field of Search ................................ 530/350, 402; 514/2

(56) References Cited

U.S. PATENT DOCUMENTS

| | | | | |
|---|---|---|---|---|
| 4,666,886 A | | 5/1987 | Baschang et al. | 514/17 |
| 5,326,700 A | | 7/1994 | Berg et al. | 435/240.2 |
| 5,472,939 A | | 12/1995 | Fearon et al. | 514/8 |
| 5,776,689 A | | 7/1998 | Karin et al. | 435/6 |
| 5,847,082 A | * | 12/1998 | Rother et al. | 530/350 |
| 5,856,300 A | * | 1/1999 | Rittershaus et al. | 514/12 |

FOREIGN PATENT DOCUMENTS

| | | |
|---|---|---|
| EP | 0152736 A2 | 8/1985 |
| EP | 0155387 A2 | 9/1985 |
| EP | 0207589 A1 | 1/1987 |
| EP | 9426786 * | 11/1994 |
| WO | WO91/16437 | 10/1991 |
| WO | 93/22343 | 11/1993 |
| WO | 94/00571 | 1/1994 |
| WO | WO94/03603 | 2/1994 |
| WO | 94/06826 | 3/1994 |

OTHER PUBLICATIONS

Hackhis Chemical Dictionary, McGraw Hill, Inc., 1969, pp. 25 and 331.*
Buss et al., Molecular and Cellular Biology 4(12): 2697–2704 (1984).
Kaplan et al., Molecular and Cellular Biology 10(3): 1000–1009 (1990).
Sigal et al., Proc. Natl. Acad. Sci. USA 91: 12253–12257 (1994).
Bacon–Baguley et al., Journal of Biological Chemistry 265 (4): 2317–2323 (1990).
Ye et al., Journal of Immunology 146(1) 250–256 (1991).
Database WPI; Derwent Publications Ltd.; AN 89–238911; XP002053042; "Modified Animal Hair Powder Heavy Metal Absorbents Etc. is Obtained by Reacting Mercaptan(s) or Mercapto–Modified Silicone Oil with Side Chains of Cystine in Hair"; JP 01 174 528 (Seiwa Kasei Co Ltd.) (Jul. 11, 1989).

\* cited by examiner

*Primary Examiner*—David Saunders
(74) *Attorney, Agent, or Firm*—Heller Ehrman White & McAuliffe

(57) ABSTRACT

The present invention provides, among other things, soluble derivatives of soluble polypeptides that incorporate membrane binding elements. Methods of making these soluble derivatives, and methods of using these soluble derivatives also are provided.

14 Claims, No Drawings

CONJUGATES OF SOLUBLE PEPTIDIC COMPOUNDS WITH MEMBRANE-BINDING AGENTS

This application is a continuation-in-part of U.S. Ser. No. 09/214,913, filed Mar. 16, 1999, which is a 371 of PCT/EP97/03715, filed Jul. 8, 1997. The entirety of these applications is hereby incorporated by reference.

This invention relates to polypeptide derivatives, their use in therapy and methods and intermediates for their production.

Essentially all protein drugs are administered as solutions and function in vivo in the solution phase. In biochemist and pharmacology, however, a large number of control and mediator proteins are associated with or function within or on the plasma membranes of cells. Except for soluble, truncated versions of one class of these molecules, no membrane-associated proteins have been developed as therapeutic agents. There are two main reasons for this situation. Firstly, overexpression of proteins that are retained in the membranes of the producer cells is limited by the the low capacity of membranes for proteins and often by the toxic effects of retention when expression is intrinsically efficient. Secondly, extraction of these proteins from membranes requires detergents or organic solvents, often results in inactivation of the protein, leads to difficulties in achieving the high purity needed for drug use and usually gives a product which is hard to formulate for intravenous administration. In addition, retention of very hydrophobic membrane anchoring elements may cause proteins to associate strongly with lipid-binding proteins in blood when administred intravenously thus preventing access to cell membranes.

Soluble, (truncated versions of membrane-associated proteins overcome the production difficulties associated with full length proteins. However such truncated molecules lack the membrane binding capability and specificity of the full length proteins which properties may be advantageous or even essential to the desired therapeutic activity.

The main classes of interaction of proteins with membranes can be summarised as follows:
1. Direct and specific interactions with phospholipid bead groups or with other hydrophilic regions of complex iipids or indirectly with proteins already inserted in the membrane. The latter may include all the types of intrinsic membrane protein noted below and such interactions are usually with exvacellular domains or Sequence loops of the membrane proteins;
2. Through anchoring by a single hydrophobic tranimembrane helical region near the terminus of the protein. These regions commonly prescnt a hydrophobic face around the entire circumference of the helix cylinder and transfer of this structure to the hydrophilic environment of bulk water is energetically unfavourable.
3. Further anchoring is often pmvided by a shon sequence of generally cationic aminoacids at the cytoplasmic side of the membrane, C-terminal to the transmembrane helix;
4. Through the use of multiple (normally 2–12 and commonly 4,7 and 10) transmembrane regions which are usually predicted to be helical or near-helical. Although these regions are normally hydrophobic overall, they frequently show some amphipathic behaviour—an outer hydrophobic face and an inner more hydrophilic one being identifiable within a helix bundle located in the lipid bilayer;
5. Through postranslationally linked phosphatidyl inositol moeities (GPI-anchors). These are generated by a specific biosynthetic pathway which recognises and removes a specific stretch of C-terminal aminoacids and creates a membrane-associating diacyl glycerol unit linked via a hydrophilic carbohydrate spacer to the polypeptide;
6. In a related process, single fatty acid groups such as myristoyl, palmitoyl or prenyl may be attached postranslationally to one or more sites in a protein (usually at N- or C-termini). Again, amino acids (such as the C-terminal CAAX box in Ras proteins) may be removed.

Artificial membranes are considered to be lipid complexes that mimic the basic properties of the cell membrane, i.e., a lipid vacuole with an aqueous interior and a surface chemistry that resembles the cell membrane. The artificial membrane typically contains phospholipids or mimics thereof and may be unilemellar or bilemellar and the outer surface will contain charged groups similar to the choline groups of the most abundant phospholipid. The prototype artificial membrane is known as a liposome and the technologies for the construction of liposomes including the incorporation of therapeutically useful agents into them is well known to those in the art. Liposomes have been evaluated in a number of disease states and liposomes containing the anti-fungal Amphotericin are commercially available. In addition, proteoliposomes have been described. For example, the use of immunoliposomes encapsulating amphotericin B has been reported to be of benefit in the treatment of experimental fungal infections in animal models (e.g. Hospenthal, D. et al (1989) J. Med. Microbiol. 30 193–197; Dromer, F. et al (1990) Antimicrob. Agents Chemother. 34 2055–2060).

Mimics of natural or artificial membranes are often related in structure and will mimic one or more properties of the membrane. One such example is the provision of an artificial surface having pendant groups which mimic the phospholipid zwitterionic groups which are found on the outside of cell surfaces. For example WO92/06719 (Biocompatibles Limited) discloses natural and synthetic phospholipids which may be coated on an artificial surface, e.g. a device which, in use, will come into contact with protein-containing or biological fluids, to provide improved biocompatibility and haemocompatibility and WO 94/16749 discloses additional zwitterionic groups that may be used to improve biocompatibility in a similar way.

The present invention provides a soluble derivative of a soluble polypeptide, said derivative comprising two or more heterologous membrane binding elements with low membrane affinity covalently associated with the polypeptide which elements are capable of interacting, independently and with thermodynamic additivity, with components of cellular or artificial membranes exposed to extracellular fluids.

By 'heterologous' is meant that the elements are not found in the native full length protein from which a soluble protein may be derived.

By 'soluble polypeptide' is meant a truncated derivative of a full length protein which lacks its natural membrane binding capability, and/or a polypeptide which has a solubility level in aqueous media of >100 $\mu$g/ml.

By 'membrane binding element with low membrane affinity' is meant that the element has only moderate affinity for membranes, that is a dissociation constant greater than 0.1 $\mu$M, preferably 1 $\mu$RM–1 mM. The elements preferably have a size <5 kDa.

The derivative should incorporate sufficient elements with low affinities for membrane components to result in a derivative with a high (preferably 0.01–10 nM dissociation constant) affinity for specific membranes. The elements combine so as to create an overall high affinity for the particular target membrane but the combination lacks such high affinity for other proteins for which single elements may be (low-affinity) ligands.

The elements should be chosen so as to retain useful solubility in pharmaceutial formulation media, preferably >100 µg/ml. Preferably at least one element is hydrophilic.

The invention thus promotes localisation of a therapeutic protein at cellular membranes and thereby provides one or more of several biologically significant effects with potential therapeutic advantages including:

Potency: If the protein is a receptor and an agonist or antagonist activity is localised on the same surface as the receptor itself, an increase in effective concentration may result from the reduction in the diffusional degrees of freedom.

Pharmacokinetics and dosing frequency: Interaction of a derivatised protein with long-lived cell types or serum proteins would be expected to prolong the plasma residence time of the protein and produce a depot effect through deposition on cell surfaces.

Specificity: Many clinically important pathological processes are associated with specific cell types and tissues (for example the vascular endothelium and the recruitment thereto of neutrophils bearing the sialyl Lexis, antigen to ELAM-1, see below). Hence targeting the modified protein to regions of membrane containing pathology-associated membrane markers may improve the therapeutic ratio of the protein targeted.

The derivatives of the invention may be used in association with artificial membranes or mimics thereof to allow delivery of the therapeutic protein to sites where it will provide therapeutic benefit. For example, polypeptides associated with liposomes formed by contacting liposomes with a derivative of the invention may be more stable than the free polypeptide. The liposome may incorporate a therapeutic agent, for example an antiflammatory or cytotoxic agent. The polypeptide derivative of the invention may thus be used to target the therapeutic agents When the polypeptide is itself a therapeutic agent. the liposome incorporated therapeutic agent may be used to enhance further the efficacy or tolerability of the therapy.

Association of derivatives of the invention with mimics of cell membranes may be used to concentrate the therapeutic protein at sites where therapeutically useful concentrations of underivatised protein might be difficult to achieve. For example, indwelling medical devices coated with mimics of the phospholipid zwitterionic groups which are found on the outside of cell surfaces, such as those disclosed in WO92/06719 and WO 94/16749, may be additionally treated with derivatives of the invention. For example complement inhibitors derivatised in accordance with the invention could be incorporated into the outer surface of indwelling catheters or hip replacements or heart valves in order to minimise development of inflammation associated with these operations.

It will be appreciated that all associations of heterologous amino acid sequences with a polypeptide which is a soluble derivative of a human protein will need to be assessed for potential immunogenicity, particularly where the amino acid sequence is not derived from a human protein. The problem can be minimised by using sequences as close as possible to known human ones and through computation of secondary structure and antigenicity indices.

Examples of protein therapeutic agents which may be modified according to the invention include but are not restricted to the following:

| Base Protein | Cell Target | Therapeutic Application |
|---|---|---|
| IL-4 Y124D mutein | B-cells | Anti-allergy (IL-4 antagonist) |
| Plasminogen activators e.g. Prourokinase, streptokinase, tissue-type plasminogen activator, reteplase | Erythrocytes, vascular endothelium | Prevention of venous thrombosis |
| Leptin | Choroid plexus, Hypothalamus | Weight loss (agonist) |
| Complement inhibitors* | Vascular endothelium, Myocytes, Erythrocytes, Lymphocytes | Ischaemic injury, transplantation, inflammation |
| scFv antibody against cytokines (IL-1, IL-, IL-5, IL-6) | Eosinophils | Asthma, allergic disease |
| Protein C | Vascular endothelium | Prevention of venous thrombosis |
| Antibodies against CD4, B7/CD28, CD3/TCR, CD11b(CR3) | Lymphocytes | Immunosuppresion |
| Interferon-β and derivatives | Lymphocytes | Immunomodulation, multiple sclerosis |

*Complement regulatory proteins e.g.: CR1 (CD35); DAF (CD55); MCP (CD46); CD59; Factor H; and C4 binding protein; and hybrids or muteins thereof such as CR1-CD59 (S.G.El Feki and D.T. Fearon Molecular Immunology 33 (supp 1). p 57, 1996). MCP-DAF (P.J. Higgins et al, J. Immunology. 158, 2872–2881, 1997) and soluble CR1 polypeptide fragments. The derivative preferably comprises two to eight, more preferably two to four membrane binding elements. Membrane binding elements are preferably selected from: fatty acid derivatives such as fatty acyl groups; basic amino acid sequences; ligands of known integral membrane proteins; sequences derived from the complementarity-determining region of monoclonal antibodies raised against epitopes of membrane proteins; membrane binding sequences identified through screening of random chemical or peptide libraries. The selection of suitable combination of membrane binding elements will be guided by the nature of the target cell membrane or components thereof.

Suitable fatty acid derivatives include myristoyl (12 methylene units) which is insufficiently large or hydrophobic to permit high affinity binding to membranes. Studies with myristoylated peptides (eg R. M. Peitzsch & S. McLaughlin, Biochemistry, 32, 10436–10443, 1993)) have shown that they have effective dissociation constants with model lipid systems of $-10^4$ M and around 10 of the 12 methylene groups are buried in the lipid bilayer. Thus, aliphatic acyl groups with about 8 to 18 methylene units, preferably 10–14, are suitable membrane binding elements. Other examples of suitable fatty acid derivatives include long-chain (8–18, preferably 10–14 methylene) aliphatic amines and thiols, steroid and farnesyl derivatives.

Membrane binding has been found to be associated with limited (single-site) modification with fatty acyl groups when combined with a cluster of basic amino acids in the protein sequence which may interact with acidic phospholipid head groups and provide the additional energy to target membrane binding. This combination of effects has been termed the 'myristoyl-electrostatic switch' (S.McLaughlin and A.Aderem, TIBS, 20,272–276, 1994; J. F.Hancock et al, Cell, 63, 133–139, 1990). Thus, a further example of suitable membrane binding elements are basic amino acid sequences such as those found in proteins such as Ras and MARCKS (myristoylated alanine-rich C-kinase substrate, P. J. Blackshear, J. Biol. Chem., 268, 1501–1504, 1993) which mediate the electrostatic 'switch' through reversible phosphorylation of serine residues within the sequence and a concomitant neutralisation of the net positive charge. Such sequences include but are not restricted to consecutive sequences of Lysine and Arginine such as (Lys)n where n is from 3 to 10, preferably 4 to 7. (SEQ ID NO: 53).

Suitable examples of amino acid sequences comprising basic amino acids include:

(i) DGPKKKKKKSPSKSSG (SEQ ID NO: 8)
(ii) GSSKSPSKKKKKKPGD (SEQ ID NO: 9)
(iii) SPSNETPKKKKKRFSFKKSG (SEQ ID NO: 10)
(iv) DGPKKKKKKSPSKSSK (SEQ ID NO: 11)
(v) SKDGKKKKKKSKTK (SEQ ID NO: 12)
(N-terminus on left)

Sequences i) to v) are examples of electrostatic switch sequences.

Examples of amino acid sequences derived from ligands of known integral membrane proteins include RGD-containing peptides such as GRGDSP (SEQ ID NO: 13) which are ligands for the $\alpha_{IIb}\beta_S$ integrin of human platelet membranes. Another example is DGPSEILRGDFSS (SEQ ID NO: 17) derived from human fibrinogen alpha chain, which binds to the GpIIb/IIIa membrane protein in platelets.

Further examples of such sequences include those known to be involved in interactions between membrane proteins such as receptors and the major histocompatibility complex. An example of such a membrane protein ligand is the sequence GNEQSFRVDLRTLLRYA (SEQ ID NO: 21) which has been shown to bind to the major histocompatibility complex class 1 protein (MHC-1) with moderate affinity (L.Olsson et al, Proc. Natl. Acad. Sci. USA. 91, 9086–909, 1994).

Yet further examples of such sequences employ a membrane insertive address specific for T-cells. Such sequence is derived from the known interaction of the transmembrane helix of the T-cell antigen receptor with CD3 (Nature Medicine 3, 84–88, 1997). Examples are peptides containing the sequence GFRILLLKV (SEQ ID NO: 22) such as:

SAAPSSGFRILLLKV (SEQ ID NO: 24)
AAPSVIGFRILLLKVAG (SEQ ID NO: 32)

An example of a ligand for an integral membrane protein is the carbohydrate ligand Sialyl Lewis' which has been identified as a ligand for the integral membrane protein ELAM-1 (M. L. Phillips et al, Science, 250, 1130–1132, 1990 & G. Walz et al, *Ibid,* 250, 1132–1135,1990).

Sequences derived from the complementarity-determining regions of monoclonal antibodies raised against epitopes within membrane proteins (see, for example, J. W. Smith et al, J.Biol.Chem. 270, 30486–30490, 1995) are also suitable membrane binding elements. as are binding sequences from random chemical libraries such as those generated in a phage display format and selected by biopanning operations in vitro (G. F.Smith and J. K.Scott, Methods in Enzymology, 217H, 228–257,1993) or in vivo (R.Pasqualini & E.Ruoslahti, Nature, 380, 364–366, 1996).

Optionally, conditional dissociation from the membrane may be incorporated into derivatives of the invention using mechanisms such as pH sensitivity (electrostatic switches), regulation through metal ion binding (using endogenous $Ca^{2+}$, $Zn^{2+}$ and incorporation of ion binding sites in membrane binding elements) and protease cleavage (e.g plasminolysis of lysine-rich membrane binding sequences to release and activate prourokinase)

Preferred derivatives of this invention have the following structure:

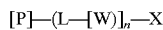

in which:
P is the soluble polypeptide,
each L is independently a flexible linker group,
each W is independently a peptidic membrane binding element,
n is an integer of 1 or more and
X is a peptidic or non-peptidic membrane-binding entity which may be covalently linked to any W.

Peptidic membrane binding elements are preferably 8 to 20 amino acids long and elements W are preferably located sequentially either at the N or C terminus of the soluble polypeptide. The amino acid sequences are linked to one another and to the soluble peptide by linker groups which are preferably selected from hydrophilic and/or flexible aminoacid sequences of 4 to 20 aminoacids; linear hydrophilic synthetic polymers; and chemical bridging groups.

Peptide linkages may be made chemically or biosynthetically by expression of appropriate coding DNA sequences. Non peptide linkages may be made chemically or enzymatically by post-translational modification.

The polypeptide portion of the derivatives of the invention may be prepared by expression in suitable hosts of modified genes encoding the soluble polypeptide of interest plus one or more peptidic membrane binding elements and optional residues such as cysteine to introduce linking groups to facilitate post translational derivatisation with additional membrane binding elements.

In a further aspect, therefore, the invention provides a process for preparing a derivative according to the invention which process comprises expressing DNA encoding the polypeptide portion of said derivative in a recombinant host cell and recovering the product and thereafter post translationally modifying the polypeptide to chemically introduce membrane binding elements.

In particular, the recombinant aspect of the process may comprise the steps of:

i) preparing a replicable expression vector capable, in a host cell, of expressing a DNA polymer comprising a nucleotide sequence that encodes said polypeptide portion;

ii) transforming a host cell with said vector;

iii) culturing said transformed host cell under conditions permitting expression of said DNA polymer to produce said polypeptide; and iv) recovering said polypeptide.

Where the polypeptide portion is novel, the DNA polymer comprising a nucleotide sequence that encodes the polypeptide portion as well as the polypeptide portion itself and S-derivatives thereof, also form part of the invention. In particular the invention provides a polypeptide portion of a derivative of the invention comprising the soluble peptide linked by a peptide bond to one peptidic membrane binding element and/or including a C-terminal cysteine, and DNA polymers encoding the polypeptide portion.

The recombinant process of the invention may be performed by conventional recombinant techniques such as described in Sambrook et al., Molecular Cloning: A laboratory manual 2nd Edition. Cold Spring Harbor Laboratory Press (1989) and DNA Cloning vols I, II and m (D. M. Glover ed., IRL Press Ltd).

The invention also provides a process for preparing the DNA polymer by the condensation of appropriate mono-, di- or oligomeric nucleotide units.

The preparation may be carried out chemically, enzymatically, or by a combination of the two methods, in vitro or in vivo as appropriate. Thus, the DNA polymer may be prepared by the enzymatic ligation of appropriate DNA fragments, by conventional methods such as those described by D. M. Roberts et al., in Biochemistry 1985, 24, 5090–5098.

The DNA fragments may be obtained by digestion of DNA containing the required sequences of nucleotides with appropriate restriction enzymes, by chemical synthesis, by enzymatic polymerisation, or by a combination of these methods.

Digestion with restriction enzymes may be performed in an appropriate buffer at a temperature of 20°–70° C., generally in a volume of 50 μl or less with 0.1–10 μg DNA.

Enzymatic polymerisation of DNA may be carried out in vitro using a DNA polymerase such as DNA polymerase 1 (Klenow fragment) in an appropriate buffer containing the nucleoside triphosphates dATP, dCTh, dGTP and dTTP as required at a temperature of 10°–37° C., generally in a volume of 50 μl or less.

Enzymatic ligation of DNA fragments may be carried out using a DNA ligase such as T4 DNA ligase in an appropriate buffer at a temperature of 4° C. to 37° C., generally in a volume of 50 μl or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J.Gait, H. W. D. Matthes M. Singh, B. S. Sproat and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et at., Journal of the American Chemical Society, 1983, 105, 661; N. D. Sinha, J. Biernat, J. McMannus and H. Koester, Nucleic Acids Research, 1984, 12, 4539; and H. W. D. Matthes et al., EMBO Journal, 1984, 3, 801. Preferably an automated DNA synthesiser (for example, Applied Biosystems 381A Synthesiser) is employed.

The DNA polymer is preferably prepared by ligating two or more DNA molecules which together comprise a DNA sequence encoding the polypeptide.

The DNA molecules may be obtained by the digestion with suitable restriction enzymes of vectors carrying the required coding sequences.

The precise structure of the DNA molecules and the way in which they are obtained depends upon the structure of the desired product The design of a suitable strategy for the construction of the DNA molecule coding for the polypeptide is a routine matter for the skilled worker in the art.

In particular, consideration may be given to the codon usage of the particular host cell. The codons may be optimised for high level expression in E. coli using the principles set out in Devereux et al., (1984) Nucl. Acid Res., 12, 387.

The expression of the DNA polymer encoding the polypeptide in a recombinant host cell may be carried out by means of a replicable expression vector capable, in the host cell, of expressing the DNA polymer. Novel expression vectors also form part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the polypeptide, under ligating conditions.

The ligation of the linear segment and more than one DNA molecule may be carried out simultaneously or sequentially as desired.

Thus, the DNA polymer may be preformed or formed during the construction of the vector, as desired. The choice of vector will be determined in part by the host cell, which may be prokaryotic, such as E. coli, or eukaryotic, such as mouse C127, mouse myeloma, chinese hamster ovary, fungi e.g. filamentous fungi or unicellular 'yeast' or an insect cell such as Drosophila. The host cell may also be in a transgenic animal. Suitable vectors include plasmids, bacteriophages, cosmids and recombinant viruses derived from, for example, baculoviruses or vaccinia.

The DNA polymer may be assembled into vectors designed for isolation of stable transformed mammalian cell lines expressing the fragment e.g. bovine papillomavirus vectors in mouse C127 cells, or amplified vectors in chinese hamster ovary cells (DNA Cloning Vol. II D. M. Glover ed. IRL Press 1985; Kaufman, R. J. et at.. Molecular and Cellular Biology 5, 1750–1759, 1985; Pavlakis G. N. and Hamer, D. H. Proceedings of the National Academy of Sciences (USA) 80, 397–401, 1983; Goeddel, D. V. et al., European Patent Application No. 0093619, 1983).

The preparation of the replicable expression vector may be carried out conventionally with appropriate enzymes for restriction, polymerisation and ligation of the DNA, by procedures described in, for example, Sambrook et al., cited above. Polymerisation and ligation may be performed as described above for the preparation of the DNA polymer. Digestion with restriction enzymes may be performed in an appropriate buffer at a temperature of 20°–70° C., generally in a volume of 50 μl or less with 0.1–10 μg DNA.

The recombinant host cell is prepared, in accordance with the invention, by transforming a host cell with a replicable expression vector of the invention under transforming conditions. Suitable transforming conditions are conventional and are described in, for example, Sambrook et al., cited above, or "DNA Cloning" Vol. II, D. M. Glover ed., IRL Press Ltd, 1985.

The choice of transforming conditions is determined by the host cell. Thus, a bacterial host such as E. coli, may be treated with a solution of $CaCl_2$ (Cohen et al.,Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol or by electroporation as for example described by Bio-Rad Laboratories, Richmond, Calif., USA, manufacturers of an electroporator. Mammalian cells in culture may be transformed by calcium co-precipitation of the vector DNA onto the cells or by using cationic liposomes.

The invention also extends to a host cell transformed with a replicable expression vector of the invention.

Culturing the transformed host cell under conditions permitting expression of the DNA polymer is carried out conventionally, as described in, for example, Sambrook et al., and "DNA Cloning" cited above. Thus, preferably the cell is supplied with nutrient and cultured at a temperature below 45° C.

The proteion product is recovered by conventional methods according to the host cell. Thus, where the host cell is bacterial such as E. coli and the protein is expressed intracellularly, it may be lysed physically, chemically or enzymatically and the protein product isolated from the resulting lysate. Where the host cell is mammamlian, the product is usually isolated from the nutrient medium.

Where the host cell is bacterial, such as *E. coli,* the product obtained from the culture may require folding for optimum functional activity. This is most likely if the protein is expressed as inclusion bodies. There are a number of aspects of the isolation and folding process that are regarded as important. In particular, the polypeptide is preferably partially purified before folding, in order to minimise formation of aggregates with contaminating proteins and minimise misfolding of the polypeptide. Thus, the removal of contaminating *E. coli* proteins by specifically isolating the inclusion bodies and the subsequent additional purification prior to folding are important aspects of the procedure.

The folding process is carried out in such a way as to minimise aggregation of intermediate-folded states of the polypeptide. Thus, careful consideration needs to be given to, among others, the salt type and concentration, temperature, protein concentration, redox buffer concentrations and duration of folding. The exact condition for any given polypeptide generally cannot be predicted and must be determined by experiment.

There are numerous methods available for the folding of proteins from inclusion bodies and these are known to the skilled worker in this field. The methods generally involve breaking all the disulphide bonds in the inclusion body, for example with 50 mM 2-mercaptoethanol, in the presence of a high concentration of denaturant such as 8M urea or 6M guanidine hydrochloride. The next step is to remove these agents to allow folding of the proteins to occur. Formation of the disulphide bridges requires an oxidising environment and this may be provided in a number of ways, for example by air, or by incorporating a suitable redox system, for example a mixture of reduced and oxidised glutathione.

Preferably, the inclusion body is solubilised using 8M urea, in the presence of mercaptoethanol, and protein is folded, after initial removal of contaminating proteins, by addition of cold buffer. Suitable buffers may be identified using the techniques described in I.Dodd et at, 'Perspectives in Protein Engineering and Complementary Technologies', Mayflower Publications, 66–69, 1995. A suitable buffer for many of the SCR constructs described herein is 20 mM ethanolamine containing 1 mM reduced glutathione and 0.5 mM oxidised glutathione. The folding is preferably carried out at a temperature in the range 1 to 5° C. over a period of 1 to 4 days.

If any precipitation or aggregation is observed, the aggregated protein can be removed in a number of ways, for example by centrifugation or by treatment with precipitants such as ammonium sulphate. Where either of these procedures are adopted, monomeric polypeptide is the major soluble produced.

If the bacterial cell secretes the protein, folding is not usually necessary.

The polypeptide portion of the derivative of the invention may include a C-terminal cysteine to facilitate post translational modification. A soluble polypeptide including a C-terminal cysteine also forms part of the invention. Expression in a bacterial system is preferred for proteins of moderate size (up to ~70 kDa) and with <~8 disulphide bridges. More complex proteins for which a free terminal Cys could cause refolding or stability problems may require stable expression in mammalian cell lines (especially CHO). This will also be needed if a carbohydrate membrane binding element is to be introduced post-translationally. The use of insect cells infected with recombinant baculovirus encoding the polypeptide portion is also a useful general method for preparing more complex proteins and will be preferred when it is desired to carry out certain post-translational processes (such as palmitoylation) biosynthetically (see for example. M. J.Page et al J.Biol.Chem. 264, 19147–19154, 1989)

A preferred method of handling proteins C-terminally derivatised with cysteine is as a mixed disulphide with mercaptoethanol or glutathione or as the 2-nitro, 5-carboxyphenyl thio-derivative as generally described below in Methods.

Peptide membrane binding elements may be prepared using standard solid state synthesis such as the Merrifield method and this method can be adapted to incorporate required non-peptide membrane binding elements such as N-acyl groups derived from myristic or palmitic acids at the N terminus of the peptide. In addition activation of an amino acid residue for subsequent linkage to a protein can be achieved during chemical synthesis of such membrane binding elements. Examples of such activations include formation of the mixed 2-pyridyl disulphide with a cysteine thiol or incorporation of an N-haloacetyl group. Both of these groups are capable of reaction with free thiols, through disulphide interchange and alkylation, respectively. Peptides can optionally be prepared as the C-terminal amide and/or with a conventional N-terminal blocking group such as acetyl.

The invention also provides a peptidic membrane binding element comprising one or more derivatisations selected from:
- a terminal cysteine residue optionally activated at the thiol group;
- an N-haloacetyl group (where halo signifies chlorine, bromine or iodine) located at the N-terminus of the the peptide or at an E-amino group of a lysine residue;
- an amide group at the C-terminus;
- an N-terminal blocking group; and
- a fatty acid N-acyl group at the N-terminus or at an amino group of a lysine residue.

Chemical bridging groups and reagents suitable for their formation include those described in EP0109653, EP0152736, EP0155388 and EP0284413, incorporated herein by reference. The bridging group is generally of the formula:

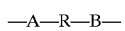   (I)

in which each of A and B, which may be the same or different, represents —CO—, —C(=NH$_2^+$)—, maleimido, —S— or a bond and R is a bond or a linking group containing one or more —(CH$_2$)— or meta-, ortho- or para-disubstituted phenyl units, preferably ortho or para, optionally together with a hydrophilic portion.

Where the polypeptide portion of the derivative of the invention and a peptidic membrane binding element both include a C-terminal cysteine the chemical bridging group will take the form —S—S—. The bridge is generated by conventional disulphide exchange chemistry, by activating a thiol on one polypeptide and reacting the activated thiol with a free thiol on the other polypeptide. Such activation procedures make use of disulphides which form stable thiolate anions upon cleavage of the S—S linkage and include reagents such as 2,2' dithiopyridine and 5,5'-dithio(2-nitrobenzoic acid, DTNB) which form intermediate mixed disulphides capable of further reaction with thiols to give stable disulphide linkages.

R may include moieties which interact with water to maintain the water solubility of the linkage and suitable moieties include —CO—NH—, —CO—NMe—, —S—S—, —CH(OH)—, —SO$_2$—, —CO$_2$—, —(CH$_2$CH$_2$—O)$_m$— and —CH(COOH)— where m is an integer of 2 or more, or linear hydrophilic polymers such as polyethylene glycol, polypropylene glycol, polyglycine, polyalanine or polysarcosine.

Other examples of R include —(CH$_2$)$_r$—, —(CH$_2$)$_p$—S—S—(CH$_2$)$_q$— and —(CH$_2$)$_p$—CH(OH)—CH(OH)—(CH$_2$)$_q$—, in which r is an integer of at least 2, preferably at least 4 and p and q are independently integers of at least 2

In a further aspect R may take the form —U—V—W— where U is (CH$_2$)$_2$CONH(CH$_2$)$_n$ in which n is an integer of 3 to 8, V is O, S, NR$_a$ or NR$_a$—NR$_a$ where each R$_a$ is H or C$_{1-6}$ alkyl, NH—O or O—NH, and W is benzyl substituted at the 2- or 4-position by the group B. In a preferred embodiment R is (CH$_2$)$_2$CONH(CH$_2$)$_n$NH—(4-phenyl) where n is an integer of 3 to 8. The bridging group of formula (I) may be derived from a linking agent of formula (II):

$$X—R_1—Y \qquad (II)$$

in which R$_1$ is a bond or a linking group and X and Y are functional groups reactable with surface amino acid groups. preferably a lysine or cysteine group, the N-terminal amino group, a catalytic serine hydroxyl or a protein attachment group, and X, R$_1$- and Y are chosen so as to generate the required bridging group —A—R—B—.

Preferred agents are those where X and Y are different, known as heterobifunctional agents. Each end of the agent molecule is reacted in turn with each polypeptide to be linked in separate reactions. Examples of heterobifunctional agents of formula (II) include:

N-succinimidyl 3-(2-pyridyldithio) propionate
succinimidyl 4-(N-maleimido) caproate
3-(2-pyridyl) methyl propionimidate hydrochloride
4'-amidinophenyl 4-N-[2-N-(3-[2-pyridyldithio]ethylcarbonyl)aminoethyl] aminobenzoate hydrochloride.

Other suitable agents are disclosed in EP0109653, EP0152736, EP0155388 and EP0284413, in particular those of formula (II) in EP0155388 and (III) in EP0284413 incorporated herein by reference.

In each case Y is capable of reacting with a thiol group on a polypeptide, which may be a native thiol or one introduced as a protein attachment group.

The protein attachment group is a functionality derived by modification of a polypeptide or protein with a reagent specific for one or more amino acid side chains, and which contains a group capable of reacting with a cleavable section on the other polypeptide. An example of a protein attachment group is a thiol group. An example of a cleavable section is a disulphide bond. Alternatively the cleavable section may comprise an a, dihydroxy function.

As an example, the introduction of a free thiol function by reaction of a polypeptide with 2-iminothiolane, N-succinimidyl 3-(2-pyridyldithio) propionate (with subsequent reduction) or N-acetyl homocysteine thiolactone will permit coupling of the protein attachment group with a thiol-reactive Y structure. Alternatively, the protein attachment group can contain a thiol-reactive entity such as the 6-maleimidohexyl group or a 2-pyridyl-dithio group which can react with a free thiol in X. Preferably, the protein attachment group is derived from protein modifying agents such as 2-iminothiolane that react with lysine ε-amino groups in proteins.

When X represents a group capable of reacting directly with the amino acid side chain of a protein. it is preferably an N-succinimidyl group. When X represents a group capable of reacting with a protein attachment group. it is preferably a pyridylthio group. When X represents a group capable of reacting with a catalytic serine hydroxyl it is preferably an 4-amidinophenyl ester group optionally substituted by one or more electron withdrawing groups which increases the reactivity of the ester, of the kind contained in the compounds of formula (II) in EP0155388 and (III) in EP0284413.

In the above processes, modification of a polypeptide to introduce a protein attachment group is preferably carried out in aqueous buffered media at a pH between 3.0 and 9.0 depending on the reagent used. For a preferred reagent, 2-iminothiolane, the pH is preferably 6.5–8.5. The concentration of polypeptide is preferably high (>10 mg/ml) and the modifying reagent is used in a moderate (1.1- to 5-fold) molar excess, depending on the reactivity of the reagent. The temperature and duration of reaction are preferably in the range 0°–40° C. and 10 minutes to 7 days. The extent of modification of the polypeptide may be determined by assaying for attachment groups introduced.

Such assays may be standard protein chemical techniques such as titration with 5,5'-dithiobis-(2-nitrobenzoic acid). Preferably, 0.5–3.0 moles of protein attachment group will be introduced on average per mole of polypeptide. The modified polypeptide may be separated from excess modifying agents by standard techniques such as dialysis, ultrafiltration, gel filtration and solvent or salt precipitation. The intermediate material may be stored in frozen solution or lyophilised.

Where the linking agent of formula (II) contains an amidino phenyl ester group X the agent is preferably first reacted with a polypeptide enzyme via the group X and the reaction is preferably carried out under the conditions described for the introduction of blocking groups in European Published Patent Application No. 0,009,879. Having been freed of excess reagent by suitable techniques such as high performance size exclusion chromatography or diafiltration, the acylated enzyme may then be reacted with the other polypeptide at a ratio of approximately 1:1 in a non-nucleophilic buffer at pH7.0–8.0 and 0°–30° C. for up to 6 h. However, it is preferable to conduct the coupling below 10° C. (preferably 0°–4° C.) in order to minimise the hydrolysis of the acylated enzyme.

Where a protein attachment group is introduced in this way, the bridging group (I) will be formed from a reaction of the linking agent (H) and the protein attachment group.

The polypeptides to be linked are reacted separately with the linking agent or the reagent for introducing a protein attachment group by typically adding an excess of the reagent to the polypeptide, usually in a neutral or moderately alkaline buffer, and after reaction removing low molecular weight materials by gel filtration or dialysis. The precise conditions of pH, temperature, buffer and reaction time will depend on the nature of the reagent used and the polypeptide to be modified. The polypeptide linkage reaction is preferably carried out by mixing the modified polypeptides in neutral buffer in an equimolar ratio. Other reaction conditions e.g. time and temperature, should be chosen to obtain the desired degree of linkage. If thiol exchange reactions are involved, the reaction should preferably be carried out under an atmosphere of nitrogen. Preferably, UV-active products are produced (eg from the release of pyridine 2-thione from 2-pyridyl dithio derivatives) so that coupling can be monitored.

After the linkage reaction, the polypeptide conjugate can be isolated by a number of chromatographic procedures such as gel filtration, ion-exchange chromatography, affinity chromatography or hydrophobic interaction chromatography. These procedures my be either low pressure or high performance variants.

The conjugate may be characterised by a number of techniques including low pressure or high performance gel filtration, SDS polyacrylamide gel electrophoresis or isoelectric focussing.

Membrane binding elements which are fatty acid derivatives are attached post translationally to a peptidic membrane binding element, preferably at the terminus of the polypetide chain. Preferably, where the recombinant polypeptide portion of the derivative of the invention contains the peptidic membrane binding element, it has a unique cysteine for coupling to the fatty acid derivative. Where the recombinant polypeptide has a cysteine residue, a thiol-derivative of the fatty acid is added to the refolded recombinant protein at a late stage in purification (but not necessarily the final stage) and at a reagent concentration preferably below the critical micelle concentration. One of the fatty acid derivative and the recombinant peptide will have the thiol group activated as described above for thiol interchange reactions. The fatty acid derivative is preferably a $C_{10-20}$ fatty acyl derivative of an amino$C_{2,6}$allrane thiol (optionally C-substituted) such as N-(2-myristoyl) aminoethanethiol or N-myristoyl L-cysteine and forms part of the invention.

Suitable examples of hydrophilic synthetic polymers include polyethyleneglycol (PEG), preferably $\alpha,\omega$ functionalised derivatives, more preferably $\alpha$-amino, $\omega$-carboxy-PEG of molecular weight between 400 and 5000 daltons which are linked to the polypeptide for example by solid-phase synthesis methods (amino group derivatisation) or by thiol-interchange chemistry.

Membrane binding elements derived from ligands of known integral membrane proteins, either amino acid sequences or carbohydrates, may be generated by post-translational modification using the glycosylation pathways of eukaryotic cells targeted to N-linked glycosylation sites in the peptide sequence.

Convenient generic final stage purification strategies are hydrophobic interaction chromatography (HIC) on C2–C8 media and cation exchange chromatography for separation of derivatised and underivatised proteins into which a hydrophobic-electrostatic switch combination has been inserted.

The derivatives of this invention are preferably administered as pharmaceutical compositions.

Accordingly, the present invention also provides a pharmaceutical composition comprising a derivative of the invention in combination with a pharmaceutically acceptable carrier.

The compositions according to the invention may be formulated in accordance with routine procedures for administration by any route, such as oral, topical, parenteral, sublingual or transdermal or by inhalation. The compositions may be in the form of tablets, capsules, powders, granules, lozenges, creams or liquid preparations, such as oral or sterile parenteral solutions or suspensions or in the form of a spray, aerosol or other conventional method for inhalation.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. Tablets may also contain agents for the stablisation of polypeptide drugs against proteolysis and absorbtion-enhancing agents for macromolecules. The tablets may be coated according to methods well known in normal pharmaceutical practice.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, is dissolved in the vehicle. In preparing solutions the compound can be dissolved in water for injection and filter sterilised before filling into a suitable vial or ampoule and sealing.

Parenteral formulations may include sustained-release systems such as encapsulation within microspheres of biodegradable polymers such as poly-lactic co-glycolic acid.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20mg ml$^{-1}$ of compound but more generally 0.1 to 10 mg ml-$^1$, for use with standard nebulisation equipment.

The quantity of material administered will depend upon the potency of the derivative and the nature of the complaint be decided according to the circumstances by the physician supervising treatment. However, in general, an effective amount of the polypeptide for the treatment of a disease or disorder is in the dose range of 0.01–100 mg/kg per day, preferably 0.1 mg–10 mg/kg per day, administered in up to five doses or by infusion.

No adverse toxicological effects are indicated with the compounds of the invention within the above described dosage range.

The invention also provides a derivative of the invention for use as a medicament.

The invention further provides a method of treatment of disorders amenable to treatment by a soluble peptide which comprises administering a soluble derivative of said soluble peptide according to the invention, and the use of a derivative of the invention for the preparation of a medicament for treatment of such disorders.

In one preferred aspect the present invention relates to derivatives for use in the therapy of disorders involving complement activity and various inflammatory and immune disorders.

In this preferred aspect the soluble polypeptide which is derivatised in accordance with the invention is a soluble complement inhibitor such as a soluble CR1 polypeptide fragment.

Constituting about 10% of the globulins in normal serum, the complement system is composed of many different proteins that are important in the immune system's response to foreign antigens. The complement system becomes activated when its primary components are cleaved and the products alone or with other proteins, activate additional complement proteins resulting in a proteolytic cascade. Activation of the complement system leads to a variety of responses including increased vascular permeability, chemotaxis of phagocytic cells, activation of inflammatory cells, opsonization of foreign particles, direct killing of cells and tissue damage. Activation of the complement system may be triggered by antigen-antibody complexes (the classical pathway) or, for example, by lipopolysaccharides present in cell walls of pathogenic bacteria (the alternative pathway).

Complement receptor type 1 (CR1) has been shown to be present on the membranes of erythrocytes, monocytes/macrophages, granulocytes, B cells, some T cells, splenic follicular dendritic cells. and glomerular podocytes. CR1 binds to the complement components C3b and C4b and has also been referred to as the C3b/C4b receptor. The structural organisation and primary sequence of one allotype of CR1 is known (Klickstein petal, 1987, J. Exp. Med. 165:1095–1112, Klickstein et al., 1988, J. Exp. Med. 168:1699–1717; Hourcade et al., 1988, J. Exp. Med. 168:1255–1270, WO 89/09220, WO 91/05047). It is composed of 30 short consensus repeats (SCRs) that each contain around 60–70 amino acids. In each SCR, around 29 of the average 65 amino acids are conserved. Each SCR has been proposed to form a three dimensional triple loop structure through disulphide linkages with the third and first and the fourth and second half-cystines in disulphide bonds. CR1 is further arranged as 4 long homologous repeats (LHRs) of 7 SCRs each. Following a leader sequence, the CR1 molecule consists of the N-terminal LHR-A, the next two repeats, LHR-B and LHR-C, and the most C-terminal LHR-D followed by 2 additional SCRs, a 25 residue putative transmembrane region and a 43 residue cytoplasmic tail.

Based on the mature CR1 molecule having a predicted N-terminal glutamine residue, hereinafter designated as residue 1, the first four SCR domains of LHR-A are defined herein as consisting of residues 2–58, 63–120, 125–191 and 197–252, respectively, of mature CR1.

Several soluble fragments of $CR_1$ have been generated via recombinant DNA procedures by eliminating the transmembrane region from the DNAs being expressed (WO 89/09220, WO 91/05047). The soluble CR1 fragments were functionally active, bound C3b andlor C4b and demonstrated Factor I cofactor activity depending upon the regions they contained. Such constructs inhibited in vitro complement-related functions such as neutrophil oxidative burst, complement mediated hemolysis, and C3a and C5a production. A particular soluble construct, sCR1/pBSCR1c, also demonstrated in vivo activity in a reversed passive Arthus reaction (WO 89/09220, WO 91/05047; Yeh et al., 1991, J. Immunol. 146:250), suppressed post-ischemic myocardial inflammation and necrosis (WO 89/09220, WO 91/05047; Weisman et al., Science, 1990, 249:146–1511; Dupe, R. et al. Thrombosis & Haemostasis (1991) 65(6) 695.) and extended survival rates following transplantation (Pruitt & Bollinger, 1991, J. Surg. Res 50:350; Pruitt et al., 1991 Transplantation 52; 868). Furthermore, co-formulation of sCR1/pBSCR1c with panisoylated human plasminogen-streptokinase-activator complex (APSAC) resulted in similar anti-haemolytic activity as sCR1 alone, indicating that the combination of the complement inhibitor sCR1 with a thrombolytic agent was feasible (WO 91/05047).

The soluble CR1 polypeptide fragment encoded by sCR1/pBSCR1c, residues 1–1929 of CR1, may be derivatised in accordance with the invention.

Soluble polypeptides corresponding to part of CR1 have been found to possess functional complement inhibitory, including anti-haemolytic, activity. WO94/00571 discloses soluble polypeptides comprising, in sequence, one to four short consensus repeats (SCR) selected from SCR 1, 2, 3 and 4 of long homologous repeat A (LHR-A) as the only structurally and functionally intact SCR domains of CR1 and including at least SCR3.

In preferred aspects, the polypeptide comprises. in sequence, SCR 1, 2, 3 and 4 of LHR-A or SCR 1, 2 and 3 of LHR-A as the only structurally and functionally intact SCR domains of CR1.

In one aspect, the polypeptides may be represented symbolically as follows:

$$NH_2—V^1—SCR1—W^1—SCR2—X^1—SCR3—Y^1—OH \quad (A)$$

in which SCR1 represents residues 2–58 of mature CR1, SCR2 represents residues 63–120 of mature CR1, SCR3 represents residues 125–191 of mature CR1, and $V^1$, $W^1$, $X^1$ and $Y^1$ represent bonds or short linking sequences of amino acids, preferably 1 to 5 residues in length and which are preferably derived from native interdomain sequences in CR1.

In a preferred embodiment of formula (I), $W^1$, $X^1$ and $Y^1$ represent residues 59–62, 121–124 and 192–196, respectively, of mature CR1 and $V^1$ represents residue 1 of mature CR1 optionally linked via its N-terminus to methionine.

In another aspect the polypeptides may be represented symbolically as follows:

$$NH_2-V^2-SCR1-W^2-SCR2-X^2-SCR3-Y^2-SCR4-Z^2OH \quad (B)$$

in which SCR1, SCR2 and SCR3 are as hereinbefore defined, SCR4 represents residues 197–252 of mature CR1 and $V^2, W^2, X^2, Y^2$ and $Z^2$ represents bonds or short linking sequences of amino acids. preferably 1 to 5 residues in length and which are preferably derived from native interdomain sequences in CR1.

In preferred embodiments of formula (II), $W^2, X^2, Y^2$ and $Z^2$ represent residues 59–62, 121–124, 192–196, and residues 253 respectively, of mature CR1 and $V^2$ represents residue 1 of mature CR1 optionally linked via its N-terminus to methionine.

In one particular embodiment of formula (B) arginine 253 is replaced by histidine.

In the preferred embodiment of formula (B), residue 235 is arginine.

In one further aspect, the polypeptide may be represented symbolically as follows:

$$NH_2-X^3-SCR3-Y^3-OH \quad (C)$$

in which SCR3 is as hereinbefore defined and $X^3$ and $Y^3$ represent bonds or short linking sequences of amino acids, preferably 1 to 5 residues in length and which are preferably derived from native interdomain sequences in CR1.

In a preferred embodiment of formula (C) $X^3$ represents amino acids 122–124 of mature CR1 optionally linked to methionine at its N-terminus and $Y^4$ represents amino acids 192–196 of mature CR1.

In another further aspect, the polypeptide may be represented symbolically as follows:

$$NH_2-X^4-SCR3-Y^4-SCR4-Z^4-OH \quad (D)$$

in which SCR3 and SCR4 are as hereinbefore defined and $X^4, Y^4$ and $Z^4$ represent bonds or short linking sequences of amino acids, preferably 1 to 5 residues in length and which are preferably derived from native interdomain sequences in CR1.

In a preferred embodiment of formula (D) $X^4$ represents amino acids 122–124 of mature CR1 optionally linked to methionine at its N-terminus and $Y^4$ and $Z^4$ represent amino acids 192–196 and 253 respectively of mature CR1.

The soluble CR1 polypeptide is derivatised in accordance with the invention by any convenient strategy from those outlined above. In a preferred embodiment the soluble CR1 polypeptide consists of residues 1–196 of CR1 and with an N-terminal methionine and the derivative comprises a myristoyl group and one or more polypeptides sequence selected from DGPKKKKKKSPSKSSGC (SEQ ID NO: 36)
GSSKSPSKKKKKKPGDC (SEQ ID NO: 5)
CDGPKKKKKKSPSKSSK (SEQ ID NO: 18)
SKDGKKKKKKSKTKC (SEQ ID NO: 19)
CSAAPSSGFRILLLKV (SEQ ID NO: 20)
AAPSVIGFRILLLKVAGC (SEQ ID NO: 43)
and
DOPSEILRGDFSSC (SEQ ID NO: 44)
(N-terminus on left).

The soluble complement inhibitor, such as a soluble CR1 polypeptide, derivative of this invention is useful in the treatment of many complement-mediated or complement-related diseases and disorders including, but not limited to, those listed below.

Disease and Disorders Involving Complement Neurological Disorders
    multiple sclerosis
    stroke
    Guillain Barré Syndrome
    traumatic brain injury
    Parkinson's disease
    allergic encephalitis
    Alzheimer's disease Disorders of Inappropriate or Undesirable Complement Activation
    haemodialysis complications
    hyperacute allograft rejection
    xenograft rejection
    corneal graft rejection
    interleukin-2 induced toxicity during IL-2 therapy
    paroxysmal nocturnal haemoglobinuria Inflammatory Disorders
    inflammation of autoimmune diseases
    Crohn's Disease
    adult respiratory distress syndrome
    thermal injury including burns or frostbite
    uveitis
    psoriasis
    asthma
    acute pancreatitis Post-Ischemic Reperfusion Conditions
    myocardial infarction
    balloon angioplasty
    atherosclerosis (cholesterol-induced) & restenosis
    hypertension
    post-pump syndrome in cardiopulmonary bypass or renal haemodialysis
    renal ischemia
    intestinal ischaemia
        Infectious Diseases or Sepsis
    multiple organ failure
    septic shock Immune Complex Disorders and Autoimmune Diseases
    rheumatoid arthritis
    systemic lupus erythematosus (SLE)
    SLE nephritis
    proliferative nephritis
    glomerulonephritis
    haemolytic anemia
    myasthenia gravis Reproductive Disorders
    antibody- or complement-mediated infertility Wound Healing The present invention is also directed to a pharmaceutical composition for treating a disease or disorder associated with inflammation or inappropriate complement activation comprising a therapeutically effective amount of a soluble complement inhibitor, such as a soluble CR1 polypeptide, derivative of this invention, and a pharmaceutically acceptable carrier or excipient.

The present invention also provides a method of treating a disease or disorder associated with inflammation or inappropriate complement activation comprising administering to a subject in need of such treatment a therapeutically effective amount of a soluble complement inhibitor, such as a soluble CR1 polypeptide, derivative of this invention.

In the above methods, the subject is preferably a human.

Further provided is the use of a soluble complement inhibitor, such as a soluble CR1 polypeptide, derivative of this invention in the manufacture of a medicament for the treatment of a disease or disorder associated with inflammation or inappropriate complement activation.

In order to inhibit complement activation and, at the same time, provide thrombolytic therapy, the present invention provides compositions which further comprise a therapeutically active amount of a thrombolytic agent. An effective amount of a thrombolytic agent is in the dose range of 0.01–10 mg/kg; preferably 0.1–5 mg/kg. Preferred thrombolytic agents include, but are not limited to, streptokinase, human tissue type plasminogen activator and urokinase molecules and derivatives, fragments or conjugates thereof. The thrombolytic agents may comprise one or more chains that may be fused or reversibly linked to other agents to form hybrid molecules (EP-A-0297882 and EP 155387), such as, for example, urokinase linked to plasmin (EP-A-0152736), a fibrinolytic enzyme linked to a water-soluble polymer (EP-A-0183503). The thrombolytic agents may also comprise muteins of plasminogen activators (EP-A-0207589). In a preferred embodiment, the thrombolytic agent may comprise a reversibly blocked in vitro fibrinolytic enzyme as described in U.S. Pat. No. 4,285,932. A most preferred enzyme is the p-anisoyl plasminogen-streptokinase activator complex, anistreplase as described in U.S. Pat. No. 4,808, 405 (Monk et al., 1987, Drugs 34:25–49).

Routes of administration for the individual or combined therapeutic compositions of the present invention include standard routes, such as, for example, intravenous infusion or bolus injection. Active complement inhibitors and thrombolytic agents may be administered together or sequentially, in any order.

The present invention also provides a method for treating a thrombotic condition, in particular acute myocardial infarction, in a human or non-human animal. This method comprises administering to a human or animal in need of this treatment an effective amount of a soluble complement inhibitor, such as a soluble CR1 polypeptide, derivative according to this invention and an effective amount of a thrombolytic agent.

Also provided is the use of a soluble complement inhibitor, such as a soluble CR1 polypeptide, derivative of this invention and a thrombolytic agent in the manufacture of a medicament for the treatment of a thrombotic condition in a human or animal. Such methods and uses may be carried out as described in WO 91/05047.

This invention further provides a method for treating adult respiratory distress syndrome (ARDS) in a human or non-human animal. This method comprises administering to the patient an effective amount of a soluble complement inhibitor, such as a soluble CR1 polypeptide, derivative according to this invention.

The invention also provides a method of delaying hyperacute allograft or hyperacute xenograft rejection in a human or non-human animal which receives a transplant by administering an effective amount of a soluble complement inhibitor, such as a soluble CR1 polypeptide, derivative according to this invention. Such administration may be to the patient or by application to the transplant prior to implantation.

The invention yet further provides a method of treating wounds in a human or non-human animal by administering by either topical or parenteral e.g. intravenous routes, an effective amount of a soluble complement inhibitor, such as a soluble CR1 polypeptide derivative according to this invention.

In another preferred aspect the soluble polypeptide is a thrombolytic agent such as prourokinase, streptokinase, tissue-type plasminogen activator or reteplase and the derivative of the invention is useful in the treatment of thrombotic disorders such as acute myocardial infarction. The invention thus provides a pharmaceutical composition for treating thrombotic disorders comprising a therapeutically effective amount of a derivative of a thrombolytic agent according to the invention, and a pharmaceutically acceptable carrier or excipient. The invention further provides a method of treatment of thrombotic disorders by administering an effective amount of a derivative of a thrombolytic agent according to the invention, and the use of such derivative in the preparation of a medicament for the treatment of thrombotic disorders.

The following Methods and Examples illustrate the invention.

GENERAL METHODS USED IN EXAMPLES (i) DNA Cleavage

Cleavage of DNA by restriction endonucleases was carried out according to the manufacturer's instructions using supplied buffers. Double digests were carried out simultaneously if the buffer conditions were suitable for both enzymes. Otherwise double digests were carried out sequentially where the enzyme requiring the lowest salt condition was added first to the digest. Once the digest was complete the salt concentration was altered and the second enzyme added.

(ii) DNA ligation

Ligations were carried out using T4 DNA ligase purchased from Promega, as described in Sambrook et al, (1989) Molecular Cloning: A Laboratory Manual 2nd Edition. Cold Spring Harbour Laboratory Press.

(iii) Plasmid isolation

Plasmid isolation was carried out by the alkaline lysis method described in Sambrook et al, (1989) Molecular Cloning: A Laboratory Manual 2nd Edition. Cold Spring Harbour Laboratory Press or by one of two commercially available kits: the Promega Wizard™ Plus Minipreps or Qiagen Plasmid Maxi kit according to the manufacturer's instructions.

(iv) DNA fragment isolation

DNA fragments were excised from agarose gels and DNA extracted using one of three commercially available kits: the QIAEX gel extraction kit or Qiaquick gel extraction kit (QIAGEN Inc., USA), or GeneClean (Bio 101 Inc, USA) according to the manufacturer's instructions.

(v) Introduction of DNA into E. coli

Plasmids were transformed into E. coli BL21(DE3) (Studier and Moffat, (1986), J. Mol. Biol 189:113), E. coli XLI-blue, BL21 (DE3) pLys-S or BLR (DE3) pLys-S that had been made competent using calcium chloride as described in Sambrook et al., (1989). Cell lines were purchased as frozen competent cultures from Stratagene. E. coli JM109 was purchased as a frozen competent culture from Promega.

(vi) DNA sequencing

Plasmid DNA was sequenced on a Vistra DNA Labstation 625. The sequencing chemistry was performed using Amersham International's Thermo Sequenase fluorescent dye-terminator cycle sequencing kit' (RPN 2435), in conjunction with their FMP fluorescent dye-terminator precipitation kit' (RPN 2433) according to the manufacturer's instructions.

The sequences produced by the above procedure were analysed by a Perkin Elmer ABI Prism 377 DNA Sequencer. This is an electrophoretic technique using 36 cm×0.2mm 4% acrylamide gels, the fluorescently labeled DNA fragments being detected by a charge coupled device camera according to the manufacturer's instructions.

(vii) Production of oligonucleotides

Oligonucleotides were purchased from Cruachem.

(viii) pBROC413

The plasmid pT7-7 [Tabor, S (1990), Current Protocols in Molecular Biology, F. A. Ausubel, Brent. R. E. Kingston, D. D. Moore, J. G. Seidman, J. A. Smith, and K. Struhl,eds.] pp.16.2.1–16.2.11, Greene Publishing and Wiley-lnterscience,New York.] contains DNA corresponding to nucleotides 2065–4362 of pBR322 and like pBR322 can be mobilized by a conjugative plasmid in the presence of a third plasmid ColK. A mobility protein encoded by ColK acts on the nic site at nucleotide 2254 of pBR322 initiating mobilization from this point. pT7-7 was digested with LspI and BglII and the protruding 5' ends filled in with the Klenow fragment of DNA PolymeraseI. The plasmid DNA fragment was purified by agarose gel electrophoresis, the blunt ends ligated together and transformed into *E. coli* DH1 by electroporation using a Bio-Rad Gene Pulser and following the manufacturers recommended conditions. The resultant plasmid pBROC413 was identified by restriction enzyme analysis of plasmid DNA.

The deletion in pBROC413 from the LspI site immediately upstream of the f10 promoter to the BglII site at nucleotide 434 of pT7-7 deletes the DNA corresponding to nucleotides 2065–2297 of pBR322. The nic site and adjacent sequences are therefore deleted making pBROC413 non mobilizable.

(ix) Sodium dodecyl sulphate polyacrylamide gel electrophoresis (SDS PAGE)

SDS PAGE was carried out generally using the Novex system (British Biotechnology) according to the manufacturer's instructions. Prepacked gels of 4–20% acrylamide were used. Samples for electrophoresis, including protein molecular weight standards (for example LMW Kit, Pharmacia or Novex Mark 12) were usually diluted in 1%(w/v) SDS-containing buffer (with or without 5%(v/v) 2-mercaptoethanol), and left at room temperature for about 10 to 30 min before application to the gel.

(x) Reduction of disulphides and modification of thiols in proteins

There are a number of methods used for achieving the title goals. The reason it may be necessary to carry out selective reduction of disulphides is that during the isolation and purification of multi-thiol proteins, in particular during refolding of fully denatured multi-thiol proteins, inappropriate disulphide pairing can occur. In addition, even if correct disulphide paring does occur, it is possible that a free cysteine in the protein may become blocked, for example with glutathione. These derivatives are generally quite stable. In order to make them more reactive, for example for subsequent conjugation to another functional group, they need to be selectively reduced, with for example dithiothreitol (DTT) or Tris (2-carboxyethyl) phosphine.HCl (TCEP) then optionally modified with a function which is moderately unstable. An example of the latter is Ellmans reagent (DTNB) which gives a mixed disulphide. In the case where treatment with DTNB is omitted, careful attention to experimental design is necessary to ensure that dimerisation of the free thiol-containing protein is minimised. Reference to the term 'selectively reduced' above means that reaction conditions eg. duration, temperature, molar ratios of reactants have to be carefully controlled so that reduction of disulphide bridges within the natural architecture of the protein is minimised. All the reagents are commercially available eg. from Sigma or Pierce.

The following general examples illustrate the type of conditions that may be used and that are useful for the generation of free thiols and their optional modification. The specific reaction conditions to achieve optimal thiol reduction and/or modification are ideally determined for each protein batch.

TCEP may be prepared as a 20 mM solution in 50 mM Hepes (approx. pH 4.5) and may be stored at –40 degrees C. DTT may be prepared at 10 mM in sodium phosphate pH 7.0 and may be stored at –40 degrees C. DTNB may be prepared at 10 mM in sodium phosphate pH 7.0 and may be stored at –40 degrees C. All of the above reagents are typically used at molar equivalence or molar excess over protein concentration, the precise concentrations ideally identified experimentally. The duration and the temperature of the reaction are similarly determined experimentally. Generally the duration would be in the range 1 to 24 hours and the temperature would be in the range 2 to 30 degrees C. Excess reagent may be conveniently removed by buffer exchange, for example using Sephadex G25 or Sephadex G50. A suitable buffer is 0.1M sodium phosphate pH7.0 or the solution may be left untreated.

EXAMPLES

Example 1

Prepared a [N-(Myristoyl) 3-aminoethane thiol (MAET)

Myristoyl chloride (1.0 mmol) was added with vigorous stirring to ice-cooled dry pyridine (1.0 ml), and followed immediately by N-hydroxysaccinimide (1.5 mmol). The mixture was stirred for 4 h at ambient temperature (–23° C.). 2-aminoethanethiol free base (1.1 mmol) was added as solid to the mixture and allowed to react for 6 h at ambient temperature, followed by 3 days at 4° C. The product was treated with water (5 ml), stirred for 1 h at ambient and filtered, washing with cold water. The white solid was dissolved in dimethylsulphoxide and reprecipitated with water and then vacuum dried over phosphorous pentoxide. The final yield was 0.21 g (–70%). Thiol titration using Ellman's reagent indicated that the product contained –45% free thiol.

Example 2

Synthesis of Myristoyl/Electrostatic Switch Peptide Reagent 1 (MSWP-1) (SEQ ID NO:27)

N-(Myristoyl) -Gly-Ser-Ser-Lys-Ser-Pro-Ser-Lys-Lys-Lys-Lys-Lys-Pro-Gly-Asp-(S-2-Thiopyridyl)Cys-$NH_2$ The peptide:
Gly-Ser-Ser-Lys-Ser-Pro-Ser-Lys-Lys-Lys-Lys-Lys-Pro-Gly-Asp-Cys-$NH_2$ (SEQ ID NO:5) was prepared using solid phase synthesis via the general Fmoc/tBu strategy developed by Sheppard and Atherton (E. Atherton and R. C. Sheppard, Solid Phase Synthesis, IRL Press, Oxford, 1989). Kieselguhr-supported polydimethylacrylamide resin (Macrosorb 100) was used as the solid support and was derivatised with ethylene diamine.

Coupling reactions were carried out using N-α-Fmoc protected reagents preactivated with N,N'- diisopropylcarbodiimide/N-hydroxybenzotriazole (in 4-fold molar excess) with bromophenol blue monitoring. Fmoc cleavages used 20% piperidine in DMF. Reactions to assemble the peptide chain were carried out by repeated cycles of coupling and deprotection including the attachment of the modified Rink linkage reagent (p-[(R,S)-α-[1-(9H-fluoreny-9-yl-methoxyformamido]2,4dimethoxybenzyl]-phenoxyacetic acid) designed to yield a C-terminal amide on final cleavage. The side chain functionalities of the individual amino-acids were protected as follows:

Ser(tButyl), Lys (Boc), Asp (O-tButyl), Cys (Trityl).

On completion of the peptide assembly and with the peptide still attached to the resin, the myristoyl group was attached to the amino group of the N terminal glycine by direct coupling of myristic acid by the same activation procedure. This modified peptide was then cleaved from the resin and the side-chain protecting groups removed at the same time by treatment with trifluoracetic acid containing 2.5% water and 2.5% triisopropyl silane.

The crude product was treated with 2,2' dithiopyridine in 0.01M ammonium acetate solution at pH 8–9 for approx. 2 h, then acidified with acetic acid and purified by preparative high performance liquid chromatography (HPLC) in 0.1% trifluoracetic acid (TFA)/water and 0.1% TFA/acetonitrile as gradient component. After lyophilisation, the peptide was a white amorphoes powder, soluble to at least 10 mg/ml in dimethylsulphoxide. Fast atom bombardment mass spectrometry gave main peaks at m/e 2107.8, 2129,7 and 2145.8, corresponding to the monoprotonated, monosodiated and monopotassiated molecular ions of the peptide. The 2-thiopyridyl content of the peptide was measured by dissolving is to around 0.03 mM to 0.2 mM in 0.1M Sodium Borate pH 8.0 and reducing by addition of dithiothreitol to 5 mM. The change in optical density at 343 nm was used to calculate the amount of pyridine 2-thione released using an extinction coefficient at this wavelength of 8080 $cm^{-1}$ $M^{-1}$. This indicated that the peptide content was approximately 60% of the dry weight.

Example 3

Synthesis of Myristory/Electrostatic Switch Peptide Reagent 2 (MSWF-2) (SEQ ID NO:28)

N-methyl-Cys(3-thiopyridyl) Asp-Gly-Pro-Lys-Lys-Lys-Lys-Lys-Lys-Ser-Prop-Ser Lys-Ser-Ser-Lys-(e-N-(Myristoyl))-NH$_2$ The peptide:
Cys-Asp-Gly-Pro-Lys-Lys-Lys-Lys-Lys-Lys-Ser-Pro-Ser-Lys-Ser-Ser-Lys-NH$_2$ (SEQ ID NO:18) was prepared by solid-phase synthesis using the general method described in Example 2 and with the following variations:

a. The C-terminal lysine was protected by alkylation with the 4-methyl trityl (MTT) group; all other lysines were N-ε protected with t-Boc group
b. MTT was removed with 1% v/v trifluoracetic acid in dichloromethane and the resulting unique free amino group derivatised with myristic acid prior to deprotection of the other lysines (as described in Example 2).

The N-terminus was acetylated with acetic anhydride upon completion of the peptide chain assembly. Generation of the 2-pyridyldithiocysteine moiety was by reaction of the deprotected peptide with 2,2'-dithiopyridine as described above. The product was purified as described in Example 2. Fast-atom bombardment mass spectrometry gave a molecular ion peak at 2221.3 (cf. 2220.3 for the monoprotonated theoretical mass).

| Amino-acid Analysis: | | | | |
|---|---|---|---|---|
| | Asx | Ser | Gly | Pro |
| Theory: | 1.0 | 4.0 | 1.0 | 2.0 |
| Found | 0.97 | 3.53 | 1.15 | 1.88 |

(Asx = Asn or Asp)

Amino-acid analysis indicated a net peptide content by weight of 68.7%. The 2-pyridyl disulphide content was approximately 60% by weight using the method of Example 2.

Example 4

Synthesis of Myristoyl/Electrostatic Switch Peptide Reagent 5 (MSWP-3) (SEQ ID NO:29)

N-(Myristoyl)-Ser-Lys-Asp-Gly-Lys-Lys-Lys-Lys-Lys-Lys-Ser-Lys-Thr-Lys-(S-3-Thiopyridyl)Cys-NH$_2$ The peptide:
Ser-Lys-Asp-Gly-Lys-Lys-Lys-Lys-Lys-Lys-Ser-Lys-Thr-Lys-Cys (SEQ ID NO:19) was prepared using the general solid-phase synthesis protocol of Example 2. Myristolyation, C-terminal amidation and derivatisation of the Cys residue were performed as described in Example 2. After purification, mass spectrometry gave the major peak at 2040.5, corresponding to a monoprotonated form (Theory: 2039.5)

| Amino-acid analysis: | | | | | |
|---|---|---|---|---|---|
| | Asx | Ser | Gly | Thr | Lys |
| Theory: | 1 | 2 | 1 | 1 | 9 |
| Found: | 1.02 | 2.04 | 1.14 | 1.06 | 8.85 |

The peptide content was about 56% by weight

Example 5

Synthesis of T-Cell Targeting Peptide Reagent 1 (TCTP-1) (SEQ ID NO:30)

N-ethyl-(2-thiopyethyl)Cys Ser-Ala-Ala-Pro-Ser-Ser-Gly-Pho-Arg-Ile-Leu-Leu-Leu-Lys-Val-CONH(CH$_3$)$_3$CH$_5$ The peptide:
(Cys-Ser-Ala-Ala-Pro-Ser-Ser-Gly-Phe-Arg-Ile-Leu-Leu-Leu-Lys-Val (SEQ ID NO:20) was prepared using the general solid-phase methodology of Example 2 and N-acetylated as in Example 3. The C-terminal was derivatized using n-decylamine in place of the Rink reagent. Mass spectrometry of the purified peptide gave a major peak at 1952.3 corresponding to a monoprotonated molecular in (Theory: 1951.1.) An ion at 1843.3 was also observed, this is believed to correspond to loss of the thiopyridyl group in the spectrophotometer.

Amino-acid analysis:

|  | Ser | Gly | Arg | Ala | Pro | Val | Ile | Phe | Leu | Lys |
|---|---|---|---|---|---|---|---|---|---|---|
| Theory: | 3 | 1 | 1 | 2 | 1 | 1 | 1 | 1 | 3 | 1 |
| Found: | 2.95 | 1.10 | 1.10 | 2.11 | 1.04 | 0.60 | 0.92 | 1.00 | 3.03 | 1.03 |

The peptide content by weight was 53%

Example 6

Expression and isolation of [SCR1-3]-Cys (SEQ ID NO:6)

(a) Construction of plasmid pDB1030 encoding [SCR 1-3]-Cys

The plasmid coding for SCR1-3 of LHR-A of CR1, pDB1013-5 (patent application WO 94/00571) was digested with restriction endonucleases EcoRI and HindIII and the 2.2 kB plasmid band was isolated from an agarose gel using a Qiagen Qisex DNA extraction kit according to the manufacturer's instructions. This is fragment 1. A second batch of pDB1013-5 was digested with Bml and EcoRI and the 196 bp band was extracted from agarose as above. This is fragment 2. Two oligonucleotides, SEQ ID No. 1 and SEQ ID No. 2, were annealed to give a final DNA concentration of 100 pmoles/ul. The annealed oligo has a Bml/EcoRI overhang and duplicates the sequence at the 3' end of pDB-1013-5 but in addition contains a codon coding for cysteine just before the stop codon. This is fragment 3.

Fragments 1,2 and 3 were ligated with T4 DNA ligase in a single reaction to give pDB1030. The ligated plasmid was transformed into competent *E. coli* IM109 purchased from Promega. Resulting colonies were analysed by restriction endonuclease digestion and DNA sequencing confirmed that the encoded amino acid sequence of SCR(1-3) (SEQ ID No.27 of WO 94/00571) had been altered by a single C-terminal cysteine residue to give SEQ ID No.6.

(b) Expression of [SCR1-3]-Cys from pDB1030 pD1030 was transformed into calcium chloride competent *E. coli* BL21(DE3) and resultant colonies were isolated and checked for plasmid content. To express protein from pDB1030 in *E. coli* BL21 (DE3), a single colony was inoculated into 10 ml LB-phosphate media (20 g/L tryptcine, 15 g/L yeast extract, 0.8 g/L NaCl, 0.2 g/L $Na_2HPO4$-0.1g/L $KH_2PO_4$) containing 50 ug/ml ampicillin. The culture was grown for 6 hours at 37° C. 230 r.p.m. before being used to inoculate 100 ml of the name media containing 50 ug/ml ampicillin. Growth was under the same conditions overnight. 25 ml of each culture were then used to isoculate 600 ml of the same media with 50 ug/ml ampicillin in 3 L erlenmeyer flasks. Cells were grown to an OD of 0.8–1.0 at $A_{600}$ nm. IFTG (isopropyl B-D galactopyranoside) was added to a final concentration of 1 mM and cells allowed to continue growth for a further 3–4 hours before harvesting by centrifugation at 8000 g/10 min. Pellet from 2L of culture was stored at −80° C.

(e) Isolation, refolding, purification and formulation of [SCR1-3]-Cys

The methods described are essentially those detailed in Dodd L et al (1995) Protein Expression and Purification 6 727–736.

I) Isolation of Solubilised Inclusion Bodies

The frozen cell pellet of *E. coli* BL21(DE3) (pDB1030) was resuspended in 50 mM Tris/50 mM NaCl/1 mM EDTA/0.1 mM PMSF pH 8.0 at a ratio of 33 ml for each Here of culture pellet. The suspension was transferred to a glass beaker surrounded by ion and sonicated (Heat systems—Ultrasonics W380; 50×50% pulse, pulse time=5 sec.) for typically 3–6 minutes. The disrupted pellet was then frozen and stored at −80° C. Approx. 2 weeks later the sonicate was thawed and centrifuged at approx. 8000 g for 20 min. The pellet was resuspended in 20 mM Tris/8M urea/1 mM EDTA/50 mM 2-mercaptoethanol pH 8.5 (200 mL) at room temperature by vigorous swirling, then left for 1 h at room temperature followed by overnight at 4° C.

II) Initial Purification using SP-Sepharose

To the viscous solution was added SP-Sepharose FF (approx. 30 g wet weight) this had been water washed and suction-dried. The mixture was swirled vigorously and left static for 1–2 h at room temperature. The supernatant was decanted, sampled and discarded. The remaining slurry was resuspended to a uniform suspension had poured into a glass jacket and allowed to settle into a packed bed. The columns was equilibrated with 0.02M Tris/8M urea/0.05M 2-mercaptoethanol/0.001M EDTA pH 8.5 at 4° C. When the $A_{280}$ of the eluate had stabilised at baseline, the buffer was changed to equilibration buffer additionally containing 1M NaCl. A single $A_{280}$ peak was eluted by the 1M NaCl-containing buffer; the volume was approx. 50 ml. The protein concentration of the solution was estimated by $A_{280}$ determination, using a molar extinction coefficient of 25000 $cm^{-1}$ of a sample that had been buffer-exchanged (Sephadex (325) into 50 mM formic acid. This showed the product had a protein concentration of 1.6 mg/ml. The solution was stored at −40° C.

III) Folding and Further Processing 25 ml of the SP-Sepharose-purified product was added gradually over a 1 min period to 780 ml freshly prepared, cold 0.02M ethanolamide/1 mM EDTA with continuous swirling, and left static for 1 h/4° C. Reduced glutathione (GSH) was added to 1 mM and xidised glutathione (GSSG) was added to 0.5 mM. The solution was clear and was left static approx 2–3° C. for 3 d. The solution was then ultrafiltered using a YM10 membrane to a final retentate volume of about 35 ml: the retentate was slightly cloudy and had the appearance of a translucent solution. It was stored for 12 days at 4° C. It was then spun at 30,000 g for 15 mins and the supernatant mixed with 9 vol. 0.1M $NaH_2PO_4$/1M $(NH_4)_2SO_4$ pH 7.0 (Buffer A) at room temperature and immediately centrifuged at 3000 rpm for 15 min. The supernatant was ultrafiltered (YM10) to about 4 ml and then buffer-exchanged into 0.1M sodium phosphate pH 7.0 (5.0 ml); this solution had a protein concentration of 1.7 mg/ml by A280 analysis. It was treated with dithio bis nitrobenzoic acid (DTNB) (8-fold molar excess) for 30 min at room temperature. Free thiol content based on A412 measurement and an extinction coefficient (for the fine thiombrobenzoate ion) of 13,600 was 6 ubl equivalent to only about 10% derivatisation to give Product A. The majority of the product was believed to be [SCR1-3]-Cys where the free C-terminal thiol was blocked by reaction with glutathione or 2-mercaptoethanol during the refolding stage.

(d) Alternative method for isolation, refolding, purification and formulation of [SCR1-3]-Cys The method was similar to that described above, except that it more closely followed the procedures described in Dodd et al (op cit.). Notably, the ultrafiltered retentate post refolding was immediately treated with ammonium sulphate followed by clarification by centrifugation and Butyl Tryc-pearl chromatography. The resulting A280-absorbing fractions that eluted at about 0.2 to 0.4M ammonium sulphate were pooled and regarded as Product B. Starting with a nominal 100 mg of fully reduced SCR1-3/cys, Product B contained 17 mg. The product contained one major species by non-reduced SDS PAGE with an estimated purity of >90% and an apparent molecular weight of 21,000. On the basis of studies with similarly produced preparations it was believed to be the S-glutathione and/or S-mercaptoethanol derivatised form of the parent protein, although at least some batches produced in a similar way or stored for a period of time might exist as the free cysteine variant. The product also contained a polypeptide with as apparent molecular weight of about 40,000. On the basis of studies with similar batches of protein enriched in this species it was identified as the dimer of [SCR1-3]-Cys.

Example 7

Expression and isolation of SCR1-3/switch fusion (SEQ ID NO:7)

$N_2N$-[SCR 1-3]-Asp-Cly-Pro-Lys-Lys-Lys-Lys-Lys-Lys-Ser-Pro-Ser-Lys-Ser-Ser-Gly-Cys-OH (a) Construction of plasmid pDB1031 encoding SCR1-3/switch Fragment 1 and fragment 2 of pDB1013-5 were the same as Example 6 above. Two digonucleotides, SEQ ID No. 3 and SEQ ID No. 4, prepared by Croachern were annealed to give a final DNA concentration of 100 pmoles/ul. The annealed oligo has an Banl/EcoRl overhang and duplicates the sequence at the 3' end of pDB1013-5 but in addition contains 17 additional codons coding for DGP-KKKKKKSPSKSSGC (SEQ ID NO:36) just before the stop codon. This is fragment 4.

Fragments 1, 2 and 4 wee ligated with T4 DNA ligase in a single reaction to give pDB1031. The ligated plasmid was transformed into competent *E. coli* JM109. Resulting colonies were analysed by restriction endonuclease digestion and DNA sequencing confirmed that the encoded amino acid sequence of SCR1-3 (SEQ ID 27 of WO 94/00571) had been altered by C terminal addition of amino acids DGP-KKKKKKSPSKSSGC (SEQ ID NO:36) to give SEQ ID NO:7.

(b) Expression of SCR1-3/switch from pDB1031 pDB1031 was transformed into calcium chloride competent *E. coli* (BL21(DE3) and resultant colonies were isolated and checked for plasmid content. To express protein from pDB1031 in *E. coli* BL21(DE3), a single colony was inoculated into 10 ml LB-phosphate media (20 g/L. trypione, 15 g/L yeast extract. 0.8 g/L NaCl, 0.2 g/L. $Na_2HPO_4$, 0.1 g/L $KH_2PO_4$) containing 50 ug/ml ampicillin. The culture was grown for 6 hours at 37° C. 230 r.p.m. before being used to inoculate 100 ml of the same media containing 50 ug/ml ampicillin. Growth was under the same conditions overnight. 25 ml of each culture were then used to inoculate 600 ml of the same media with 50 ug/ml ampicillin in 3 L erlenmeyer flasks. Cells were grown to an OD of 0.8–1.0 at $A_{600}$ nm. IPTG (isopropyl D-D galactopyranoside) was added to a final concentration of 1 mM and cells allowed to continue growth for a further 3–4 hours before harvesting by centrifugation at 8000 g/10 min. The cell pellet was frozen at −40 degrees C.

(c) Isolation, refolding, purification and formulation of SCR1-3/switch

The methods described are essentially those detailed in Dodd I. et al. (1995) Protein Expression and Purification 6 727–736, with some modifications.

I) Isolation of solubilised inclusion bodies

The frozen cell pellet of *E. coli* BL21(DE3) (pDB103)) was thawed and resuspended in 50 mM Tris/50 mM NaCl/1 mM EDTA/0.1 mM PMSF pH 8.0 at a ratio of 33 ml for each liter of culture pellet. The suspension was transferred to a glass beaker surrounded by ice and sonicated (Heat systems—Ultrasonics W380; 50×50% pulse, pulse time=5 sec.) for typically 3–6 mixtures. The disrupted pellet was then frozen and stored at −80° C. Approx. 1 d laser the sonicate was thawed and centrifuged at approx. 8000 g for 20 min. The pellet was resuspended is 20 mM Tris/8M urea/1 mM EDTA/50 mM 2-mercaptoethanol pH 8.5 (240 ml) at room temperature by vigorous swirling, then left for 1 h at room temperature followed by 5 days at 4° C.

II) Preliminary Purification using SP-Sepharose

To the viscous solution was added SP-Sepharose FF (approx. 30 g wet weight) that had been water washed and suction dried. The mixture was swirled vigorously and left static for approx. 2 h at room temperature. The supernatant was decanted, sampled and discarded. The remaining slurry was resuspended to a uniform suspension and poured into a glass jacket and allowed to settle into a packed bed. The column was equilibrated with 0.02M Tris/8M urea/0.05M 2-mercaptoethanol/0.001 M EDTA pH 8.5 at 4° C. When the $A_{280}$ of the eluate had stabilised at baseline, the buffer was changed to equilibration buffer additionally containing 1M NaCl. A single $A_{280}$ peak was eluted by the 1M NaCl-containing buffer; the volume was approx. 50 ml. The protein concentration of the solution was estimated by $A_{280}$ determination, using a molar extinction coefficient of 25000 $cm^{-1}$, of a sample that had been buffer-exchanged (Sephadex G25) into 50 mM formic acid. This showed the product had a protein concentration of 2.8 mg/ml. Analysis by SDS PAGE/main showed a major band (approx. 80%) at about 23,000Da. The solution was stored at −40° C.

III) Folding and Further Processing 14 ml of the SP-Sepharose-purified product was added gradually over a 1 min period to 430 ml freshly prepared, cold 0.05M Hepes/2M sodium chloride/1 mM EDTA pH 8.0 with continuous swirling, and left static for 1 h/4° C. Reduced glutathione (GSH) was added to 1 mM and oxidized glutathione (GSSG) was added to 0.5 mM. The solution was clear and was left static approx. 2–3° C. for 3 d. The solution was then ultrafiltered using a YM10 membrane to a final retentate volume of about 34 ml; the retentate was slightly cloudy. It was then spun at 25 000 g for 15 mins and the supernatant buffer-exchanged into 0.1M sodium phosphate pH 7.0 (46 ml). This fraction contained 2 mg of protein on the basis of an A280 determination. The solution was mixed with DTNB (20 mM; 0.65 ml) for 20 min at 4 degrees C. and then ultrafiltered to 2.4 ml. This retentate was buffer-changed into 0.1M sodium phosphate pH 7.0 (3.0 ml) and stored at −40 degrees C. Absorbance measurements at 412 mm on the solution prior to ultrafiltration suggested 25% derivatisation with DTNB.

(d) Alternative isolation, refolding, purification for formulation [SCR1-3]switch The method was similar to that described in (c) above, except that following the ultrafiltration step after refolding it more closely followed the procedures described in Dodd et al. (op cit.). Notably, the ultrafiltered retentate post refolding was immediately treated with ammonium sulphate followed by clarification by centrifugation and Butyl Sepharose chromatography. The resulting A280-absorbing fractions that eluted at about 0.2 to 0.4M ammonium sulphate were pooled and regarded as initial product. Additional treatment with TCEP essentially as above, followed by DTNB yielded a final product at 10 nM final protein concentrations. The final product contained one major species by non-reduced SDS PAGE with an estimated porky of >90% and an apparent molecular weight of 23,000 and contained about 2 moles TNB per mole of protein.

Example 8

Preparation of [SCR1-3]-Cys-S-S-[MSWP-1] (This sequence is a conjugate of SEQ ID NO:6 and the base peptide of SEQ ID NO:5).

22 h to give the free protein SEQ ID NO 6. MSWP-1 (20 mM in 0.1M sodium phosphate pH 7.0; 0.67 ml) was added and the solution incubated for a further 4 h. All 22 ml was buffer-exchanged into 50 mM formic acid using Sephades G50 (Vt 160 ml). Three A280 peaks were obtained. The first one, eluting at volume 56–106 ml, was the tide compound according to SDS PAGE analysis. The fraction was aliquoted and aliquots stored at −40 degrees C. or lyophilised. Amino acid analysis of the pro-lyophilisation solution indicated a protein concentration of 0.42 mg/ml. A280 (1 cm path length) was 0.44. C8 reverse phase HPLC and SDS PAGE both indicated a purity of approx 80%. The latter technique showed the major based had an apparent molecular weight of 23 000. The latter technique showed the major band had an apparent molecular

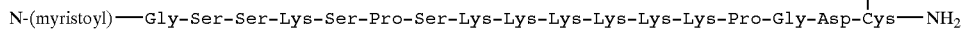

(a) Product A of Example 6(c) (1.5 ml) was treated with dithiothreitol (30 ul of 0.5M in water, final concentration 10 mM) for 60 min at 4° C. to give the free peptide SEQ ID NO 6. The yellow solution was gel filtered at 4° C. on a small column of Sephadex G-25 (PD-10, Pharmacia) into 0.05M Hepes HCl buffer pH 7.5 (3.0 ml). The slightly cloudy solution was mixed with a solution of MSWP-1 (Example 2) (3.8 mM dithiopyridyl equivalents, 150 ul) to a final concentration of 0.18 mM (~8 molar equivalents). The mixture was held for 2 h on ice and then gel filtered as before but using 2 PD10 columns (1.5 ml applied, 3.2 ml eluted). The final eluate was not cloudy and was stored frozen at −70° C. in aliquots of 0.4 ml.

(b) [SCR1-3]-Cys protein product B described in Example 6(d) (1.5 ml; 31 mM protein) was mixed with weight of 23 000, clearly shifted from the original percent molecular weight of 21,000; on reduction the 23,000 band shifted to two bands with molecular weights of approx 21,000 and approx 5,000. The lyophilisate was easily soluble in 50 mM formic acid or in PBS'A' (Dalbecco) at a protein concentration of 6 mg/ml.

(d) [SCR1-3]-Cys-S-S-[MSWP-1] from (c) was divided into 0.3 ml aliquots and freeze-dried. Individual aliquots were resolubilised in 50 mM formic acid (0.3 ml or 0.039 ml).

Example 9

Preparation of [SCR1-3/switch fusion]disulphide linked to [MAET] (SEQ ID NO:31)

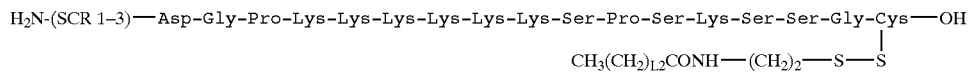

TCEP (20 mM; 0.007 ml) and incubated at room temperature for 23 h to give the free protein SEQ ID NO:6, MSWP-1 (Example 2) (10 mM; 0.093 ml) was added and the solution incubated for a further 4 h. 0.75 ml of the final solution was buffer-exchanged into 50 mM formic acid and aliquots left in solution or lyophilised. The product was >80% pure by SDS PAGE and had an apparent molecular weight of 23,000, clearly shifted from the original parent molecular weight of 21 000. The lyophilised was easily soluble in 50 mM formic acid at an estimated protein concentration of 2 mg/ml.

(c) [SCR1-3]-Cys protein product B described in Example 6(d) (21.6 ml; 31 uM protein) was mixed with TCEP (20 mM; 0.1 ml) and incubated at room temperature for Title compound can be synthesised using TNB-activated SCR1-3/switch (SEQ ID NO:7) prepared as in Example 7(d). The TNB-activated SCR1-3/switch is mixed with a molar excess of MAET (Example 1), which might be typically made up at 2.0 mg/ml in DMSO, equivalent to about 3 mM free thiol. Typical reaction conditions would be 1 to 4 hours at room temperature or overnight at 4 degrees C. using a protein concentration of 1 to 100 uM. The reaction may be monitored by checking the generation of yellow colour, which is caused by the release of free TNB ion. Ones the reaction is complete the solution may be buffer exchanged into a suitable buffer, for example 0.1M sodium phosphate pH 7.0, and stored at −40 degrees C. until required.

Example 10

Preparation of [SCR1-3/switch fusion] disulphide linked to [MSWP-1] (This sequence is a conjugate of SEQ ID NO: 7 and the base peptide of SEQ ID NO:5).

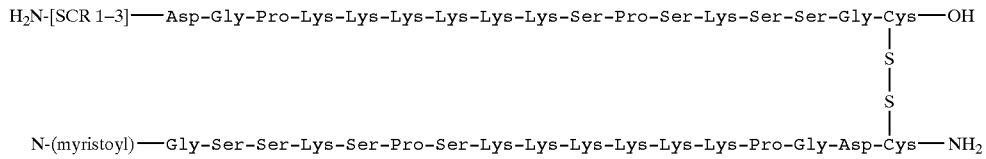

Method (a)

0.02 ml of MSWP-1 (Example 2, 10 mM in 0.1M sodium phosphate pH 7.0) was mixed with 0.005 ml of TCEP (20 mM in 50 mM Hepes) and left for 10 min at room temperature. The resultant solution was Solution A containing the myristoylated peptide of SEQ ID NO:5. TNB-activated SCR1-3/switch (SEQ ID NO:7) prepared in a similar way to that described in Example 7(c) (0.3 ml; 15 uM in 0.1M sodium phosphate pH 7.0) was mixed with 0.0056 ml of Solution A to give a theoretical MSWP-SH molar excess of five-fold over protein. The mixture was left for 4H at room temperature followed by 18 h at 4 degrees C. Analysis by SDS PAGE followed by protein staining indicated one major band at apparent $M_f$ 23 K, corresponding to unreacted protein, and a minor band at apparent $M_f$ 26K, corresponding to title protein.

Method (b)

TNB-activated SCR1-3/switch product (SEQ ID NO:7) (10 uM; 0.43 ml) prepared in a similar way to that described in Example 7(d) was mixed with TCEP (5 mM; 0.026 ml) and incubated for 17 h at room temperature to yield the free fusion protein SEQ ID NO:7. MSWP-1 (10 mM; 0.0086 ml) was added and incubation was continued for a further 4 h. Small particles or crystals were present in the solution, but it was otherwise clear. The particulate solution was buffer-exchanged into 50 mM formic acid (1.0 ml), aliquoted and frozen. Analysis by SDS PAGE under non-reducing conditions showed a number of bands, which included a species with as apparent molecular weight of 25,000 —the target species.

Example 11

Preparation of [SCR1: 1-1929]-Cys-S-S-[MSWP-1] (This sequence is a conjugate of SEQ ID NO: 52 and the base peptide of SEQ ID NO:5).

Human complement receptor 1 (CR1, CD35) is a known regulator of complement activation which has been produced in a recombinant soluble form containing all of the extracellular SCR domains of a major natural allotype (Fearon et al. WO 89/09220, WO 91/05047). This form (sCR1) has been expressed as an active protein in Chinese Hamster Ovary (CHO) cells. Mutagenesis of the DNA sequence immediately downstream of the codon for Cys-1924 is

Example 12

Preparation of [SCR1-3]-Cys-S-S-[MSWP-2] (This sequence is a conjugate of SEQ ID NO:6 and the base peptide of SEQ ID NO:18).

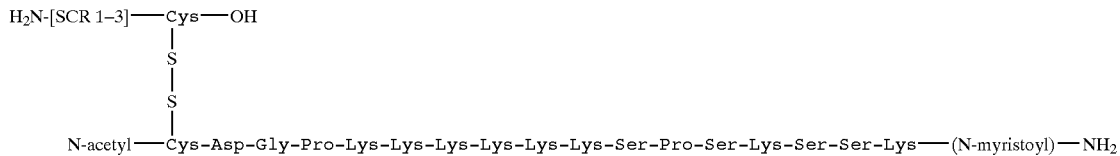

[SCR1-3]-Cys protein (SEQ ID NO:6) prepared in a similar way to that described in Example 6(d) (46 uM protein; 0.20 ml) was mixed with TCEP (5 mM; 0.0054 ml) was incubated at room temperature for approx. 20 h. 0.05 ml of this solution was mixed with 0.025 ml of 0.1M ethanolamine and 0.003 ml of MSWP-2 (see Example 3; 5 mM in DMSO;); the solution was incubated for a further 3 h at room temperature. SDS PAGE analysis showed the major band in the preparation had an apparent molecular weight of 23,000, clearly shifted from the original parent molecular weight of 21,000. The purity of the target protein was estimated from the SDS PAGE gel to be approx 80%.

Example 13

Preparation of [SCR1:1-3]-Cys-S-S-[MSWP-3] (This sequence is a conjugate of SEQ ID NO:6 and the base peptide of SEQ ID NO:19).

[SCR1-3]-Cys protein (SEQ ID NO:6) prepared in a similar way to that described in Example 6(d) (46 uM protein; 0.10 ml) was mixed with TCEP (5 mM; 0.0037 ml) and incubated at room temperature for approx. 18 h. 0.01 ml of 0.5M ethanolamine was added. 0.03 ml of this 0.11 ml solution was mixed with 0.0032 ml of MSWP-3 (see Example 4; 2 mM in 0.1M sodium phosphate pH 7.0); the solution was incubated for a further 3 h at room temperature. SDS PAGE analysis showed the major band in the preparation had an apparent molecular weight of 23,000, clearly shifted from the original parent molecular weight of 21,000. The purity of the target protein was estimated from the SDS PAGE gel to be approx. 80%.

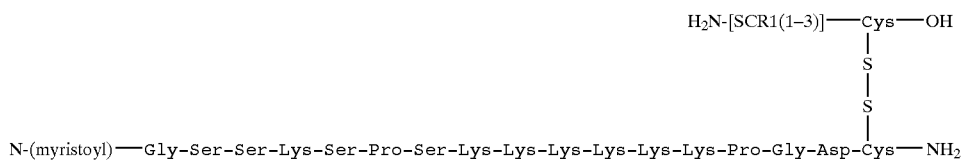

Example 14

Preparation of [SCR1-3]-Cys-S-S-[TCPT-1] (This sequence is a conjugate of SEQ ID NO:6 and the base peptide of SEQ ID NO:20).

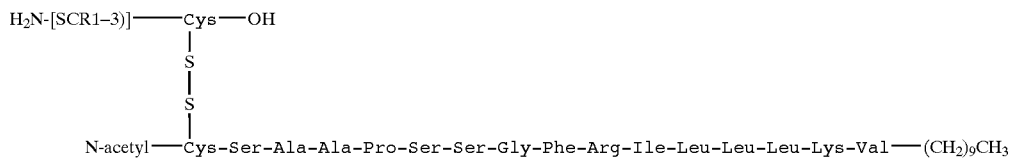

[SCR1-3]-Cys protein prepared in a similar way to that described in Example 6(d) (46 uM protein; 0.08 ml) was mixed with TCEP (5 mM; 0.0029 ml) and incubated at room temperature for approx. 18 h. 0.008 ml of 0.5M ethanolamine was added. 0.04 ml of this 0.088 ml solution was mixed with 0.0029 ml of TCPT-1 (see Example 5; 29 mM in DMSO). The TCPT-1 was added in 6 aliquots over a 2 h period to minimise aggregation. The solution was incubated for a further 2 h at room temperature. The final appearance of the mixture was one of a colloidal suspension and centrifugation at 2000 g for 1 min showed that the target protein was compartmentalised in the precipitate. SDS PAGE analysis showed the major band in the preparation had an apparent molecular weight of about 23,000, clearly shifted from the original parent molecular weight of 21,000. The purity of the target protein was estimated from the SDS PAGE gel to be approx 80%.

Example 15

Preparation of a Rabbit anti-(human erythrocyle membrane) antibody-[MSWP-1] conjugate (RAEM-MSWP-1) (This sequence is a conjugate of Rabbit anti-human erythrocyle membrane antibody and the base peptide of SEQ ID NO:5).

Rabbit polyclonal and (human erythrocyle membrane) (RAEM) antiserum (Dako, Denmark, 13 mg/ml, 0.25 ml) was diluted to 1.0 ml with 50 mM sodium phosphate 0.1M sodium chloride pH 7.4 (PBS) and treated with 30 ml of 100 mM 2-iminothiolane in PBS (freshly dissolved) for 30 min at 25° C. These conditions have been shown (R. A. G. Smith & R. Cassels, Fibrinolysis, 2, 189–195, 1988) to introduce an average of 2–3 free thiol groups per molecule of immunoglobulin G.

The product was purified by gel permeation chromatography on a small disposable columns of Sephadex G-25 m (PD-10, Pharmacia, Stockholm, Sweden) at 4° C. 2.5 ml of the product (total volume 3.0 ml, theoretical protein concentration ~6.1 mM) was treated with MSWP-1 (Example 2, 0.125 m of 5 mM solution in dimethyl sulphoxide, final conc ~240 uM) and incubated at 25° C. for 30 min. The product was gel-filtered on a PD10 column as above to give 3.0 ml of a solution ~5 uM in protein. This was stored frozen at −70° C.

Example 16

Preparation of a conjugate of Streptokinase and MSWP-1 (This sequence is a conjugate of Streptokinase and the base peptide of SEQ ID NO:5).

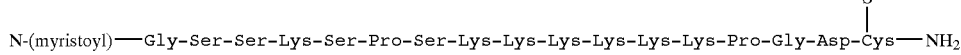

Streptokinase (SK) stock solution (Behringwerke, Marburg, Germany, 12.8 mg/ml, 271 uM, 2.5 ml) was gel filtered using a PD10 column into 3.2 ml of PBS buffer (see Example 15) containing 0.01% w/v Tween 80 [PST buffer]. Freshly made up 2-iminothiolane (64 ul of 100 mM) was added and the mixture incubated at 25° C. for 1 h. The product was gel filtered in 2×1.6 ml batches into 2×3.0 ml PST at 4° C. on two PD10 columns. This solution was stored in aliquots of 1.5 ml at −75° C.

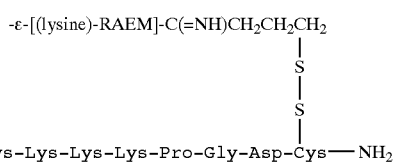

Titration of the product with Ellman's reagent (0.1 mM in 0.5 ml of 0.1M Triethanolamine, HCl pH 8.0) showed that it contained approximately 0.3 mM free thiol groups. This corresponds to an average of 3–3.5 thiol groups per molecular of SK. The stock thiolated SK solution (2×0.5 ml) was processed by modifying one aliquot with MSWP-1 (32 ml of 5 mM stock in DMSO), incubated 1 h at 25° C. and gel filtered (PD10 column) late 3.0 ml PST at 4° C. A control aliquot was processed in parallel without exposure to MSWP-1. Both products contained ~0.8 mg/ml protein based on as extinction coefficient of 0.76 $(mg/ml)^{-1}$ at 820 nm for SK and were stored at −75° C.

Example 17

Reversible linkage of MSWP-1 to the active center of Human Tissue-type Plasminogen Activator (This sequence is a conjugate of SEQ ID NO:51 and the base peptide of SEQ ID NO:5).

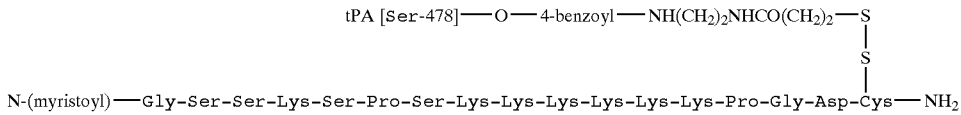

```
tPA [Ser-478]—O—4-benzoyl—NH(CH2)2NHCO(CH2)2—S
                                            |
                                            S
                                            |
N-(myristoyl)—Gly-Ser-Ser-Lys-Ser-Pro-Ser-Lys-Lys-Lys-Lys-Lys-Lys-Pro-Gly-Asp-Cys—NH2
```

The thiol-reactive acyl-enzyme 4-N-(2-N-(3-[2-pyridyldithio]-ethylcarbonyl)aminoethyl]aminobenzoyl-[Ser-478] human tissue-type plasminogen activator [PDAED->tPA] was prepared by the method of Smith and Cassels (Fibrinolysis, 2, 189–195, 1988). Tissue plasminogen activator (Actilyse, Boehringer Ingelheim, Germany, approx 2 mg) was dissolved in the PST buffer of Example 16 (1.0 ml) and treated with 25 ul of a 20 mM solution of 4'-amidinophenyl 4-N-[2-N-(3-[2-pyridyldithio]-ethylcarbonyl)aminoethyl]aminobenzonate hydrochloride (S. B. Kalindjian & R. A. G. Smith, Biochem. J. 248, 409–413, 1987) in dimethylsulphoxide. The mixture was incubated for 1 h at 25° C. and stored frozen at −80° C. It was reduced by addition of dithiothreitol (5 ul of 0.5M in water) for 30 min at 0° C. followed by buffer-exchange into PST buffer (3.0 ml) as described in Example 16. The product was divided immediately into a retained sample (0.6 ml) and a reaction sample (2.4 ml) which was mixed with MSWP-1 (Example 2, 100 ul of a 5 mM solution in dimethylsulphoxide) and incubated for 90 min on ice. The product was buffer-exchanged as above into 3.2 ml PST and stored in aliquots at −196° C.

Example 18

Expression and purification of [SCR1-3]-Cys (SEQ ID 6) from a formentation run.

(a) Formentation of *E. coli* harbouring the plasmid pDB1030

A frozen stock of *E. coli* harboring the plasmid pDB1030 was initially prepared by plating the culture out onto LB agar plus ampicillin at 100 μg/ml. 1 ml aliquots were preserved in a 10% glycerol/PBS cryopresservative and stored under liquid nitrogen. A 1 ml vial was thawed and was used to inoculate 100 ml $LB^{Amp100}$ primary seed medium (Difco Bactotryptose, 10 $gl^{-1}$; Difco yeast extract, 5 $gl^{-1}$; sodium chloride, 5 $gl^{-1}$; pH prosterilisation 7.4) in a 500 ml flask. The primary seed stage was incubated at 37° C. for 3 hours before transfer to the second seed stage, also 100 ml $LB^{Amp100}$ per 500 ml flask using a 1% inocultum. Following incubation as above for a further 4 hours a 1% inoculum was transferred to the tertiary seed stage, 10 liters $LB^{Amp100}$ in a 15 liter Biolafite fermenter. The 10 liters tertiary seed medium was sterilised in situ for 45 minutes at 121° C. before inoculation. Following incubation for 14.5 hours, the tertiary seed was transferred to the final stage fermenter as a 6% inoculum. Incubation conditions for the seed stage were as follows: airflow at 101 $min^{-1}$ (1.0 vvm), temperature 37° C., agitation at 400 rpm (1.9 $ms^{-1}$) and overpressure 0.2 bar. 300 liters Tryptone phosphate $medium^{Amp100}$ (Difco Bactotryptone, 20 $gl^{-1}$; Difco yeast extract, 15 $gl^{-1}$; sodium chloride, 8 $gl^{-1}$; disodium hydrogen orthophosphate, 2 $gl^{-1}$; potassium dihydrogen orthophosphate, 1 $gl^{-1}$; Dow Corning 1520 antifoam, 0.1 $gl^{-1}$; pH pre-sterilisation 7.4) was sterilised in situ for 30 minutes at 121° C. in a 450L Bioengineering fermenter. The fermenter was inoculated with 20 liter inoculum from the tertiary and stage and incubated under the following conditions:airflow 450L $min^{-4}$ (1.5 vvm), temperature 37° C., agitation 230 rpm (1.5 $ma^{-1}$) and overpressure 0.5 bar. After an $OD_{530\ mm}$ of 3.5 was obtained, 1 mM IPTG was added. Harvest followed after continued incubation for 2 hours. A cell slurry was recovered after primary centrifugation through a Westfalia CSA19 (two discharges). The calls were further spun at 4700 rpm (7000 g) for 30 minutes in a Sorvall RC3B centrifuge. The total cell yield (wet weight) was 2.98 Kg and was stored at −80 degrees C. in approx. 600 g lots.

(b) Isolation of inclusion bodies and purification of [SCR1-3]-Cys

Inclusion bodies from 100 g (wet weight) cell pellet were isolated and solubilised essentially as described in Example 6. The purification of target protein from resolubilised inclusion bodies was also as described in Example 6 with some modifications. The major ones were:

1. The use of Macroprep High S (Biorad) instead of S-Sepharose. 200 g of matrix was used for 100 g of cell pellet that had been sonicated. 1.4 g of approx. 60% pure target protein was produced in the solubilised and partially purified fractineon bodies.
2. Refolding of a 100 mg sample of the partially purified protein was carried out by diluting the fully denatured protein (2 mg/ml) 100-fold in cold 60 mM ethanolamine/1 mM EDTA, followed by addition of the glutathione redox couple.

The product of the above process was capable of being modified with MSWP-1 (Example 2) in a way similar to that described in Example 1.

Example 19

Expression and isolation of [SCR1-3(delN195-K196)]TNANKSLSSISCQT (SEQ ID NO:14)

(a) Construction of plasmid pBC04-29 encoding [SCR1-3 (delN195-K196)TANANKSLSSISCQT (SEQ ID NO:14)

Plasmid pBC04-29 was constructed from plasmid pDB1013-5 encoding SCR1-3 of LHR-A of CR1 (patent application WO 94/00571) by QuickChange site directed mutagenesis (Stratagene) according to the manufacture protocols. Two complementary oligonucleotides (SEQ ID No 15 and SEQ ID No 16) were used to generate a novel restriction site (silent) at G186/P187 and a C terminal cysteine. In the event the reaction produced a frame-shift mutation at position N195. In the resulting sequence the C terminal amino acids N195 and K196 are replaced with a 14 amino acid peptide TANANKSLSSISCQT (residues 196–209 of SEQ ID NO:14). Fortuitously, this sequence contains an internal cysteine close to the C terminus, preceeded by a spacer sequence of 11 amino acids.

(b) Expression of plasmid pBC04-29 encoding [SCR1-3 (delN195-K196)TANANKSLSSISCQT (SEQ ID NO:14) in *E. coli* pBC04-29 was transformed into competent *E. coli* BL21 (DE3)pLys-S and resultant colonies were isolated and checked for plasmid content. A single colony was inoculated into 10 ml LB medium (10 g/L bactotryptone, 5 g/L yeast extract, 10 g/L NaCl) containing 50 ug/ml ampicillin. The culture was grown for 6–18 hours at 37° C., 230 r.p.m. before being used to inoculate 1 liter of the same medium containing 50 ug/ml ampicillin at a dilution of 1 in 100 in 4 L erlenmeyer flasks. Cells were grows to an OD of 0.8–1.0 at $A_{609}$ nm. IPTG (isopropyl B-D galactopyranoside) was added to a final concentration of 1 mM and cells allowed to continue growth for a further 3–4 hours or overnight before harvesting by centrifugation at 8000 g/10 min. Pellet from 1L of culture was stored at −80° C.

(c) Isolation and purification of [SCR1-3(delN195-K196) TANANKSLSSISCQT (SEQ ID NO:14)

The methods are essentially those detailed in Dodd L et al. (1995) Protein Expression and Purification 6 727–736, subsequently modified as described in Example 18. Briefly, the cell pellet from 1L of culture from (b) was resuspended in buffer, sonicated and the inclusion bodies isolated by centrifugation. The inclusion bodies were resolubilised in 100 ml of fully reducing buffer and target protein purified on Macroprep High S (30 g wet weight). Product (27 ml at nominal 1.5 mg/ml) that eluted from the column in the 1M NaCl-containing buffer was refolded by dilution into 2.5 L cold 60 mM ethanolamine/1 mM EDTA, with the glutathione redox agents added at 1 h. After 3 d at 4 degrees C. the solution was ultrafiltered using a YM10 membrane and the retentate was treated with ammonium sulphate, centrifugated and the supernatant purified on Butyl Toyopearl 650M (bed volume 53 ml). A single A280 peak was eluted by the decreasing ammonium sulphate gradient. SDS PAGE under non-reducing conditions followed by protein staining revealed a major polypeptide with an apparent molecular weight of 22,000, believed to be the target protein. One of the contaminating polypeptides had as apparent weight of about 40,000, which was identified as the dimer of the monomeric form of the target by comparison with adjacent markers of [SCR1-3]-Cys. The product had as estimated protein concentration of 30 nM.

for a further 4 h at room temperature. SDS PAGE analysis showed a major band in the preparation had an apparent molecular weight of 25 000, clearly shifted from the original parent molecular weight of 23 000.

Example 21

Preparation of [SCR1-3]DGPSEILRGDFSSC (SEQ ID No. 23)

(a) Construction of plasmid pBC04-31 encoding [SCR1-3] DGPSEILRGDFSSC (SEQ ID NO:23)

Plasmid pBC04-31 was constructed using plasmid pBC04-29 (described in Example 19) and a synthetic oligonucleotide pair (SEQ ID No. 25 and SEQ ID No. 26). pBC04-29 was digested with the restriction enzymes HindIII and ApaI and the large fragment (2170 bp) isolated. The two oligonucleotides were annealed by warming to >90° C. and slowly cooling to room temperature and ligated with the DNA fragment. The ligated DNA was transformed into competent E. coli XLI-Blue. Colonies were analysed for plasmids in which the oligonucleotides had been inserted by looking for the presence of a novel AvaI site at position 2733. On digestion with AvaI pBC04-31 yielded fragments of 2311 and 495 bp. DNA from positive clones was used to transform the expression strains. The oligonucleotides inserted added the peptide sequence DGPSEILRGOFSSC (residues 198–211 of SEQ ID NO:23) to the C terminus of SCR1-3 and also repaired the frame-shift error seen in pBC04-29.

(b) Expression, isolation and purification of [SCR1-3] GDPSEILRGOFSSC (SEQ ID NO: 23)

Expression, isolation and purification of [SCR1-3] DGPSEILRGDFSSC (SEQ ID NO: 23) is carried out using pBC04-31 by procedures generally described in Example 6.

Example 22

Preparation of [SCR1-3]DGPSEILRGOFSSC-(-S-S-[MSWP-1]) (This sequence is a conjugate of SEQ ID NO:23 and the base peptide of SEQ ID NO:5).

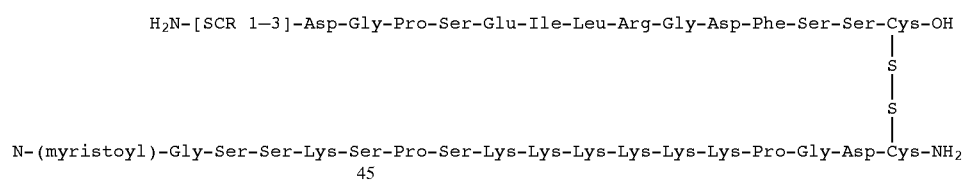

Example 20

Preparation of [SCR1-3(deln195-K196)] TNANKSLSSISCQT-(-S-S-[MSWP-1]) (This sequence is a conjugate of SEQ ID NO:14 and the base peptide of SEQ ID NO: 5).

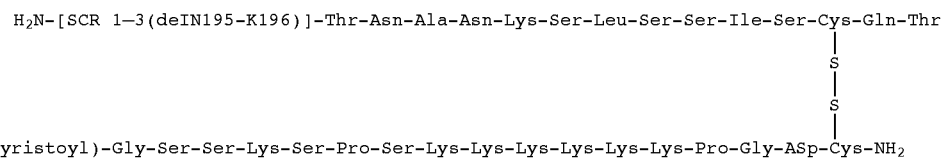

[SCR1-3(delN195-K196)TANANKSLSSISCQT (SEQ ID NO: 14) prepared as described in Example 19 (approx. 30 uM protein; 0.1 ml) was mixed with TCEP (5 nM in 50 mM Hepes pH 4.5; 0.0072 ml) and incubated at room temperature (22 degrees C.) for 15 h. 0.05 ml of this solution was mixed with 0.005 ml of 0.5M ethanolamine and 0.003 ml of 7 mM MSWP-1 (see Example 2); the solution was incubated (SCR1-3)]DGPSEILRGDFSSC (SEQ ID NO:23) protein prepared in a similar way to that described in Example 21 is reacted with MSWP-1 as described in Example 8 to give the title compound.

Example 23

Preparation of [SCR1-3]AAPSVIGFRILLLKVAGC (SEQ ID No. 33)

(a) Construction of plasmid pBC04-34 encoding [SCR1-3] AAPSIGFRILLKVAGC (SEQ ID NO:33)

Plasmid pBC04-34 was constructed using plasmid pBC04-29 (described in Example 19) and a synthetic oligonucleotide pair (SEQ ID No. 34 and SEQ ID No. 35). pBC04-29 was digested with the restriction enzymes HindIII and ApaI and the large fragment (2170 bp) isolated. The two oligonucleotides were annealed by warming to >90° C. and slowly cooling to room temperature and were ligated with the DNA fragment. The ligated DNA was transformed into competent E. coli XLI-Blue. Colonies were analysed for plasmids in which the oligonucleotides had been inserted by looking for an increase in size of the NdeI/HindIII fragment by 50 base pairs. The presence of the cysteine codon was determined by the presence of a DdeI site at position 2781. pBC04-34 digested with DdeI yielded diagnostic bands of 481 and 109 bp. DNA from positive clones was used to transform the expression strains (see next section). The oligonucleotides inserted added the peptide sequence AAPSVIGFRILLLKVAGC (SEQ ID NO: 43) to the C terminus of SCR1-3 and also repaired the frame-shift error seen in pBC04-29.

(b) Expression, isolation and purification of [SCR1-3] AAPSVIGFRILLLKVAGC (SEQ ID NO:33)

Expression, isolation and purification of [SCR1-3] AAPSVIGFRILLLKVAGC (SEQ ID NO:33) is carried out using pBC04-34 by procedures generally described in Example 6.

Example 24

Preparation of [SCR1-3] AAPSVIGFRILLLKVAGC-(-S-S-[MSWP-1]) (This sequence is a conjugate of SEQ ID NO:33 and the base peptide of SEQ ID NO:5).

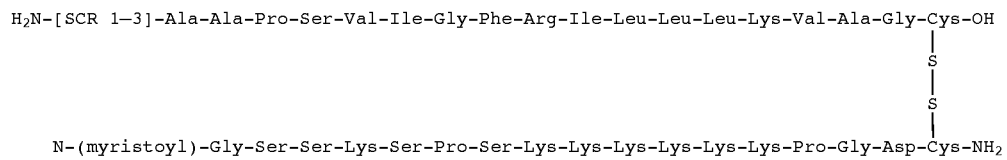

[SCR1-3]AAPSVIGFRILLLKVAGC (SEQ ID NO:33) protein prepared in a similar way to that described in Example 23 is reacted with MSWP-1 as described in Example 8.

Biological Activity (I) Anti-complement Activity Measured by the Classical Pathway-mediated Haemalysis of Sheep Erythrocyle (i) Functional activity of complement inhibition was assessed by measuring the inhibition of complement-mediated lysis of sheep erythrocytes sensitised with rabbit antibodies (Diamedix Corporation, Miami, USA). The assay is designed to be specific for the classical pathway of complement activates. Human serum diluted 1:500 or 1:400 (final concentration in assay mixture) in 0.1M Hepes/0.15M NaCl/0.1% gelatin pH 7.4 was used as a source of complement. The serum was prepared from a pool of volunteers essentially as described in Dacia & Lewis, 1975. Briefly, blood was warmed to 37° C. for 5 minutes, the clot removed and the remaining serum clarified by centrifugation. The serum fraction was split into small aliquots and stored at −196° C. or −80° c. Aliquots were thawed as required and diluted in the Hepes buffer immediately before use.

Inhibition of complement-mediated lysis of sensitised sheep erythrocytes was measured using a standard haermolytic assay using a v-bottom microtitre plate format as follows:

50 μl of a range of concentration of inhibitor diluted in Hepes buffer were mixed with 50 μl of the diluted serum and 100 μl of sensitised sheep erythrocytes and then incubated for 1 hour at 37° C. Samples were spun at 1600 rpm at ambient temperature for 3 minutes before transferring 150 μl of supernatant to a flat bottom microtitre plate and determining the absorption at 405 or 410 nm. Maximum lysis (Amax) was determined by incubating serum with erythrocytes in the absence of any inhibitor. Background lysis (Ao) was determined by incubating erythrocytes in the absence of any serum or inhibitor. Inhibition was expressed as a fraction of the total cell lysis such that IH50 represents the concentration of inhibitor required to give 50% inhibition of lysis.

% inhibition=1-[(A-Ao)/(Amax-Ao)]

| Results | |
|---|---|
| Compound | IH50 |
| WO94/00571 SEQ ID NO 27 | 0.2–0.3 ug/ml [10–15 nM] (1) |
| Example 6* | 0.65 ug/ml [30 nM] (mean of two) (2) |
| Example 7* | 0.3–1.0 ug/ml [15–50 nM] (n = 3) |
| Example 8a | 0.014 ug/ml [0.6 nM] ) |
| Example 8b | <0.001 ug/ml [<0.04 nM] ) (3) |
| Example 8c | 0.001 ug/ml [0.043 nM] ) |
| Example 8d⁺ | [0.06 nM] ) |
| Example 10a | 0.02 ug/ml [0.8 nM] |
| Example 10b | −0.01 ug/ml [−0.4 nM] |
| Example 12 | −0.0016 ug/ml [0.07 nM] |

-continued

| Results | |
|---|---|
| Compound | IH50 |
| Example 13 | −0.009 ug/ml [0.4 nM] |
| Example 14 | −1.1 ug/ml [50 nM] |
| Example 19 | [4 nM] |

*As 2-mercaptoethanol/g lutathione derivatives
⁺Assay of the two solutions and the original pre-lyophilisation solution from Example 8d.
Other IH₅₀ values generated for similar batches include:
(1) 15 nM
(2) 8 nM, 5 nM, 8 nM, 4 nM
(3) 0.3 nM, 0.2 nM, 0.07 nM, 0.06 nM, 0.2 nM, 0.4 nM, 0.5 nM, 0.6 nM.

The above data show that:

1. The complement inhibitory activities of the 'base' protein (SCR1-3 of human complement receptor 1 of WO94/00571) and its derivatives with either an additional C-terminal cysteine (SCR1-3/cys, Example 6) or a single cationic 'switch' sequence (SCR1-3/switch, Example 7) are similar.

2. However, incorporation of two membrane binding elements (electronic switch and myristoyl) by addition of MSWPs-1, 2 or 3 (which contain both elements) to SCR1-3/cys or three membrane binding elements by addition of the MSWP-1 to the SCR1-3/switch construct results in products which are significantly more potent (~20–200x) than the base or single membrane binding element proteins. The use of TCTP-1 which is targeted to membrane elements found in CD3-positive cells and not to erythrocyte membranes gave a conjugate of similar potency is SCR1-3 derivatives with no or single membrane addresses. Thus, the increases is potency in an assay which depends on an erythrocyte membrane event (cytolysis by the membrane attack complex of complement) can be attributed to membrane targeting of the cytolysis inhibitor proteins by the combination of two membrane binding elements.

(II) Assay of Anti-complement Activity in the Classical Pathway Haermolytic Assay: activity in the sera of domestic pig, guinea pig, rat and marmoset.

The activity of [SCR1-3]-Cys-S-S-[MSWP-1] was examined in the classical pathway haermolytic assay using the sera of pig, guinea pig, rat or marmoset. The methodology was essentially as described in (I) with minor modifications, for example small changes to the concentration of serum used. [SCR1-3]-Cys-S-S-[MSWP-1] was prepared essentially as described in Example 8c. The IH50 values for the different sera were: pig, 0.2 nM; guinea pig, 0.3 nM; rat, 0.4 nM; marmoset, 0.2 nM. These results show that [SCR1-3]-Cys-S-S-[MSWP-1] is capable of inhibiting classical pathway complement inhibition in the sera of a variety of animal species.

(II) Anti-complement Activity Measured by Alternative Pathway-mediated Haemolysis of Guinea Pig Erythrocyle Functional activity of complement inhibitors was assessed by measuring the inhibition of complement mediated lysis of guinea pig erythrocytes essentially as described by Scesney, S. M. et al (1996) J. Immunol, 26 1729–1735. The assay is designed to be specific for the alternative pathway of complement activation. Human serum prepared from a pool of volunteers essentially as described in Dacie & Lewis, 1975 was used as the source of complement. Briefly, blood was warmed to 37° C. for 5 minutes, the clot removed and the remaining serum clarified by centrifugation. The serum fraction was split into small aliquots and stored at –196° C. or –80° C. Aliquots were thawed as required and diluted in 0.1M Hepes/0.15M NaCl/0.1% gelatin/8 mM EGTA/5 mM $MgCl_2$ pH 7.4 (buffer A) immediately before use. Guinea pig erythrocytes were prepared from guinea pig whole blood collected into EDTA-coated tubes as follows. The blood was span at 1600 rpm for 5 min and the erythrocyte pellet washed 3 times with 0.1M Hepes/0.15M NaCl/0.1% gelatin pH 7.4 until the supernatant of the spin was essentially colourless. The erythrocytes were finally resuspended to the original volume of blood used and were stored at +4 degrees C. they were used within 2 weeks.

50 $\mu$l of a range of concentrations of inhibitor diluted in buffer A is a v-bottom microtitre plate were mixed with, first, 100 $\mu$l of serum that had been diluted 1:3 and second, 50 $\mu$l of guinea pig erythrocytes (diluted 1:49 in buffer A) and incubated for 1 hour at 37° C. The plan was span at 1600 rpm for 3 minutes before transferring 150 $\mu$l of each supernatant to a flat bottom microtitre plate and determining the absorption at 405 nm, which reflects the amount of lysis in each test solution. Maximum lysis (Amax) was determined by incubating serum with erythrocytes in the absence of any inhibitor. Background lysis (Ao) was determined by incubating erythrocytes in the absence of any serum or inhibitor. The final dilution of serum used in the assay did absorb at 405 cm but the level of absorbance (approx 10% of Amax) was considered to have a neglible affect on the overall assay results and it was ignored in the calculations. Inhibition was expressed as a fraction of the total cell lysis such that IH50 represents the concentration of inhibitor required to give 50% inhibition of lysis.

$$\% \text{ inhibition}=1-[(A-Ao)/(Amax-Ao)]$$

Results

Two aliquots (one lyophilised and resolubilised in a neutral buffer, the other not lyophilised) of a single batch of o([SCR1-3]-Cys-S-S-[MSWF-1] prepared in a similar way to that described in Example 8 (c) were tested in the haermolytic assay. The IH50 values for the compounds were:

| | |
|---|---|
| [SCR1-3]-Cys-S-S-[MSWP-1] (not lyoph) | 310 nM |
| [SCR1-3]-Cys-S-S-[MSWP-1] (lyoph) | 480 nM |

The result shows that [SCR1-3]-Cys-S-S-[MSWP-1] exhibited activity against the alternative pathway of the complement system and that lyophilisation and subsequent resolubilisation of the protein had no affect (within experimental error) on the biological activity of the protein.

(III) Plasminogen Activator Assay (j) SK-related molecules from Example 16 were assayed using a plasminogen activation assay. A solution of purified human $Lys_n$-Plasminogen (1 uM in PST buffer containing 25% v/v glycerol [PSTG buffer], 0.5 ml) was incubated with thiolated SK (final concentration 0.1 to 1.07 nM) for 1 h at 25° C. An aliquot of this mixture (10 ul) was incubated with 1.0 mM of the plasmin substrate S-2251 (H-D-Val-Leu-Lys-p-nitroanilide, KabiVitrum, Stockholm, Sweden) in 0.1M Triethanolamine HCl pH 8.0 (0.5 ml) at 25° C. The release of p-nitroaniline was monitored continuously at 405 nm. Under these conditions, one substrate unit (SU) of plasmin activity is defined as the amount of enzyme giving an increase in optical density at 405 nm of 0.001 $min^{-1}$. Under these conditions thiolated SK (1 nM), generated plasmin at a nearly linear of 4225 SU/ml.

SK-MSWP-1 conjugate was diluted 1:100 in PSTG buffer and 5–50 ml aliquots tested in the plasminogen activation assay. The stock preparation was found to contain approximately 2.9 uM functional SK.

(II) The potential activity of the acyl-enzyme preparations of Example 17 was estimated by dilution 25–50 fold into PST buffer and incubation for 2 h at 37° C., followed by assay using 2 mM (S-2288 (H-D-Ila-Pro-Arg-p-nitroanilide 2HCl) under the same conditions used in (i) above. Under these conditions, the potential activity of the reduced PDAEB->tPA preparation was 2760 SU/ml and that of the MSWP/1/PDAEB->tPA conjugate 535 SU/ml.

(IV) Erythrocyte Binding Assays (i) Erythrocyte aggregation test for modified and unmodified Rabbit anti-(human erythrocyte membrane) antibody.

Human pooled erythrocytes (Ortho A2, Raritan, N.J. 3% v/v, 50 ml) were added to microtitre plates wells and either unmodified rabbit anti-(human erythrocyte membrane) antibody [RAEM] or RAEM-MSWP1 conjugate from Example 15 added at concentrations expressed relative to undiluted stock RAEM. Cells agitated at –100 rpm for 40 min at 25° C. 5 ul was removed from each well and examined by light microscopy at ×20 magnification. A visual scoring scale was used as follows:

| Results | | | |
|---|---|---|---|
| Control (n = 6) | − | RAEM-MSWP1 1/3900 | +/− |
| RAEM 1/1100 | − | RAEM-MSWP1 1/1000 | +/− |
| RAEM 1/600 | − | | |
| RAEM 1/350 | +/− | RAEM-MSWP1 1/357 | +++ |
| RAEM 1/50 | ++ | RAEM-MSWP1 1/62 | +++ |

− No clumping, cells moving freely relative to each other.
+ Small clumps (<10 cells)
++ Larger clumps (100 plus cells)
+++ Very large visible aggregates Conclusion The antibody preparation modified to contain a membrane-binding unit was more effective at inducing aggregation of cells because binding to the cell membrane through MSWP1 allowed a higher effective concentration of bridging antibody on the membrane surface.

(II) Binding of 125-Iodine-[SCR1-3]-Cys-S-S-[MSWP-1] to Human Erythrocytes

[SCR1-3]-Cys-S-S-[MSWP-1] (2 mg/ml in PBS; 0.25 ml) was mixed with 0.5 mCl of 125-Iodine (Amersham) in the presence of 9 moles potassium iodide following the Iodogen procedure and reagents (Pierce and Warriner (UK) Ltd.). The labelling was allowed to proceed for 20 min at room temperature, the reaction was quenched with 0.1 ml of 1M potassium iodide and the solution buffer-exchanged into PS/0.1% albumin. Citrated blood collected from a healthy volunteer was used as a source of human erythrocytes. Blood (0.2 ml) was mixed with 10 microlitres of appropriately diluted 125-Iodine-[SCR1-3]-Cys-S-S-[MSWP-1] (final concentration 700 pM) and incubated for 30 min at 37 degrees C. The erythrocytes were then isolated by three repeat washings in PSB/centrifugation steps and samples counted in a Wallac 1470 Wizard gamma counter. The results were as follows:

| | cpan |
|---|---|
| 1st wash | 3600000 |
| 1st pellet | 140000 |
| 2nd wash | 52000 |
| 3rd wash | 6500 |
| final pellet | 26000 |

Using values of $5 \times 10^9$ erythrocytes per ml of blood and and a specific radioactivity of $2.7 \times 10^7$ cpm/nmole for the [SCR1-3]-Cys-S-S-[MSWP-1] it was calculated that about 600 molecules of [SCR1-3]-Cys-S-S-[MSWF-1] bound per cell (the values for 'final pellet').

(III) Binding of Fluoruresin-labelled-[SCR1-3]-Cys-S-S-[MSWF-1] to Human Erythrocytes

[SCR1-3]-cys (prepared in a similar way to that described in Example 18) (45 uM, 1.0mg/ml in 0.1M sodium phosphate, approx. 0.2M ammonium sulphate pH 7.0) was partially reduced by incubation at 25° C. for 18 h by the addition of a 4-molar excess of Tris(2-carboxyethyl) phosphine (TCEP; Pierce & Warriner (UK) Ltd.). The solution was buffer exchanged into 50 mM Hepes pH7.0; post buffer exchange the protein concentration was 22 uM. The partially reduced [SCR1-3]-cys was incubated with a 4-fold molar excess of 6-(fluorescein-5-carboxamide) hexanoic acid, succinimidyl ester (Molecular Probes Inc. USA) and incubated for 1 h at 4° C. the excess fluorescent label was removed by buffer exchange of the protein solution into 50 mM Hepes pH7.0. Fluorescein-[SCR1-3]-cys-S-S-[MSWP-1] was synthesized by adding MSWP-1 (Example 2) to give a five-fold molar excess over fluorescein labelled protein and was incubated for 4 h at 25° C. The solution was buffered exchanged into PBS and this solution was used for the microscopy studies.

[SCR1-3], 10 mg/ml in 50 mM f rmic acid, was mixed in a 1:10 ratio with 50 mM NaHCO$_3$ pH8.5; the pH of the solution was adjusted with NaOH to pH9.5. The fluorescein was extracted from Celite-fluorescein isothiocyanate (Celite:fluorescein; 1:10, Sigma) by DMSO in a 1:4 (w/v) ratio. The fluorescein-DMSO solution was added to the protein solution in a 1:14 ratio and incubated for 1 h at RT. Excess label was removed by gel filtration into PBS containing 0.01% Tween-80 and this solution was used for microscopy studies.

Citrated blood was collected from a healthy volunteer and the erythrocytes isolated, washed in PBS and diluted 250-fold compared to the original blood volume. 0.05 ml of erythrocytes were incubated with 2 nM fluorescein-[SCR1-3]-cys-S-S-[MSWP-1] or 2 nM fluorescein-[SCR1-3] and incubated for 30 min at 37° C. An eight microliter sample of each incubation was mounted on a slide and viewed on an inverted confocal microscope (Biorad). The cells incubated with fluorescein-[SCR1-3] showed no specific staining whereas with those incubated with fluorescein-[SCR1-3]-cys-S-S-[MSWP-1] staining appeared diffusely over the cell surface and also intensely stained patches were visible on the cell membrane. No labelling was seen intracellularly.

(iv) Binding of MSWP-1/PDAEB→tPA to human erythrocytes

Human trypsinized and glutaraldehyde-treated red blood cells (1.0 ml of a 4% suspension) was pelleted by low-speed centrifugation and resuspended is a total volume of 0.5 ml PST containing either no addition or approximately 270 SU of either reduced PDEAB→tPA or MSWP-1/PDAEB→tPA conjugate of Example 17. The mixtures were incubated by gentle rolling for 5 min at 23° C. and then the cells were pelleted by centrifugation followed by two washes with 1.0 ml PST buffer. Finally, the cells were suspended in 0.5 ml PST and incubated at 37° C. Samples of the supernatant (100 ul) were removed after pelleting. Assay using S-2288 (as above) showed that after 2 h, approximately 7% of the applied t-PA activity was present in the supernatant of cells exposed to MSWP-1/PDAEB→tPA whereas only −2.8% was present in the supernatant of cells exposed to reduced PDAEB→tPA alone. No t-PA amidolytic activity was detected in controls.

This experiment suggests that reversible linkage of the active site of t-PA to MSWP-1 increases the tendency of this enzyme to bind to red blood cells.

(v) Localisation fSK-MSWP-1 conjugate on the surface of human erythrocytes

A stabilised preparation of human erythrocytes (trypsinized, glutaraldehyde-treated, Sigma, Gillingham, UK, 4% v/v, 0.4 ml) was pelleted by centrifugation (−2000 g/2 min) and resuspended in 0.4 ml PST buffer with either 0.1 uM thiolated SK or 0.1 uM SK-MSWP-1 from Example 16.

The suspensions were incubated for 30 min at 37° C. and then washed by two cycles of centrifugation and resuspension in PST buffer. Finally, they were resuspended in PSTG buffer (0.4 ml) containing 1 uM plasminogen and incubated and assayed for plasmin as described above.

The control thiolated-SK generated plasmin at a rate of 522 SU/ml, while the SK-MSWP-1 conjugate produced 6184 SU/ml. The latter activity corresponds to around 2100 thiolated SK molecules/cell.

(vi) Binding of [SCR1-3]-Cys-S-S-[MSWP-1] to human erythrocyte membranes

4×2.0 ml of trypsinized, glutaraldehyde-treated human erythrocytes (Sigma, R0127) were centrifuged for 2 min at about 3000 rpm. The supernatants were discarded and the cells resuspended in phosphate/saline/Tween (0.01%) (PST) (1 ml per tube) and [SCR1-3]-Cys-S-S-[MSWP-1] of Example 8 was added to a final concentration of 20 ug/ml to three of the tubes. The mixtures were then incubated at 37 degrees C. for 30 min., then washed five times by repeat centrifugation and washing in PST. The cells were finally suspended in 1 ml PST and were held at 4 degrees C.

The ability of these cells to inhibit complement-mediated lysis of sheep erythrocytes was measured using the standard classical pathway complement inhibition assay described in (I) above. The human erythrocytes were added to the assay at four different dilutions, followed by the human serum and then the sheep red blood cells and incubation at 37 degrees C. as usual. The % inhibition data are shown below.

| Final dilution | human erythrocytes, untreated | human erythrocytes, treated with [SCR1-3]-Cys-S-S-[MSWP1] |
|---|---|---|
| 1/4 | 22% | 62% |
| 1/16 | −8% | 88% |
| 1/256 | 5% | 74% |
| 1/2500 | −7% | 51% |

Thus the percentage inhibition for the [SCR1-3]-Cys-S-S-[MSWP-1]-treated cells at maximum dilution was significantly higher than the untreated cells at ¼ dilution. The [SCR1-3]-Cys-S-S-[MSWP-1]-treated cells, therefore, contained at least 500-fold more complement inhibitory activity than the untreated cells, even though the cells had been washed extensively to remove any non-bound [SCR1-3]-Cys-S-S-[MSWP-1].

The following methods and examples further illustrate aspects of the invention.

Introduction of DNA into *E. coli*

Plasmids were transformed into *E. coli* XL1-Blue (Stratagene), HMS174(DE3) (Novagen, UK) or UT5600 (DE3) (see below) that had been made competent using calcium chloride as described in Sambrook et al, (op.cit.). UT5600 was purchased from New England Biolabs (#801-I) and was converted to a DE3 lysogen. UT5600 was isolated as a mutant of K12 strain RW193 (itself derived from AB1515) which was insensitive to colicin-B (McIntosh et al. (1979) J.Bact. 137 p653). It was not initially known that ompT had been lost, but further work by the same group showed that protein α (now OmpT) was lacking (Earhart et al (1979) FEMS Micro Letts 6 p277). The nature of the mutation was determined to be a large deletion (Elish et al (1988) J Gen Micro 134 1355).

DNA sequencing

DNA sequencing was contracted out to Lark (Saffron Walden, Essex UK) or MWG (Milton Keynes, UK).

Production of oligonucleotides

Oligonucleotides were purchased from Cruachern (UK) or Genosys-Sigma (Pampisford, Cambridgeshire UK)

Polymerase chain reaction amplification of DNA

Purified DNA or DNA fragments from ligation reactions or DNA fragments excised and purified from agarose gels were amplified by PCR from two primers complementary to the 5' ends of the DNA fragment. Approximately 0.1–1 mg of DNA was mixed with commercially available buffers for PCR amplification such as 10 mM Tris pH 8.3 (at 25° C.), 50 mM KCl, 0.1% gelatin; $MgCl_2$ concentrations were varied from 1.5 mM to 6 mM to find a suitable concentration for each reaction. Oligonucleotide primers were added to a final concentration of 2 mM; each dNTP was added to a final concentration of 0.2 mM. 1 unit of Taq DNA polymerase was then added to the reaction mixture (purchased from a commercial source, e.g. Gibco). The final reaction volume varied from 20 ml to 100 ml, which was overlayed with mineral oil to prevent evaporation. Thermal cycling was then started in a thermal cycler such as the PCR machine from MJ Research. A typical example of conditions used was 94° C. for 5 minute, 55° C. for 1 minute, and 72° C. for 2 minutes; however, the optimal temperatures for cycling can be determined empirically by workers skilled in the art. The DNA fragment was amplified by repeating this temperature cycle for a number of times, typically 30 times.

pET15b vector for DAF expression

The pET15b expression vector is a T7 promotor based vector available commercially through Novagen (Wisconsin, USA). Briefly, the vector carries the following features which make it a useful vehicle for the expression of heterologous proteins in *E. coli;* a selectable antibiotic marker (β-lactamase) conferring ampicillin resistance, a copy of the laci gene providing lac repression in strains of *E. coli* that are laci', and the T7-lac promoter. The T7-lac promoter combines the T7 RNA polymerase promoter sequences with the laci repressor binding site from the *E. coli* lactose operon. This reduces expression of the cloned gene in the absence of the inducer isopropyl β-D thiogalactopyranoside (IPTG). Downstream of the T7 promoter is a multiple cloning site built into a region of sequence which codes for a polyhistidine tag sequence. Translation initiates at the methionine codon at position 332–330 of the vector sequence and proceeds counter-clockwise to yield the following peptide: MGSSHHHHHHSSGLVPRGSH (SEQ ID NO: 48). The six histidine residues allow for purification of the fusion protein by metal chelation chromatography, whilst the GLPVR (amino acids 13–17 of SEQ ID NO: 48) motif constitutes a thrombin cleavage site for removal of the peptide from the fusion protein after purification. Three restriction enzyme sites are provided for the insertion of cloned DNA in-frame with the polyhistidine leader. These are Ndel (CATATG), Xhol (CTCGAG) and BamHi (GGATCC). Use of the Ndel site to overlap the methionine initiation codon of the cloned gene removes the possibility of unwanted amino acids at the N-terminus of the fusion protein. At the 3' end of the multiple cloning site is the T7 transcriptional terminator.

Colorimetric determination of protein concentration

Protein concentration determination utilised a colorometric method utilising Coomassie Plus Protein Assay Reagent (Pierce Chemical Company) according to the manufacturer's instruction. The assay used a reference standard of the protein of Example 6.

Identification of proteins by Western blot

For certain procedures, it is necessary to characterise the expression of recombinant proteins by an immunological method termed a Western blot. In this method, proteins to be analysed are separated by SDS-PAGE, transferred to a protein binding membrane such as polyvinylidene difluoride (PVDF), and then probed with an antibody that is specific for the target protein. Typically, the binding of the first antibody is detected by the addition of an enzyme-labelled secondary antibody and an appropriate solution which contains a chromogenic substrate. One procedure for the transfer of proteins to a protein-binding membrane was as follows. After SDS-PAGE, the proteins on the gel were transferred by electrotransfer to a protein-binding surface such PVDF. In this procedure, two sheets of filter paper (3M, Whatman) soaked in 0.3M Tris, 10% (v/v) methanol, pH10.4, were placed on the anode of an electroblotter (Semi-dry blotter, Biorad). These filter papers were then overlayed by a further two sheets of filter paper soaked in 25 mM Tris, 10% (v/v) methanol, pH10.4. On top of this stack of filter papers was placed a sheet of PVDF membrane which had been pre-wetted in methanol and then soaked in a buffer that comprises 25 mM Tris, 10% (v/v) methanol, pH10.4. The SDS-PAGE gel was then placed on the top of the PVDF membrane, and overlayed with two sheets of filter paper soaked in 25 mM Tris, 192 mM 6-amino-n-caproic acid, 10% (v/v) methanol. The cathode of the electroblotter was then placed on top of the stack of filter papers, gel and membrane, and the proteins transferred by passing a current between the electrodes at 15V for 30 minutes. Subsequent steps for the detection of the transferred proteins were described in the Novex WesternBreeze System (Invitrogen). For the detection of human CD59, a rat anti-CD59 monoclonal antibody YTH53.1 (Davies et al., *J. Exp. Med.* 170, 637, 1989) was used together with an enzyme-labeled anti-rat secondary antibody. For the identification of His-tagged DAF, an anti his-tag monoclonal antibody was used.

Purification of CD59 from human urine

Urine was collected into 10 mM sodium azide/5 mM benzamidine over approximately 48 hrs. The urine was then passed through a fluted coarse filter to remove aggregates. The urine was then concentrated to approximately 150 mls in a Pellicon concentrator fitted with a membrane cassette with a 10 kDa MW cut-off membrane. Insoluble material was removed by centrifugation at 10000×g for 30 minutes. The supernatant was then applied to a CNBr-activated Sepharose 4B affinity column prepared with the rat monoclonal anti-CD59 antibody YTH 53.1 (Davies et al. *J. Exp. Med.* 170, 637, 1989). The column was washed overnight with 1M NaCl and bound material eluted with 4M $MgCl_2$. The protein content of each 1 ml fraction eluted from the column was determined by measuring absorbance at OD280 nm. The fractions containing the most protein were then pooled and dialysed through a 10 kDa MW cut off membrane into a solution containing 0.9% NaCl, and then dialysed by a similar procedure into PBS. The dialysed protein was then concentrated using a stirred cell ultrafiltration device (Amicon) fitted with a 10 kDa MW cut-off membrane. The material may be further purified by gel filtration in 10 mM Hepes, 140 mM NaCl, pH7.4, on a Superdex S-75 fast protein liquid chromatography system (Pharmacia) or Sephadex G-75. This method gave a yield of around 7 mg pure protein from 20L urine.

Expression and purification of recombinant soluble CD59 from CHO cells

Soluble CD59 was expressed in a recombinant form from Chinese Hamster Ovary cells as follows. Briefly, the polymerase chain reaction was used to produce a truncated cDNA encoding soluble CD59 from a full length cDNA (Davies et al. *J. Exp. Med.* 170, 637, 1989). A mutation was introduced into the cDNA at codon 18 of the mature protein which changed the Asn codon for Ala. The procedure for this site-directed mutagenesis can be performed by a number of methods including the Quickchange mutagenesis kit (Stratagene). To introduce the modified gene into the CHO expression plasmid pDR2EF1alpha, the polymerase chain reaction was used with two oligonucleotides; the first oligonucleotide was complementary to the first seven codons at the N-terminus of the mature CD59 protein; and the 3' oligonucleotides introduces a termination codon immediately following the codon for Asn-70 of the CD59 cDNA. These oligonucleotides were also designed to contain recognition sequences for restriction enconucleases compatible with the polylinker site of the CHO expression vector. The DNA fragment resulting from the PCR amplification was ligated into a CHO expression vector and this plasmid transfected with calcium phosphate into CHO cells. Cells that had become stably transfected were selected from untransfected cells by growth in medium that contained the antibiotic hygromycin. Individual transformants were picked and for each clone the expression of CD59 was analysed by ELISA. The highest expressing clone was chosen for large-scale production of CD59 using a variety of techniques including the use of cell factories (Nunc).

To purify the CD59, the culture medium was precleared by centrifugation at 10000×g for 30 minutes. The soluble CD59 was then purified using an immunoaffinity column containing the monoclonal antibody YTH53.1 (Davies et al. *J. Exp. Med.* 170, 637, 1989), as described above. The protein was then stored in PBS at concentrations of up to 5 mg/mL at −70° C.

Preparation of C56 euglobulin

C56 euglobulin was an essential reagent that was used for the C5b6-initiated reactive lysis of erythrocytes. C56 euglobulin can be generated in and purifed from some acute-phase sera from post-trauma individuals (such as sports injuries, surgery or childbirth). Blood was drawn from donors in the acute phase of inflammation and allowed to clot at room temperature. To each 10 mls of serum, 0.5 mls of yeast suspension was added and the mixture incubated overnight on a rotator at room temperature. The serum was centrifuged to remove the yeast and dialysed against 0.02M Na/K phosphate, pH 5.4. The precipitate (containing the C56 euglobulin) was collected by centrifugation and redisolved in 0.01M Na/K phosphate/0.05M NaCl, pH7.0 containing 25% v/v glycerol.

C5b6-initiated reactive lysis of erythrocytes

Guinea pig erythrocytes (TCS Microbiological, UK) were washed twice in PBS and resuspended to 5% by volume in PBS/0.05% CHAPS. 50 ml of these cells were placed in the wells of a round-bottomed microtiter plate. Samples to be tested were diluted in PBS/0.05% CHAPS and 50 ml of these test solutions added to the wells containing the guinea pig erythrocytes. The plate was then incubated at 37° C. for 20 minutes to allow binding of the samples to be erythrocytes. The microtitre plates were then centrifuged at 1000 rpm for 5 minutes to pellet the cells using a benchtop centrifuge. The supernatants were removed and the cell pellets resuspended in 50 ml PBS/10 mM EDTA. To this cell suspension was added 10 ml of a C56 euglobulin solution that varied in concentration in different experiments from between 1:50 to 1:500 dilution in PBS/10 mM EDTA. This solution was mixed with the cells by placing the microtitre plate on a microtitre plate shaker for 2 minutes. To this solution was then added a 90 ml of a dilution of normal human serum (from 1:50 to 1:500 in PBS/10 mM EDTA). The solutions were mixed by placing the microtitre plate on a plate shaker for a further 2 minutes. The plate was then incubated at 37° C. for 30 minutes. To determine the degree of haemolysis, the plate was then placed in a benchtop centrifuge and spun at 1800 rpm for 3 minutes. 100 ml of the supernatant was transferred to a clear flat bottomed microtitre plate and the absorbane at 410 nm measured spectroscopically. As controls, guinea pig erythrocytes were treated in an identical manner to the test samples with the following exceptions. In the first stage of the assay, the control samples were incubated with 50 ml of PBS/10 mM EDTA for 20 minutes at 37° C. After centrifugation, a spontaneous lysis control was prepared by resuspending the cells in 150 ml PBS/10 mM EDTA; by contrast, for the maximum lysis control, the cells were resuspended in 150 ml water.

Brief Overview of Examples 25 to 36

Example 25

Synthesis and characterization of a membrane-targeted derivative of soluble human urinary CD59 (APT632).

Example 26

Synthesis and characterization of a membrane-targeted derivative of human recombinant soluble CD59 (APT637).

Example 27

An alternative Method for the production of urinary (APT2047) and recombinant (APT2059) human CD59 membrane-targeted derivatives using linkage through protein carbohydrate.

Example 28

A method for the preparation of recombinant human CD59 with a C-terminal cysteine, expressed in yeast (APT633).

Example 29

A method for the preparation of recombinant human CD59 with a C-terminal cysteine, expressed in E. coli (APT635).

Example 30

A method for the preparation of recombinant human CD59 with a C-terminal cysteine, expressed in baculovirus/insect cells (APT2060).

Example 31

A method for the preparation of recombinant human CD59 with a C-terminal cysteine, expressed in Chinese hamster ovary cells (APT2061).

Example 32

A Method for the conjugation of the membrane-localising agent APT542 to APT633, APT635, APT2060 or APT2061.

Example 33

Synthesis and characterization of APT2057 (Human DAF short consensus repeats 2–4).

Example 34

Synthesis and characterization of APT2058 (Human DAF short consensus repeats 1–4).

Example 35

Synthesis and characterization of APT2160 (APT2058 derivatized with APT542).

Example 36

Synthesis and characterization of APT2184 (APT2057 derivatized with APT542).

Example 25

Synthesis and Characterization of Urine-derived CD59 linked to MSWP-1 (APT632)

APT632 was synthesized in two steps from soluble CD59 isolated from human urine (APT631; SEQ. ID NO: 37) as described in Methods. APT631 in PBS (200 µL of a 1.9 mg/mL solution) was mixed with 2-iminothiolane (2 µL of a 100 mM solution) and the mixture incubated at room temperature for 30 minutes. The solution was then dialysed into PBS to remove unreacted 2-iminothiolane, and a solution of tris-2-carboxyethyl phosphine (4 µL of a 10 mM solution in 10 mM Hepes, pH7.4) added, and the mixture left overnight at room temperature. To this solution, 10 µL of APT542 (MSWP-1; 21 mM in dimethyl sulphoxide; SEQ. ID NO. 38) was added and incubated at room temperature for 2 h. The product APT632 was characterized by the appearance of a protein species that migrated at approximately 21 kDa as analysed by SDS-PAGE. A reactive lysis assay (described in Methods) demonstrated that APT632, at concentrations greater than 0.5 nM, protected guinea pig erythrocytes from complement-mediated lysis by a 1:100 dilution of human serum; by contrast, no significant protection from lysis was observed with the unmodified form (APT631).

Example 26

Synthesis and Characterization of Recombinant CD59 Produced in CHO Cells Linked to MSWP-1 (APT637)

APT637 was synthesized in two steps from soluble human CD59 that is expressed in a recombinant form from chinese hamster ovary cells (APT634; SEQ ID NO: 39). APT634 in PBS (200 µL of a 300 µM solution) was mixed with 2-iminothiolane (6 µL of a 10 mM solution) and the mixture incubated at room temperature for 30 minutes. The solution was then dialysed into PBS to remove unreacted 2-iminothiolane, and a solution of tris-2-carboxyethyl phosphone (4 µL of a 10 mM solution in 10 mM Hepes, pH7.4) added, and the mixture left overnight at room temperature. To this solution, 10 µL of APT542 (21 mM in dimethyl sulphoxide) was added and incubated at room temperature for 2 h. The product APT637 was characterized by the appearance of a protein species which migrated at approximately 10 kDa as analysed by SDS-PAGE as described in methods. A reactive lysis assay (described in Methods) demonstrated that APT637, at concentrations greater than 0.5 nM, protected guinea pig erythrocytes from complement-mediated lysis by a 1:100 dilution of human serum; by contrast, no significant protection from lysis was observed with the unmodified form (APT634).

Example 27

A Method for the Production of CD59 Derivatives Linked to MSWP-1 via a Carbohydrate Linkage (APT2047 and APT2059)

APT2047 is a conjugate of APT634 (SEQ ID NO: 39) and APT542 (SEQ ID NO: 38). and APT2059 is a conjugate of APT631 (SEQ ID NO: 37) and APT542, in which the linkage of each pair of compounds is through a modified carbohydrate moiety on the CD59 protein. APT2047 and APT2059 are synthesized in three steps from APT634 or APT631. The first step involves the reaction of the proteins APT634 or APT631 at a concentration of 1 mg/ml with 10 mM sodium periodate for 1 h in the dark, in a solution of 0.1M sodium acetate, pH5.5 To this mixture is added glycerol to a final concentration of 15 mM and the solution placed on ice for 5 minutes. The mixture is then dialysed into 0.1M sodium acetate, pH5.5 to remove excess sodium periodate and glycerol. In the second step, the sodium periodate-treated proteins are reacted with a solution of (4-[4-N-maleimidophenyl]butyric acid hydrazide hydrochloride (MPBH) at a final concentration of 1 mg/ml for 2 h with stirring. After this procedure, unreacted MPBH is removed by dialysis into a solution of 0.1M phosphate, pH7.0, 50 mM NaCl. In the third step of the synthesis, the proteins treated with MPBH are reacted with a solution comprising a 5-fold molar excess of APT544 to CD59 for 2 h at room temperature to generate APT2047 and APT2059. The synthesis of these proteins is confirmed by the appearance of a novel proteinaceous species that migrates at approximately 10 kDa or 20 kDa by SDS-PAGE under non-reducing conditions, respectively. In addition, these proteins protect guinea pig erythrocytes from complement-mediated lysis by human serum at a concentration greater than 0.5 nM.

Example 28

A Method for the Preparation of Recombinant Human CD59 with a C-terminal Cysteine, Expressed in Yeast (APT633)

APT633 is a protein that comprises soluble human CD59 and a C-terminal cysteine residue following position 81 of the mature CD59 protein. The protein was expressed in a recombinant form in *Pichia pastoris* cells. The polymerase chain reaction was used to produce a truncated cDNA encoding soluble CD59 from a full length cDNA (Davies et al. *J. Exp. Med.* 170, 637, 1989). The 5' oligonucleotide was complementary to 20 bases of the first 7 codons at the N-terminus of the nature CD59 protein, and the 3' oligonucleotide introduced a cysteine codon and a termination codon immediately following the codon for Ser-81 of the mature CD59 protein. These oligonucleotides were also designed to contain recognition sequences for restriction endonucleases XhoI and EcoRI which are compatible with the polylinker site of the vector pUCP1C (a derivative of pUC19 that contains the alpha-factor leader sequence and multiple cloning site from pPIC9K (Invitrogen). The DNA fragment resulting from the PCR amplification was then ligated into pUCPIC DNA and transformed into the XL1-Blue strain of *E. coli* (Stratagene). The transfected cells are selected by growth on a petri dish containing LB medium (Sigma) supplemented with ampicillin at a concentration of 100 micrograms/ml (LBAMP). The DNA from single colonies was isolated and sequenced as described in Methods. The DNA that encodes the alpha factor and CD59 was then subcloned into the vector pPIC9K that had been digested with the restriction endonucleases BamHI and EcoRI. Purified DNA from the resulting plasmid was linearised with the restriction endonuclease PmeI for transformation into *P. pastoris* strain GS115 (Invitrogen) by spheroplasting according to the manufacturer's instructions. After preliminary selection for clones that are capable of growth on a minimal RD medium (1M sorbitol, 2% w/v dextrose, 1.34% yeast nitroen base, $4 \times 10^{-5}$% biotin, 0.005% amino acids) lacking histidine. Clones having undergone multiple integration events were then selected by resistance to the antibiotic geneticin sulphate (G418). Clones that were capable of growth in medium containing G418 at a concentration of 2 mg/mL were screened for expression of CD59. Individual colonies were inoculated in 10 mL BMG medium (100 mM potassium phosphate, pH6.0, 13.4 mg/mL yeast nitrogen base, 0.4 mg/L biotin, 1% (w/v) glycerol) and grown at 30° C. with shaking until clones reached an optical density of 6 as measured spectroscopically at a wavelength of 600 nm. The cultures were then transferred to BMM medium (100 mM potassium phosphate, pH6.0, 13.4 g/L yeast nitrogen base, 0.4 mg/L biotin, 0.5% methanol) and grown for 48 h at 30° C. with shaking. Culture supernatants were then analysed by SDS-PAGE and Western blot for the presence of APT633 which was observed as a novel proteinaceous species which migrated at approximately 8000 Da.

Example 29

A Method for the Preparation of Recombinant Human CD59 with a C-terminal Cysteine, Expressed in *E. coli* (APT635; SEQ ID NO: 41)

APT635 is a protein that comprises soluble human CD59 and a C-terminal cysteine residue following codon 81 of the mature CD59 protein (SEQ ID NO: 41). The protein is expressed in a recombinant form in *E. coli* cells. The polymerase chain reaction was used to produce a truncated cDNA encoding soluble CD59 from a full length cDNA (Davies et al. *J. Exp. Med.* 170, 637, 1989). The 5' oligonucleotide was complementary to 20 bases of the first 7 codons at the N-terminus of the mature CD59 protein, and the 3' oligonucleotide introduced a cysteine codon and a termination codon immediately following the codon for Ser-81 of the mature CD59 protein. These oligonucleotides were also designed to contain recognition sequences for restriction endonucleases compatible with the polylinker site of pBROC413 (described in WO 94/00571). The DNA fragment resulting from the PCR amplification was then ligated into pBROC413 DNA and transformed into the UT5600(DE3) strain of *E. coli* (described in Methods). The transfected cells are selected by growth on a petri dish containing LB medium (Sigma) supplemented with ampicillin at a concentration of 100 micrograms/ml (LBAMP). The DNA from single colonies was isolated and sequenced as described in Methods. A single colony representing UT5600(DE3) cells transfected by DNA encoding APT635 was then grown with shaking overnight at 37° C. in LBAMP. This overnight culture was then diluted 1:100 in LBAMP medium and grown with shaking at 37° C. until the culture reached an optical density of 1.0 as determined by absorbance at a wavelength of 600 nm. To this culture was added a solution of isopropyl beta-D-thiogalactopyranoside to a final concentration of 1 mM. The culture was then grown for a further 3 hours with shaking at 37° C. The cells are harvested by centrifugation and inclusion bodies isolated as described in WO 94/00571. The expression of APT635 was determined by SDS-PAGE and confirmed by the appearance of a novel protein species that migrated at approximately 8000 Da.

Example 30

A Method for the Preparation of Recombinant Human CD59 with a C-terminal Cysteine, Expressed in Baculovirus/Insect Cells (APT2060)

APT2060 is a protein that comprises soluble human CD59 and a C-terminal cysteine residue following codon 81 of the mature CD59 protein (SEQ ID NO: 40) The protein was expressed in a recombinant form in a baculovirus expression system. The polymerase chain reaction was used to produce a truncated cDNA encoding soluble CD59 from a full length cDNA (Davies et al. *J. Exp. Med.* 170, 637, 1989). The 5' oligonucleotide was complementary to 20 bases of the first 7 codons at the N-terminus of the mature CD59 protein, and the 3' oligonucleotide introduced a cysteine codon and a termination codon immediately following the codon for Ser-81 of the mature CD59 protein. These oligonucleotides were also designed to contain recognition sequences for restriction endonucleases compatible with the polylinker site of pBacPAK 8 baculovirus transfer vector (Clontech). The DNA fragment resulting from the PCR amplification was then ligated into pBacPAK 8 DNA. This plasmid was then transfected into Sf9 cells with Bacfectin (Clontech) and BacPAK6 viral DNA which had been cut with the restriction endonuclease Bsu36I. This mixture was deposited onto a 50% confluent monolayer of Sf9 cells and left at 28° C. for 3 days. The supernatant was removed and a plaque assay performed on serial dilutions of the transfection supernatant as described in Baculovirus Expression Protocols, Methods in Molecular Biology series, ed. C. Richardson). Individual plaques were then picked into 0.5 mL IPL-41 medium (Gibco BRL) containing 1% foetal calf serum. The mixture was left at room temperature for 15 minutes and 100 ml of this solution used to inoculate a 50% confluent monolayer of Sf9 cells. The cells were then left to become infected for 4–5 days at 28° C. After this time, the supernatant was removed and assayed for CD59 expression by Western blot as described in methods. For scale-up of the recombinant virus, the supernatant was used as an inoculum to infect more Sf9 cell monolayers as described above; alternatively, the supernatant can be used to infect Sf9 cells grown in suspension cultures. In this method, 100 mL Sf9 cells at a concentration of $5 \times 10^6$ cells/ml in IPL-41 medium containing 1% FCS were inoculated with 50 ml of viral supernatant. The culture was shaken for 5–7 days at 27° C. and cells removed by centrifugation. The recombinant virus may be stored at 4° C. until use. APT2060 may be detected by Western blot as described in Methods and purified using an affinity column as described.

Example 31

A Method for the Preparation of Recombinant Human CD59 with a C-terminal Cysteine, Expressed in Chinese Hamster Ovary Cells (APT2061; SEQ ID. NO: 42)

APT2061 is a protein that comprises soluble human CD59 and a C-terminal cysteine residue at position 71 of the mature protein. The protein may be expressed in a recombinant form in chinese hamster ovary cells as described in Methods. Briefly, the polymerase chain reaction is used to produce a truncated cDNA encoding soluble CD59 from a full length cDNA (Davies et al. *J. Exp. Med.* 170, 637, 1989). The 5' oligonucleotide is complementary to the first codons at the N-terminus of the mature CD59 protein, and the 3' oligonucleotide introduces a cysteine codon and a termination codon immediately following the codon for Asn-70 of the CD59 cDNA. These oligonucleotides can also designed to contain recognition sequences for restriction endonucleases compatible with the polylinker site of a CHO expression vector, as described.

Example 32

A Method for the Conjugation of APT542 to APT633, APT635, APT2060 or APT2061 to Generate Compounds APT2062 (Conjugate of SEQ ID NO: 41 and the Base Peptide of SEQ ID NO: 5), APT2063 (Conjugate of SEQ ID NO: 40 and the Base Peptide of SEQ ID NO: 5), APT2064 (Also a Conjugate of SEQ ID NO: 41 and the Base Peptide of SEQ ID NO: 5) and APT2065 (Conjugate of SEQ ID NO: 42 and the Base Peptide of SEQ ID NO: 5)

Compounds APT2062, APT2063, APT2064 and APT2065 are generated by treating their compounds APT633, APT635, APT2060 and APT2061 with a single molar equivalent of tris-2-carboxyethyl phosphine (TCEP; in 10 mM Hepes, pH7.4) overnight at room temperature. To this mixture is added a solution containing 5 molar equivalents of APT542 (MSWP-1) for 2 hours at room temperature.

Example 33

A Method for th Synthesis and Characterization of APT2057 (SEQ ID NO: 48)

APT2057 is a protein that comprises the short consensus repeats 2,3 and 4 of human CD55 (decay accelerating factor, DAF), with a carboxyl terminal cysteine residue and an amino terminal histidine tag motif expressed in a recombinant form in *E. coli* cells. cDNA to human DAF mRNA was generated from total brain RNA (OriGene Technologies, USA). Reverse transcription was primed with 40 pmol of primer DAF-R (5'GGAATTCTAAGTCAGCAAGCCCATGGTTACT 3') (SEQ ID NO: 49), 3 μg human brain total RNA and other reagents as recommended by the the RT system manufacturers (Promega, Southampton, UK). Half of the RT reaction (10 μl) was used as template for PCR. Reaction volume was increased to 50 μl by the addition of water, buffer, MgCl$_2$ (to 2 mM), DMSO (to 5%) and 20 pmol oligonucleotide DAF-F. (5'GCATATGACCGTCGCGCGGCCGAGC 3') (SEQ ID NO: 50). One unit of Taq polymerase (MBI Fermentas, Vilnius, Lithuania) was added, and the reaction subjected to 35 cycles of PCR (94° C., 30 sec; 64° C., 30 sec; 72° C., 60 sec). A PCR product of 1156 bp was identified by agarose gel electrophoresis, purified from the gel and ligated using standard procedures into the T-cloning vector pUC57/T (MBI-Fermentas, Vilnius, Lithuania). Positive clones were identified by PCR screen, analysed by plasmid restriction map and confirmed by full sequence analysis. A plasmid to encode APT2057 was generated by PCR using the pUC-DAF plasmid as template. Primers were designed to amplify the region of the DAF gene encoding amino acids 97–285 (SCR2–4). The 5' primer incorporated an NdeI restriction enzyme site, and a codon specifying glutamine, thereby introducing an amino terminal methionine-glutamine amino acid pair. The 3' primer added a carboxyl terminal cysteine residue and incorporated an EcoRI restriction enzyme site. The PCR product was cloned into the pUC57/T T-vector as described, sequenced, the insert excised with NdeI and EcoRI, and ligated into pET15b (Novagen, Madison, USA, see Methods section). The product of this ligation is the plasmid pET100-02, which expresses DAF(SCR2–4) as an in-frame fusion of a 20 amino acid leader sequence (MGSSHHHHHHSSGLVPRGSH) (SEQ ID NO: 48) to the 191 amino acid DAF SCRs2–4. pET100-02 DNA was introduced into *E. coli* HAMS113 and transformed cells selected by virtue of their ability to grow on LB+agar plates in the presence of 50 μg/ml ampicillin (LBAMP). A single colony representing HAMS113 containing DNA with the coding capacity for APT2057 was grown overnight at 37° C. with shaking (200 rpm) in LBAMP medium, then diluted 1:100 into 1 liter fresh LBAMP and growth at 37° C. with shaking. Growth was monitored by measurement of culture turbidity at 600 nm, and upon reaching an optical density of 0.6, isopropyl β-D-thiogalactopyranoside (IPTG) was added to a final concentration of 1 mM, followed by a further 3 hours of growth under the same conditions as described above. The expression of APT2057 was analysed by SDS-PAGE (described in methods). APT2057 appeared as a unique protein product of approximately 24000 Da as estimated by comparative mobility with molecular weight standards. Cells containing APT2057 are harvested by centrifugation and inclusion bodies isolated as follows. Briefly, the cells are resuspended in lysis buffer (50 mM Tris, 1 mM ethylene diamine tetra-acetic acid (ETDA), 50 mM NaCl, pH 8.0) at 50 ml per liter of initial culture. The suspension is lysed by two passages through an Emulsiflex homogensier (Glen-Creston, Middlesex UK), followed by centrifugation at 15000×g to purify inclusion bodies. Inclusion bodies are initially resuspended to approximately 1 mg.ml$^{-1}$ (as estimated from SDS-PAGE) in 20 mM Tris, 1 mM EDTA. 50 mM 2-mercaptoethanol, pH8.5, and subsequently diluted to a final concentration of 8M urea by the addition of 10 M urea 20 mM Tris, 1 mM EDTA, 50 mM 2-mercaptoethanol, pH8.5. This suspension is stirred at 4° C. for 16 hours, and insoluble material removed by centrifugation at 15000×g for 30 minutes. The APT2057 is refolded by 1 in 50 dilution into 20 mM ethanolamine, 1 mM EDTA, pH 11 buffer and static incubation at 4° C. for 24 hours. Insoluble material is removed by centrifugation (10000×g, 10 minutes), and soluble material buffer exchanged into Dulbecco's A PBS, pH 7.4 using an XK50×23 cm Sephadex G25 column. Refolded APT205B is analyzed by SDS-PAGE, Western blot and the effectiveness of the protein in a haemolytic assay (described in methods).

Example 34

A Method for the Synthesis and Characterization of APT2058 (SEQ ID NO: 47)

APT2058 is a protein that comprises the short consensus repeats 1,2,3 and 4 of human CD55 (decay accelerating factor, DAF), with a carboxyl terminal cysteine residue and an amino terminal histidine tag motif expressed in a recombinant form in *E. coli* cells. cDNA to human DAF mRNA was generated from total brain RNA as described in Example 9. A plasmid to encode APT2058 was generated by PCR using the pUC-DAF plasmid as template. Primers were designed to amplify the region of the DAF gene encoding amino acids 35–285 (SCR1–4). The 5' primer incorporated an Ndel restriction enzyme site, and a codon specifying glutamine, thereby introducing an amino terminal methionine-glutamine amino acid pair. The 3' primer added a carboxyl terminal cysteine residue and incorporated an EcoRI restriction enzyme site. The PCR product was cloned into the pUC57/T T-vector as described, sequenced, the insert excised with NdeI and EcoRI, and ligated into pET15b (Novagen, Madison, USA). The product of this ligation is the plasmid pET99-02, which expresses DAF (SCR1–4) as an in-frame fusion of a 20 amino acid leader sequence (MGSSHHHHHHSSGLVPRGSH) (SEQ ID NO: 48) to the 251 amino acid DAF SCRs1–4 (APT2058). pET99-02 DNA was introduced into *E. coli* HAMS 113 (see methods) and expression of the recombinant protein induced as described in Example 1. The expression of APT2058 was analysed by SDS-PAGE (described in methods). APT2058 appeared as a unique protein product of approximately 31000 Da as estimated by comparative mobility with molecular weight standards. Cells containing APT2058 were harvested by centrifugation and inclusion bodies isolated as follows. Briefly, the cells were resuspended in lysis buffer (50 mM Tris, 1 mM ethylene diamine tetra-acetic acid (ETDA), 50 mM NaCl, pH 8.0) at 50 ml per liter of initial culture. The suspension was lysed by two passages through an Emulsiflex homogensier (Glen-Creston, Middlesex, UK), followed by centrifugation at 15000×g to purify inclusion bodies. Inclusion bodies were initially resuspended to approximately 1 mg.ml$^{-1}$ (as estimated from SDS-PAGE) in 20 mM Tris, 1 mM EDTA, 50 mM 2-mercaptoethanol, pH8.5, and subsequently diluted to a final concentration of 8M urea by the addition of 10 M urea 20 mM Tris, 1 mM EDTA, 50 mM 2-mercaptoethanol, pH8.5. This suspension was stirred at 4° C. for 16 hours, and insoluble material removed by centrifugation at 15000×g for 30 minutes. The APT2057 was refolded by 1 in 50 dilution into 20 mM ethanolamine, 1 mM EDTA, pH 11 buffer and static incubation at 4° C. for 24 hours. Insoluble material was removed by centrifugation (10000×g, 10 minutes), and soluble material buffer exchanged into Dulbecco's A PBS, pH 7.4 using an XK50× 23 cm Sephadex G25 column. Refolded APT2058 was analysed by SDS-PAGE, Western blot and the effectiveness of the protein in a haemolytic assay (described in methods). Using this assay (at 1:400 dilution of human serum), the concentration of APT2058 required to bring about 50% inhibition of lysis (IH$_{50}$) was approximately 3 nM.

Example 35

A Method for the Synthesis and Characterization of APT2160 (Conjugate of SEQ ID NO: 47 and the Base Peptide of SEQ ID NO: 5)

Compound APT2160 was generated by treating the parent compound APT2058 (at approximately 100 μM) with a three-fold molar excess of 10 mM tris-2-carboxyethyl phosphine (TCEP: in 50 mM Hepes, pH 4.5) overnight at room temperature. To this mixture was added a solution containing five molar equivalents of MSWP-1 (Example 2) in 100% DMSO for 2 hours at room temperature. APT2160 was characterized by observation of a mobility shift on non-reducing SDS-PAGE of approximately 2000 Da, consistent with the addition of a single molecule of APT542 to APT2058. The compound was assayed in the haemolytic assay (at 1:400 dilution of human serum) and an IH$_{50}$ value of 0.03 nM was found.

Example 36

A Method for the Synthesis and Characterization of APT2184 (Conjugate of SEQ ID NO: 46 and the Base Peptide of SEQ ID NO: 5)

Compound APT2184 was generated by treating the parent compound APT2057 with a three-fold molar excess of 10 mM tris-2-carboxyethyl phosphine (TCEP: in 50 mM Hepes, pH 4.5) overnight at room temperature. To this mixture is added a solution containing five molar equivalents of MSWP-1 in 100% DMSO for 2 hours at room temperature.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data combined herein, and thus are considered part of the invention.

This application claims priority to GB 9614871.3, filed Jul. 15, 1996, there entirety of which is hereby incorporated by reference.

What is claimed is:

1. A soluble compound that is directed to an outer membrane of a cell, wherein the soluble compound comprises:
   (1) a soluble polypeptide that inhibits complement; and
   (2) a membrane localization reagent, wherein the membrane localization reagent is soluble and comprises:
      (a) at least one lipophilic binding element comprising aliphatic acyl groups;
      (b) a hydrophilic peptide binding element comprising basic amino acids, wherein the hydrophilic binding element is bound to the lipophilic element; and
      (c) a linker that covalently binds a therapeutic agent to the hydrophilic peptide binding element of the membrane localization reagent to form the soluble compound.

2. The soluble compound of claim 1 wherein the hydrophilic peptide binding element comprises lysine residues.

3. The soluble compound of claim 1 wherein the hydrophilic peptide binding element comprises arginine residues.

4. The soluble compound of claim 1, wherein the soluble peptide that inhibits complement is a soluble CD59 polypeptide or a soluble DAF polypeptide.

5. The soluble compound of claim 1, wherein the lipophilic binding element and the hydrophilic peptide binding element each have a dissociation constant of 1 $\mu$M to 1 mM for a membrane.

6. The soluble compound of claim 1, wherein the lipophilic binding element and the hydrophilic peptide binding element each have a molecular weight of less than 5 kilodaltons.

7. The soluble compound of claim 1, wherein the soluble compound has a dissociation constant of 0.01 to 10 nM for a membrane.

8. A pharmaceutical composition that is directed to an outer membrane of a cell, comprising
   (1) a soluble polypeptide that inhibits complement;
   (2) a membrane localization reagent, wherein the membrane localization reagent is soluble and comprises:
      (a) at least one lipophilic binding element comprising aliphatic acyl groups;
      (b) a hydrophilic peptide binding element comprising basic amino acids, wherein the hydrophilic binding element is bound to the lipophilic element; and
      (c) a linker that covalently binds a therapeutic agent to the hydrophilic peptide binding element of the membrane localization reagent to form the soluble compound; and
   (3) a pharmaceutically acceptable carrier or excipient.

9. The pharmaceutical composition of claim 8 wherein the hydrophilic peptide binding element comprises lysine residues.

10. The pharmaceutical composition of claim 8, wherein the hydrophilic peptide bindin element comprises arginine residues.

11. The pharmaceutical composition of claim 8, wherein the soluble peptide that inhibits complement is a soluble CD59 polypeptide or a soluble DAF polypeptide.

12. The pharmaceutical composition of claim 8, wherein the lipophilic binding element and the a hydrophilic peptide binding element each have a dissociation constant of 1 $\mu$M to 1 mM for a membrane.

13. The pharmaceutical composition of claim 8, wherein the lipophilic binding element and the hydrophilic peptide binding element each have a molecular weight of less than 5 kilodaltons.

14. The pharmaceutical composition of claim 8, wherein the soluble compound has a dissociation constant of 0.01 to 10 nM for a membrane.

* * * * *

SEQUENCE LISTING

<160> NUMBER OF SEQ ID NOS: 53

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcaccgcagt gcatcatccc gaacaaatgc taataaa                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcttttatt agcatttgtt cgggatgatg cactgcg                              37

<210> SEQ ID NO 3
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaccgcagt gcatcatccc gaacaaagac ggtccgaaaa agaagaaaaa gaaatctccg     60
tccaaatctt ccggttgcta ataaa                                          85

<210> SEQ ID NO 4
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agcttttatt agcaaccgga agatttggac ggagatttct tttcttctt tttcggaccg      60 tctttgttcg ggatgatgca ctgcg                                          85

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide used to synthesize MSWP-1
<220> FEATURE:
<223> OTHER INFORMATION: c-term amidation

<400> SEQUENCE: 5

Gly Ser Ser Lys Ser Pro Ser Lys Lys Lys Lys Lys Lys Pro Gly Asp
 1               5                  10                  15

Cys

```
<210> SEQ ID NO 6
<211> LENGTH: 198
<212> TYPE: PRT
<213> ORGANISM: Artificial Sequence
<220> FEATURE:
<223> OTHER INFORMATION: Description of Artificial Sequence: [SCR1-3]-
      Cys protein

<400> SEQUENCE: 6

Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
        50                  55                  60

Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
                100                 105                 110

Ile Trp Asp Asn Glu Thr Pro Ile Cys Asp Arg Ile Pro Cys Gly Leu
            115                 120                 125

Pro Pro Thr Ile Thr Asn Gly Asp Phe Ile Ser Thr Asn Arg Glu Asn
        130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
                180                 185                 190

Ile Ile Pro Asn Lys Cys
            195

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: [SCR1-3]/
      switch fusion protein

<400> SEQUENCE: 7

Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
        50                  55                  60

Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
```

```
                    100                 105                 110
Ile Trp Asp Asn Glu Thr Pro Ile Cys Asp Arg Ile Pro Cys Gly Leu
            115                 120                 125

Pro Pro Thr Ile Thr Asn Gly Asp Phe Ile Ser Thr Asn Arg Glu Asn
        130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys Asp Gly Pro Lys Lys Lys Lys Ser Pro
        195                 200                 205           Pro

Ser Lys Ser Ser Gly Cys
    210

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 8

Asp Gly Pro Lys Lys Lys Lys Lys Ser Pro Ser Lys Ser Ser Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 9

Gly Ser Ser Lys Ser Pro Ser Lys Lys Lys Lys Lys Pro Gly Asp
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 10

Ser Pro Ser Asn Glu Thr Pro Lys Lys Lys Lys Arg Phe Ser Phe
1               5                   10                  15

Lys Lys Ser Gly
            20

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 11
```

-continued

```
Asp Gly Pro Lys Lys Lys Lys Lys Ser Pro Ser Lys Ser Ser Lys
 1               5                  10                  15
```

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 12

```
Ser Lys Asp Gly Lys Lys Lys Lys Lys Ser Lys Thr Lys
 1               5                  10
```

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 13

```
Gly Arg Gly Asp Ser Pro
 1               5
```

<210> SEQ ID NO 14
<211> LENGTH: 209
<212> TYPE: PRT
<213> ORGANISM: Artificial Sequence
<220> FEATURE:
<223> OTHER INFORMATION: Description of Artificial Sequence: SCR1-3 with
      the c-terminal amino acids N195 and K196 replaced by a 14 amino
      acid peptide

<400> SEQUENCE: 14

```
Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
     50                  55                  60

Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                85                  90                  95

Leu Ile Gly Ser Ser Ala Thr Cys Ile Ile Ser Gly Asp Thr Val
                100                 105                 110

Ile Trp Asp Asn Glu Thr Pro Ile Cys Asp Arg Ile Pro Cys Gly Leu
            115                 120                 125

Pro Pro Thr Ile Thr Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190
```

```
Ile Ile Pro Thr Asn Ala Asn Lys Ser Leu Ser Ser Ile Ser Cys Gln
    195                 200                 205
Thr
```

```
<210> SEQ ID NO 15
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctggagcggg cccgcaccgc agtgcatcat cccgaacaaa tgctaataaa agc          53

<210> SEQ ID NO 16
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcttttatta gcatttgttc gggatgatgc actgcggtgc gggcccgctc cag          53

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 17

Asp Gly Pro Ser Glu Ile Leu Arg Gly Asp Phe Ser Ser
  1               5                  10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide used to generate MSWP-2
<220> FEATURE:
<223> OTHER INFORMATION: c-term amidation

<400> SEQUENCE: 18

Cys Asp Gly Pro Lys Lys Lys Lys Lys Ser Pro Ser Lys Ser Ser
  1               5                  10                  15
Lys

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide used to generate MSWP-3

<400> SEQUENCE: 19

Ser Lys Asp Gly Lys Lys Lys Lys Lys Ser Lys Thr Lys Cys
  1               5                  10              15

<210> SEQ ID NO 20
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide used to generate TCTP-1

<400> SEQUENCE: 20

Cys Ser Ala Ala Pro Ser Ser Gly Phe Arg Ile Leu Leu Leu Lys Val
 1               5                  10                  15

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 21

Gly Asn Glu Gln Ser Phe Arg Val Asp Leu Arg Thr Leu Leu Arg Tyr
 1               5                  10                  15

Ala

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 22

Gly Phe Arg Ile Leu Leu Leu Lys Val
 1               5

<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: SCR1-3 with
      an additional 14 amino acid residues at the c-terminus

<400> SEQUENCE: 23

Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
     50                  55                  60

Arg Asn Pro Pro Asp Pro Val Asn Gly Met Val His Val Ile Lys Gly
 65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
               100                 105                 110

Ile Trp Asp Asn Glu Thr Pro Ile Cys Asp Arg Ile Pro Cys Gly Leu
           115                 120                 125

Pro Pro Thr Ile Thr Asn Gly Asp Phe Ile Ser Thr Asn Arg Glu Asn
   130                 135                 140
```

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys Asp Gly Pro Ser Glu Ile Leu Arg Gly Asp Phe
        195                 200                 205

Ser Ser Cys
    210

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 24

Ser Ala Ala Pro Ser Ser Gly Phe Arg Ile Leu Leu Leu Lys Val
1               5                   10                  15

<210> SEQ ID NO 25
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgcaccgcag tgcatcatcc cgaacaaaga tggcccgagc gaaattctgc gtggcgattt    60
tagcagctgc ta                                                       72

<210> SEQ ID NO 26
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acgttagcag ctgctaaaat cgccacgcag aatttcgctc gggccatctt tgttcgggat    60
gatgcactgc ggtgcgggcc                                               80

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Myristoyl/
      Electrostatic Swith Peptide Reagent 1 (MSWP-1)
<220> FEATURE:
<223> OTHER INFORMATION: c-term amidation

<400> SEQUENCE: 27

Gly Ser Ser Lys Ser Pro Ser Lys Lys Lys Lys Lys Lys Pro Gly Asp
1               5                   10                  15

Cys

```
<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Myristoyl/
      Electrostatic Switch Peptide Reagent 2 (MSWP-2)
<220> FEATURE:
<223> OTHER INFORMATION: c-term amidation

<400> SEQUENCE: 28

Cys Asp Gly Pro Lys Lys Lys Lys Lys Ser Pro Ser Lys Ser Ser
 1               5                  10                  15

Lys

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Myristoyl/
      Electrostatic Switch Peptide Reagent 3 (MSWP-3)
<220> FEATURE:
<223> OTHER INFORMATION: c-term amidation

<400> SEQUENCE: 29

Ser Lys Asp Gly Lys Lys Lys Lys Lys Ser Lys Thr Lys Cys
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: T-cell
      targeting peptide reagent 1 (TCTP-1)

<400> SEQUENCE: 30

Cys Ser Ala Ala Pro Ser Ser Gly Phe Arg Ile Leu Leu Leu Lys Val
 1               5                  10                  15

<210> SEQ ID NO 31
<211> LENGTH: 214
<212> TYPE: PRT
<213> ORGANISM: Artificial Sequence
<220> FEATURE:
<223> OTHER INFORMATION: Description of Artificial Sequence: [SCR1-3/
      switch fusion]-[MAET]
<220> FEATURE:
<223> OTHER INFORMATION: c-term Cys is linked to (CH2)2-CONH-(CH2)12-
      CH3

<400> SEQUENCE: 31

Met Gln Cys Asn Ala Pro Glu Trp Leu Pro Phe Ala Arg Pro Thr Asn
 1               5                  10                  15

Leu Thr Asp Glu Phe Glu Phe Pro Ile Gly Thr Tyr Leu Asn Tyr Glu
                20                  25                  30

Cys Arg Pro Gly Tyr Ser Gly Arg Pro Phe Ser Ile Ile Cys Leu Lys
            35                  40                  45

Asn Ser Val Trp Thr Gly Ala Lys Asp Arg Cys Arg Arg Lys Ser Cys
        50                  55                  60

Arg Asn Pro Pro Asp Pro Val Asn Gly Met Val His Val Ile Lys Gly
 65                 70                  75                  80

Ile Gln Phe Gly Ser Gln Ile Lys Tyr Ser Cys Thr Lys Gly Tyr Arg
                85                  90                  95
```

```
Leu Ile Gly Ser Ser Ser Ala Thr Cys Ile Ile Ser Gly Asp Thr Val
            100                 105                 110

Ile Trp Asp Asn Glu Thr Pro Ile Cys Asp Arg Ile Pro Cys Gly Leu
        115                 120                 125

Pro Pro Thr Ile Thr Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
145                 150                 155                 160

Gly Arg Lys Val Phe Glu Leu Val Gly Glu Pro Ser Ile Tyr Cys Thr
                165                 170                 175

Ser Asn Asp Asp Gln Val Gly Ile Trp Ser Gly Pro Ala Pro Gln Cys
            180                 185                 190

Ile Ile Pro Asn Lys Asp Gly Pro Lys Lys Lys Lys Lys Ser Pro
        195                 200                 205

Ser Lys Ser Ser Gly Cys
    210

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 32

Ala Ala Pro Ser Val Ile Gly Phe Arg Ile Leu Leu Leu Lys Val Ala
  1               5                  10                  15

Gly

<210> SEQ ID NO 33
<211> LENGTH: 215
<212> TYPE: PRT
<213> ORGANISM: Artificial Sequence
<220> FEATURE:
<223> OTHER INFORMATION: Description of Artificial Sequence: SCR1-3 with
      an additional c-terminal 18 amino acids

<400> SEQUENCE: 33

Met Gln Cys Asn Ala Pro Glu Trp Leu Pro Phe Ala Arg Pro Thr Asn
  1               5                  10                  15

Leu Thr Asp Glu Phe Glu Phe Pro Ile Gly Thr Tyr Leu Asn Tyr Glu
            20                  25                  30

Cys Arg Pro Gly Tyr Ser Gly Arg Pro Phe Ser Ile Ile Cys Leu Lys
        35                  40                  45

Asn Ser Val Trp Thr Gly Ala Lys Asp Arg Cys Arg Arg Lys Ser Cys
    50                  55                  60

Arg Asn Pro Pro Asp Pro Val Asn Gly Met Val His Val Ile Lys Gly
65                  70                  75                  80

Ile Gln Phe Gly Ser Gln Ile Lys Tyr Ser Cys Thr Lys Gly Tyr Arg
                85                  90                  95

Leu Ile Gly Ser Ser Ser Ala Thr Cys Ile Ile Ser Gly Asp Thr Val
            100                 105                 110

Ile Trp Asp Asn Glu Thr Pro Ile Cys Asp Arg Ile Pro Cys Gly Leu
        115                 120                 125

Pro Pro Thr Ile Thr Asn Gly Asp Phe Ile Ser Thr Asn Arg Glu Asn
    130                 135                 140

Phe His Tyr Gly Ser Val Val Thr Tyr Arg Cys Asn Pro Gly Ser Gly
```

```
                   145                 150                 155                 160
Gly Arg Lys Val Phe Glu Leu Val Gly Glu Pro Ser Ile Tyr Cys Thr
                    165                 170                 175

Ser Asn Asp Asp Gln Val Gly Ile Trp Ser Gly Pro Ala Pro Gln Cys
                180                 185                 190

Ile Ile Pro Asn Lys Ala Ala Pro Ser Val Ile Gly Phe Arg Ile Leu
        195                 200                 205

Leu Leu Lys Val Ala Gly Cys
    210                 215

<210> SEQ ID NO 34
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgcaccgcag tgcatcatcc cgaacaaagc ggcgcccagc gtgattggct tccgtattct      60
gctgctgaaa gtggcgggct gcta                                            84

<210> SEQ ID NO 35
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agcttagcag cccgccactt tcagcagcag aatacggaag ccaatcacgc tgggcgccgc      60
tttgttcggg atgatgcact gcggtgcggg cc                                   92

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 36

Asp Gly Pro Lys Lys Lys Lys Lys Ser Pro Ser Lys Ser Ser Gly
  1               5                  10                  15

Cys

<210> SEQ ID NO 37
<211> LENGTH: 77
<212> TYPE: PRT
<213> ORGANISM: Artificial Sequence
<220> FEATURE:
<223> OTHER INFORMATION: Description of Artificial Sequence: Synthetic
      protein APT631

<400> SEQUENCE: 37

Leu Gln Cys Tyr Asn Cys Pro Asn Pro Thr Ala Asp Cys Lys Thr Ala
  1               5                  10                  15

Val Asn Cys Ser Ser Asp Phe Asp Ala Cys Leu Ile Thr Lys Ala Gly
                 20                  25                  30

Leu Gln Val Tyr Asn Lys Cys Trp Lys Phe Glu His Cys Asn Phe Asn
             35                  40                  45
```

```
Asp Val Thr Thr Arg Leu Arg Glu Asn Glu Leu Thr Tyr Tyr Cys Cys
        50                  55                  60

Lys Lys Asp Leu Cys Asn Phe Asn Glu Gln Leu Glu Asn
 65                  70                  75
```

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      protein APT542
<220> FEATURE:
<223> OTHER INFORMATION: c-term amidation

<400> SEQUENCE: 38

```
Gly Ser Ser Lys Ser Pro Ser Lys Lys Lys Lys Lys Pro Gly Asp
 1               5                  10                  15

Cys
```

<210> SEQ ID NO 39
<211> LENGTH: 70
<212> TYPE: PRT
<213> ORGANISM: Artificial Sequence
<220> FEATURE:
<223> OTHER INFORMATION: Description of Artificial Sequence: Synthetic
      protein APT634

<400> SEQUENCE: 39

```
Leu Gln Cys Tyr Asn Cys Pro Asn Pro Thr Ala Asp Cys Lys Thr Ala
 1               5                  10                  15

Val Ala Cys Ser Ser Asp Phe Asp Ala Cys Leu Ile Thr Lys Ala Gly
                20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn
 65                  70
```

<210> SEQ ID NO 40
<211> LENGTH: 82
<212> TYPE: PRT
<213> ORGANISM: Artificial Sequence
<220> FEATURE:
<223> OTHER INFORMATION: Description of Artificial Sequence: Synthetic
      protein APT2060

<400> SEQUENCE: 40

```
Leu Gln Cys Tyr Asn Cys Pro Asn Pro Thr Ala Asp Cys Lys Thr Ala
 1               5                  10                  15

Val Asn Cys Ser Ser Asp Phe Asp Ala Cys Leu Ile Thr Lys Ala Gly
                20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn Phe Asn Glu Gln Leu Glu Asn Gly Gly Thr
 65                  70                  75                  80

Ser Cys
```

```
<210> SEQ ID NO 41
<211> LENGTH: 83
<212> TYPE: PRT
<213> ORGANISM: Artificial Sequence
<220> FEATURE:
<223> OTHER INFORMATION: Description of Artificial Sequence: Synthetic
      protein APT635

<400> SEQUENCE: 41

Met Leu Gln Cys Tyr Asn Cys Pro Asn Pro Thr Ala Asp Cys Lys Thr
 1               5                  10                  15

Ala Val Asn Cys Ser Ser Asp Phe Asp Ala Cys Leu Ile Thr Lys Ala
                20                  25                  30

Gly Leu Gln Val Tyr Asn Lys Cys Trp Lys Phe Glu His Cys Asn Phe
            35                  40                  45

Asn Asp Val Thr Thr Arg Leu Arg Glu Asn Glu Leu Thr Tyr Tyr Cys
        50                  55                  60

Cys Lys Lys Asp Leu Cys Asn Phe Asn Glu Gln Leu Glu Asn Gly Gly
 65                  70                  75                  80

Thr Ser Cys

<210> SEQ ID NO 42
<211> LENGTH: 71
<212> TYPE: PRT
<213> ORGANISM: Artificial Sequence
<220> FEATURE:
<223> OTHER INFORMATION: Description of Artificial Sequence: Synthetic
      protein APT2061

<400> SEQUENCE: 42

Leu Gln Cys Tyr Asn Cys Pro Asn Pro Thr Ala Asp Cys Lys Thr Ala
 1               5                  10                  15

Val Ala Cys Ser Ser Asp Phe Asp Ala Cys Leu Ile Thr Lys Ala Gly
                20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn Cys
 65                  70

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence:
      Illustrative amino acid sequence

<400> SEQUENCE: 43

Ala Ala Pro Ser Val Ile Gly Phe Arg Ile Leu Leu Leu Lys Val Ala
 1               5                  10                  15

Gly Cys

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence:
      Illustrative amino acid sequence
```

-continued

```
<400> SEQUENCE: 44

Asp Gly Pro Ser Glu Ile Leu Arg Gly Asp Phe Ser Ser Cys
 1               5                  10

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:
      Illustrative oligonucleotide

<400> SEQUENCE: 45
cctctggcca aatgtacctc tcgtgcacat tgctga                                36

<210> SEQ ID NO 46
<211> LENGTH: 211
<212> TYPE: PRT
<213> ORGANISM: Artificial Sequence
<220> FEATURE:
<223> OTHER INFORMATION: Description of Artificial Sequence: Synthetic
      protein APT2057

<400> SEQUENCE: 46

Met Gly Ser Ser His His His His His His Ser Ser Gly Leu Val Pro
 1               5                  10                  15

Arg Gly Ser His Met Ser Cys Glu Val Pro Thr Arg Leu Asn Ser Ala
            20                  25                  30

Ser Leu Lys Gln Pro Tyr Ile Thr Gln Asn Tyr Phe Pro Val Gly Thr
        35                  40                  45

Val Val Glu Tyr Glu Cys Arg Pro Gly Tyr Arg Arg Glu Pro Ser Leu
    50                  55                  60

Ser Pro Lys Leu Thr Cys Leu Gln Asn Leu Lys Trp Ser Thr Ala Val
65                  70                  75                  80

Glu Phe Cys Lys Lys Lys Ser Cys Pro Asn Pro Gly Glu Ile Arg Asn
                85                  90                  95

Gly Gln Ile Asp Val Pro Gly Gly Ile Leu Phe Gly Ala Thr Ile Ser
            100                 105                 110

Phe Ser Cys Asn Thr Gly Tyr Lys Leu Phe Gly Ser Thr Ser Ser Phe
        115                 120                 125

Cys Leu Ile Ser Gly Ser Ser Val Gln Trp Ser Asp Pro Leu Pro Glu
    130                 135                 140

Cys Arg Glu Ile Tyr Cys Pro Ala Pro Pro Gln Ile Asp Asn Gly Ile
145                 150                 155                 160

Ile Gln Gly Glu Arg Asp His Tyr Gly Tyr Arg Gln Ser Val Thr Tyr
                165                 170                 175

Ala Cys Asn Lys Gly Phe Thr Met Ile Gly Glu His Ser Ile Tyr Cys
            180                 185                 190

Thr Val Asn Asn Asp Glu Gly Glu Trp Ser Gly Pro Pro Pro Glu Cys
        195                 200                 205

Arg Gly Cys
    210

<210> SEQ ID NO 47
<211> LENGTH: 274
<212> TYPE: PRT
<213> ORGANISM: Artificial Sequence
<220> FEATURE:
<223> OTHER INFORMATION: Description of Artificial Sequence: Synthetic
      protein APT2058
```

<400> SEQUENCE: 47

```
Met Gly Ser Ser His His His His His Ser Ser Gly Leu Val Pro
 1               5                  10                  15

Arg Gly Ser His Met Gln Asp Cys Gly Leu Pro Pro Asp Val Pro Asn
             20                  25                  30

Ala Gln Pro Ala Leu Glu Gly Arg Thr Ser Phe Pro Glu Asp Thr Val
         35                  40                  45

Ile Thr Tyr Lys Cys Glu Glu Ser Phe Val Lys Ile Pro Gly Glu Lys
     50                  55                  60

Asp Ser Val Ile Cys Leu Lys Gly Ser Gln Trp Ser Asp Ile Glu Glu
 65                  70                  75                  80

Phe Cys Asn Arg Ser Cys Glu Val Pro Thr Arg Leu Asn Ser Ala Ser
                 85                  90                  95

Leu Lys Gln Pro Tyr Ile Thr Gln Asn Tyr Phe Pro Val Gly Thr Val
            100                 105                 110

Val Glu Tyr Glu Cys Arg Pro Gly Tyr Arg Arg Glu Pro Ser Leu Ser
        115                 120                 125

Pro Lys Leu Thr Cys Leu Gln Asn Leu Lys Trp Ser Thr Ala Val Glu
    130                 135                 140

Phe Cys Lys Lys Lys Ser Cys Pro Asn Pro Gly Glu Ile Arg Asn Gly
145                 150                 155                 160

Gln Ile Asp Val Pro Gly Gly Ile Leu Phe Gly Ala Thr Ile Ser Phe
                165                 170                 175

Ser Cys Asn Thr Gly Tyr Lys Leu Phe Gly Ser Thr Ser Ser Phe Cys
            180                 185                 190

Leu Ile Ser Gly Ser Ser Val Gln Trp Ser Asp Pro Leu Pro Glu Cys
        195                 200                 205

Arg Glu Ile Tyr Cys Pro Ala Pro Pro Gln Ile Asp Asn Gly Ile Ile
    210                 215                 220

Gln Gly Glu Arg Asp His Tyr Gly Tyr Arg Gln Ser Val Thr Tyr Ala
225                 230                 235                 240

Cys Asn Lys Gly Phe Thr Met Ile Gly Glu His Ser Ile Tyr Cys Thr
                245                 250                 255

Val Asn Asn Asp Glu Gly Glu Trp Ser Gly Pro Pro Glu Cys Arg
                260                 265                 270

Gly Cys
```

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      leader sequence

<400> SEQUENCE: 48

```
Met Gly Ser Ser His His His His His Ser Ser Gly Leu Val Pro
 1               5                  10                  15

Arg Gly Ser His
             20
```

<210> SEQ ID NO 49
<211> LENGTH: 31
<212> TYPE: DNA
<213> ORGANISM: Artificial Sequence
<220> FEATURE:

-continued

```
<223> OTHER INFORMATION: Description of Artificial Sequence: Primer DAF-
      R

<400> SEQUENCE: 49
ggaattctaa gtcagcaagc ccatggttac t                              31

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide DAF-F

<400> SEQUENCE: 50
gcatatgacc gtcgcgcggc cgagc                                     25

<210> SEQ ID NO 51
<211> LENGTH: 527
<212> TYPE: PRT
<213> ORGANISM: Homo sapiens
<220> FEATURE:
<223> OTHER INFORMATION: tissue plasminogen activator

<400> SEQUENCE: 51

Ser Tyr Gln Val Ile Cys Arg Asp Glu Lys Thr Gln Met Ile Tyr Gln
  1               5                  10                  15

Gln His Gln Ser Trp Leu Arg Pro Val Leu Arg Ser Asn Arg Val Glu
             20                  25                  30

Tyr Cys Trp Cys Asn Ser Gly Arg Ala Gln Cys His Ser Val Pro Val
         35                  40                  45

Lys Ser Cys Ser Glu Pro Arg Cys Phe Asn Gly Gly Thr Cys Gln Gln
     50                  55                  60

Ala Leu Tyr Phe Ser Asp Phe Val Cys Gln Cys Pro Glu Gly Phe Ala
 65                  70                  75                  80

Gly Lys Cys Cys Glu Ile Asp Thr Arg Ala Thr Cys Tyr Glu Asp Gln
                 85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
```

-continued

```
                260                 265                 270
Gln Phe Arg Ile Lys Gly Gly Leu Phe Ala Asp Ile Ala Ser His Pro
                275                 280                 285

Trp Gln Ala Ala Ile Phe Ala Lys His Arg Arg Ser Pro Gly Glu Arg
290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Gln Lys Phe
                340                 345                 350

Glu Val Glu Lys Tyr Ile Val His Lys Glu Phe Asp Asp Thr Tyr
                355                 360                 365

Asp Asn Asp Ile Ala Leu Leu Gln Leu Lys Ser Asp Ser Ser Arg Cys
370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
                405                 410                 415

His Glu Ala Leu Ser Pro Phe Tyr Ser Glu Arg Leu Lys Glu Ala His
                420                 425                 430

Val Arg Leu Tyr Pro Ser Ser Arg Cys Thr Ser Gln His Leu Leu Asn
                435                 440                 445

Arg Thr Val Thr Asp Asn Met Leu Cys Ala Gly Asp Thr Arg Ser Gly
                450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495

Ser Trp Gly Leu Gly Cys Gly Gln Lys Asp Val Pro Gly Val Tyr Thr
                500                 505                 510

Lys Val Thr Asn Tyr Leu Asp Trp Ile Arg Asp Asn Met Arg Pro
                515                 520                 525

<210> SEQ ID NO 52
<211> LENGTH: 1947
<212> TYPE: PRT
<213> ORGANISM: Homo sapiens
<220> FEATURE:
<223> OTHER INFORMATION: CR1

<400> SEQUENCE: 52

Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
                20                  25                  30

Arg Pro Gly Tyr Ser Gly Arg Pro Phe Ser Ile Ile Cys Leu Lys Asn
                35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
```

-continued

```
              100                 105                 110
Trp Asp Asn Glu Thr Pro Ile Cys Asp Arg Ile Pro Cys Gly Leu Pro
              115                 120                 125

Pro Thr Ile Thr Asn Gly Asp Phe Ile Ser Thr Asn Arg Glu Asn Phe
          130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
              165                 170                 175

Asn Asp Asp Gln Val Gly Ile Trp Ser Gly Pro Ala Pro Gln Cys Ile
          180                 185                 190

Ile Pro Asn Lys Cys Thr Pro Pro Asn Val Glu Asn Gly Ile Leu Val
              195                 200                 205

Ser Asp Asn Arg Ser Leu Phe Ser Leu Asn Glu Val Val Glu Phe Arg
          210                 215                 220

Cys Gln Pro Gly Phe Val Met Lys Gly Pro Arg Arg Val Lys Cys Gln
225                 230                 235                 240

Ala Leu Asn Lys Trp Glu Pro Glu Leu Pro Ser Cys Ser Arg Val Cys
              245                 250                 255

Gln Pro Pro Pro Asp Val Leu His Ala Glu Arg Thr Gln Arg Asp Lys
          260                 265                 270

Asp Asn Phe Ser Pro Gly Gln Glu Val Phe Tyr Ser Cys Glu Pro Gly
          275                 280                 285

Tyr Asp Leu Arg Gly Ala Ala Ser Met Arg Cys Thr Pro Gln Gly Asp
          290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
              325                 330                 335

Leu Gly Ala Lys Val Asp Phe Val Cys Asp Glu Gly Phe Gln Leu Lys
              340                 345                 350

Gly Ser Ser Ala Ser Tyr Cys Val Leu Ala Gly Met Glu Ser Leu Trp
          355                 360                 365

Asn Ser Ser Val Pro Val Cys Glu Gln Ile Phe Cys Pro Ser Pro Pro
          370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
              405                 410                 415

Thr Ser Phe Asp Leu Ile Gly Glu Ser Thr Ile Arg Cys Thr Ser Asp
              420                 425                 430

Pro Gln Gly Asn Gly Val Trp Ser Ser Pro Ala Pro Arg Cys Gly Ile
          435                 440                 445

Leu Gly His Cys Gln Ala Pro Asp His Phe Leu Phe Ala Lys Leu Lys
450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
              485                 490                 495

Asp Asn Leu Val Trp Ser Ser Pro Lys Asp Val Cys Lys Arg Lys Ser
          500                 505                 510

Cys Lys Thr Pro Pro Asp Pro Val Asn Gly Met Val His Val Ile Thr
          515                 520                 525
```

-continued

```
Asp Ile Gln Val Gly Ser Arg Ile Asn Tyr Ser Cys Thr Thr Gly His
    530                 535                 540
Arg Leu Ile Gly His Ser Ser Ala Glu Cys Ile Leu Ser Gly Asn Ala
545                 550                 555                 560
Ala His Trp Ser Thr Lys Pro Pro Ile Cys Gln Arg Ile Pro Cys Gly
                565                 570                 575
Leu Pro Pro Thr Ile Ala Asn Gly Asp Phe Ile Ser Thr Asn Arg Glu
                580                 585                 590
Asn Phe His Tyr Gly Ser Val Val Thr Tyr Arg Cys Asn Pro Gly Ser
            595                 600                 605
Gly Gly Arg Lys Val Phe Glu Leu Val Gly Glu Pro Ser Ile Tyr Cys
    610                 615                 620
Thr Ser Asn Asp Asp Gln Val Gly Ile Trp Ser Gly Pro Ala Pro Gln
625                 630                 635                 640
Cys Ile Ile Pro Asn Lys Cys Thr Pro Pro Asn Val Glu Asn Gly Ile
                645                 650                 655
Leu Val Ser Asp Asn Arg Ser Leu Phe Ser Leu Asn Glu Val Val Glu
                660                 665                 670
Phe Arg Cys Gln Pro Gly Phe Val Met Lys Gly Pro Arg Arg Val Lys
            675                 680                 685
Cys Gln Ala Leu Asn Lys Trp Glu Pro Glu Leu Pro Ser Cys Ser Arg
    690                 695                 700
Val Cys Gln Pro Pro Asp Val Leu His Ala Glu Arg Thr Gln Arg
705                 710                 715                 720
Asp Lys Asp Asn Phe Ser Pro Gly Gln Glu Val Phe Tyr Ser Cys Glu
                725                 730                 735
Pro Gly Tyr Asp Leu Arg Gly Ala Ala Ser Met Arg Cys Thr Pro Gln
                740                 745                 750
Gly Asp Trp Ser Pro Ala Ala Pro Thr Cys Glu Val Lys Ser Cys Asp
            755                 760                 765
Asp Phe Met Gly Gln Leu Leu Asn Gly Arg Val Leu Phe Pro Val Asn
    770                 775                 780
Leu Gln Leu Gly Ala Lys Val Asp Phe Val Cys Asp Glu Gly Phe Gln
785                 790                 795                 800
Leu Lys Gly Ser Ser Ala Ser Tyr Cys Val Leu Ala Gly Met Glu Ser
                805                 810                 815
Leu Trp Asn Ser Ser Val Pro Val Cys Glu Gln Ile Phe Cys Pro Ser
                820                 825                 830
Pro Pro Val Ile Pro Asn Gly Arg His Thr Gly Lys Pro Leu Glu Val
            835                 840                 845
Phe Pro Phe Gly Lys Ala Val Asn Tyr Thr Cys Asp Pro His Pro Asp
    850                 855                 860
Arg Gly Thr Ser Phe Asp Leu Ile Gly Glu Ser Thr Ile Arg Cys Thr
865                 870                 875                 880
Ser Asp Pro Gln Gly Asn Gly Val Trp Ser Ser Pro Ala Pro Arg Cys
                885                 890                 895
Gly Ile Leu Gly His Cys Gln Ala Pro Asp His Phe Leu Phe Ala Lys
                900                 905                 910
Leu Lys Thr Gln Thr Asn Ala Ser Asp Phe Pro Ile Gly Thr Ser Leu
            915                 920                 925
Lys Tyr Glu Cys Arg Pro Glu Tyr Tyr Gly Arg Pro Phe Ser Ile Thr
    930                 935                 940
```

-continued

```
Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
            965                 970                 975

Ile Thr Asp Ile Gln Val Gly Ser Arg Ile Asn Tyr Ser Cys Thr Thr
        980                 985                 990

Gly His Arg Leu Ile Gly His Ser Ala Glu Cys Ile Leu Ser Gly
    995                1000                1005

Asn Thr Ala His Trp Ser Thr Lys Pro Pro Ile Cys Gln Arg Ile Pro
1010                1015                1020

Cys Gly Leu Pro Pro Thr Ile Ala Asn Gly Asp Phe Ile Ser Thr Asn
1025                1030                1035                1040

Arg Glu Asn Phe His Tyr Gly Ser Val Val Thr Tyr Arg Cys Asn Leu
                1045                1050                1055

Gly Ser Arg Gly Arg Lys Val Phe Glu Leu Val Gly Glu Pro Ser Ile
            1060                1065                1070

Tyr Cys Thr Ser Asn Asp Asp Gln Val Gly Ile Trp Ser Gly Pro Ala
        1075                1080                1085

Pro Gln Cys Ile Ile Pro Asn Lys Cys Thr Pro Pro Asn Val Glu Asn
    1090                1095                1100

Gly Ile Leu Val Ser Asp Asn Arg Ser Leu Phe Ser Leu Asn Glu Val
1105                1110                1115                1120

Val Glu Phe Arg Cys Gln Pro Gly Phe Val Met Lys Gly Pro Arg Arg
                1125                1130                1135

Val Lys Cys Gln Ala Leu Asn Lys Trp Glu Pro Glu Leu Pro Ser Cys
            1140                1145                1150

Ser Arg Val Cys Gln Pro Pro Glu Ile Leu His Gly Glu His Thr
        1155                1160                1165

Pro Ser His Gln Asp Asn Phe Ser Pro Gly Gln Glu Val Phe Tyr Ser
    1170                1175                1180

Cys Glu Pro Gly Tyr Asp Leu Arg Gly Ala Ala Ser Leu His Cys Thr
1185                1190                1195                1200

Pro Gln Gly Asp Trp Ser Pro Glu Ala Pro Arg Cys Ala Val Lys Ser
                1205                1210                1215

Cys Asp Asp Phe Leu Gly Gln Leu Pro His Gly Arg Val Leu Phe Pro
            1220                1225                1230

Leu Asn Leu Gln Leu Gly Ala Lys Val Ser Phe Val Cys Asp Glu Gly
        1235                1240                1245

Phe Arg Leu Lys Gly Ser Ser Val Ser His Cys Val Leu Val Gly Met
    1250                1255                1260

Arg Ser Leu Trp Asn Asn Ser Val Pro Val Cys Glu His Ile Phe Cys
1265                1270                1275                1280

Pro Asn Pro Pro Ala Ile Leu Asn Gly Arg His Thr Gly Thr Pro Ser
                1285                1290                1295

Gly Asp Ile Pro Tyr Gly Lys Glu Ile Ser Tyr Thr Cys Asp Pro His
            1300                1305                1310

Pro Asp Arg Gly Met Thr Phe Asn Leu Ile Gly Glu Ser Thr Ile Arg
        1315                1320                1325

Cys Thr Ser Asp Pro His Gly Asn Gly Val Trp Ser Ser Pro Ala Pro
    1330                1335                1340

Arg Cys Glu Leu Ser Val Arg Ala Gly His Cys Lys Thr Pro Glu Gln
1345                1350                1355                1360

Phe Pro Phe Ala Ser Pro Thr Ile Pro Ile Asn Asp Phe Glu Phe Pro
```

```
                 1365             1370             1375
Val Gly Thr Ser Leu Asn Tyr Glu Cys Arg Pro Gly Tyr Phe Gly Lys
            1380             1385             1390
Met Phe Ser Ile Ser Cys Leu Glu Asn Leu Val Trp Ser Ser Val Glu
        1395             1400             1405
Asp Asn Cys Arg Arg Lys Ser Cys Gly Pro Pro Glu Pro Phe Asn
    1410             1415             1420
Gly Met Val His Ile Asn Thr Asp Thr Gln Phe Gly Ser Thr Val Asn
1425             1430             1435             1440
Tyr Ser Cys Asn Glu Gly Phe Arg Leu Ile Gly Ser Pro Ser Thr Thr
            1445             1450             1455
Cys Leu Val Ser Gly Asn Asn Val Thr Trp Asp Lys Lys Ala Pro Ile
        1460             1465             1470
Cys Glu Ile Ile Ser Cys Glu Pro Pro Thr Ile Ser Asn Gly Asp
    1475             1480             1485
Phe Tyr Ser Asn Asn Arg Thr Ser Phe His Asn Gly Thr Val Val Thr
    1490             1495             1500
Tyr Gln Cys His Thr Gly Pro Asp Gly Glu Gln Leu Phe Glu Leu Val
1505             1510             1515             1520
Gly Glu Arg Ser Ile Tyr Cys Thr Ser Lys Asp Asp Gln Val Gly Val
            1525             1530             1535
Trp Ser Ser Pro Pro Pro Arg Cys Ile Ser Thr Asn Lys Cys Thr Ala
        1540             1545             1550
Pro Glu Val Glu Asn Ala Ile Arg Val Pro Gly Asn Arg Ser Phe Phe
        1555             1560             1565
Ser Leu Thr Glu Ile Ile Arg Phe Arg Cys Gln Pro Gly Phe Val Met
    1570             1575             1580
Val Gly Ser His Thr Val Gln Cys Gln Thr Asn Gly Arg Trp Gly Pro
1585             1590             1595             1600
Lys Leu Pro His Cys Ser Arg Val Cys Gln Pro Pro Glu Ile Leu
            1605             1610             1615
His Gly Glu His Thr Leu Ser His Gln Asp Asn Phe Ser Pro Gly Gln
            1620             1625             1630
Glu Val Phe Tyr Ser Cys Glu Pro Ser Tyr Asp Leu Arg Gly Ala Ala
        1635             1640             1645
Ser Leu His Cys Thr Pro Gln Gly Asp Trp Ser Pro Glu Ala Pro Arg
    1650             1655             1660
Cys Thr Val Lys Ser Cys Asp Asp Phe Leu Gly Gln Leu Pro His Gly
1665             1670             1675             1680
Arg Val Leu Leu Pro Leu Asn Leu Gln Leu Gly Ala Lys Val Ser Phe
            1685             1690             1695
Val Cys Asp Glu Gly Phe Arg Leu Lys Gly Arg Ser Ala Ser His Cys
        1700             1705             1710
Val Leu Ala Gly Met Lys Ala Leu Trp Asn Ser Ser Val Pro Val Cys
    1715             1720             1725
Glu Gln Ile Phe Cys Pro Asn Pro Pro Ala Ile Leu Asn Gly Arg His
    1730             1735             1740
Thr Gly Thr Pro Phe Gly Asp Ile Pro Tyr Gly Lys Glu Ile Ser Tyr
1745             1750             1755             1760
Ala Cys Asp Thr His Pro Asp Arg Gly Met Thr Phe Asn Leu Ile Gly
            1765             1770             1775
Glu Ser Ser Ile Arg Cys Thr Ser Asp Pro Gln Gly Asn Gly Val Trp
        1780             1785             1790
```

-continued

```
Ser Ser Pro Ala Pro Arg Cys Glu Leu Ser Val Pro Ala Ala Cys Pro
    1795                1800                1805

His Pro Pro Lys Ile Gln Asn Gly His Tyr Ile Gly Gly His Val Ser
    1810                1815                1820

Leu Tyr Leu Pro Gly Met Thr Ile Ser Tyr Thr Cys Asp Pro Gly Tyr
1825                1830                1835                1840

Leu Leu Val Gly Lys Gly Phe Ile Phe Cys Thr Asp Gln Gly Ile Trp
                1845                1850                1855

Ser Gln Leu Asp His Tyr Cys Lys Glu Val Asn Cys Ser Phe Pro Leu
                1860                1865                1870

Phe Met Asn Gly Ile Ser Lys Glu Leu Glu Met Lys Lys Val Tyr His
        1875                1880                1885

Tyr Gly Asp Tyr Val Thr Leu Lys Cys Glu Asp Gly Tyr Thr Leu Glu
    1890                1895                1900

Gly Ser Pro Trp Ser Gln Cys Gln Ala Asp Asp Arg Trp Asp Pro Pro
1905                1910                1915                1920

Leu Ala Lys Cys Thr Ser Arg Ala His Cys Cys Asp Gly Pro Lys Lys
                1925                1930                1935

Lys Lys Lys Lys Ser Pro Ser Lys Ser Ser Gly
            1940                1945

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 3-10 residues
      according to the specification as filed

<400> SEQUENCE: 53

Lys Lys Lys Lys Lys Lys Lys Lys Lys Lys
1               5                   10
```